US009125735B2

(12) United States Patent
de Juan, Jr. et al.

(10) Patent No.: US 9,125,735 B2
(45) Date of Patent: Sep. 8, 2015

(54) METHOD OF CORRECTING VISION USING CORNEAL ONLAYS

(75) Inventors: Eugene de Juan, Jr., San Francisco, CA (US); Cary J. Reich, Los Gatos, CA (US); Stephen Boyd, Murrieta, CA (US); David Sierra, Aptos, CA (US); Jose D. Alejandro, Sunnyvale, CA (US)

(73) Assignee: Forsight Labs, LLC, Menlo Park, CA (US)

( * ) Notice: Subject to any disclaimer, the term of this patent is extended or adjusted under 35 U.S.C. 154(b) by 0 days.

(21) Appl. No.: 12/897,131

(22) Filed: Oct. 4, 2010

(65) Prior Publication Data

US 2011/0208300 A1    Aug. 25, 2011

Related U.S. Application Data

(63) Continuation of application No. PCT/US2009/039675, filed on Apr. 6, 2009.

(60) Provisional application No. 61/211,815, filed on Apr. 3, 2009, provisional application No. 61/119,712, filed on Dec. 3, 2008, provisional application No. 61/191,915, filed on Sep. 11, 2008, provisional application No. 61/050,147, filed on May 2, 2008, provisional application No. 61/050,106, filed on May 2, 2008, provisional application No. 61/042,594, filed on Apr. 4, 2008, provisional application No. 61/042,589, filed on Apr. 4, 2008.

(51) Int. Cl.
*A61F 2/14* (2006.01)
*A61F 9/00* (2006.01)

(52) U.S. Cl.
CPC ............... *A61F 2/145* (2013.01); *A61F 2/1451* (2015.04); *A61F 9/0017* (2013.01)

(58) Field of Classification Search
CPC ...... A61F 2/145; A61F 2/1451; A61F 2/1453; A61F 2/14; A61F 2/142; A61F 9/0017; A61F 2250/0056; A61F 2250/0091
USPC .......................... 623/5.11–5.16, 4.1; 606/107
See application file for complete search history.

(56) References Cited

U.S. PATENT DOCUMENTS

| | | | | | |
|---|---|---|---|---|---|
| 2,714,721 | A | * | 8/1955 | Stone, Jr. | 623/5.11 |
| 2,952,023 | A | * | 9/1960 | Rosen | 623/5.14 |
| 4,126,904 | A | * | 11/1978 | Shepard | 623/5.15 |
| 4,198,132 | A | * | 4/1980 | Seger et al. | 351/159.1 |
| 4,407,766 | A | * | 10/1983 | Haardt et al. | 264/2.2 |
| 4,715,858 | A | * | 12/1987 | Lindstrom | 623/5.13 |
| 4,772,283 | A | * | 9/1988 | White | 623/5.14 |
| 4,810,082 | A | * | 3/1989 | Abel, Jr. | 351/159.67 |
| 4,969,912 | A | * | 11/1990 | Kelman et al. | 128/898 |
| 4,994,081 | A | * | 2/1991 | Civerchia et al. | 606/107 |

(Continued)

*Primary Examiner* — Paul Prebilic
(74) *Attorney, Agent, or Firm* — Kilpatrick Townsend and Stockton LLP

(57) ABSTRACT

A corneal onlay is configured to adhere to the cornea so as to inhibit epithelial growth under the onlay. Structures can be provided on the onlay to adhere the onlay to the eye. At least one of an epithelial layer or the water inhibiting layer can be provided on or over the onlay, for example a natural epithelial layer or water inhibiting layer that inhibits, for example minimizes, water penetration into the onlay, so as to adhere the onlay to the eye with pumping of the endothelium. The water inhibiting layer may comprise a therapeutic covering positioned over the onlay to inhibit swelling of the cornea. The posterior surface of the onlay may be shaped so as to fit the anterior exposed surface of the cornea.

42 Claims, 45 Drawing Sheets

(56) References Cited

U.S. PATENT DOCUMENTS

| | | | | |
|---|---|---|---|---|
| 5,030,230 | A * | 7/1991 | White | 623/5.14 |
| 5,213,720 | A * | 5/1993 | Civerchia | 264/1.38 |
| 5,713,957 | A * | 2/1998 | Steele et al. | 623/5.16 |
| 6,055,990 | A * | 5/2000 | Thompson | 128/898 |
| 6,880,558 | B2 * | 4/2005 | Perez | 128/898 |
| 6,918,904 | B1 * | 7/2005 | Peyman | 606/5 |
| 2001/0047203 | A1 * | 11/2001 | Dalton et al. | 623/5.13 |
| 2002/0107567 | A1 * | 8/2002 | Terwee et al. | 623/6.12 |
| 2002/0151972 | A1 * | 10/2002 | Hughes | 623/4.1 |
| 2004/0141150 | A1 * | 7/2004 | Roffman et al. | 351/164 |
| 2004/0184158 | A1 * | 9/2004 | Shadduck | 359/665 |
| 2005/0238692 | A1 * | 10/2005 | Hughes | 424/427 |
| 2005/0259221 | A1 * | 11/2005 | Marmo | 351/160 R |
| 2006/0083773 | A1 * | 4/2006 | Myung et al. | 424/427 |
| 2006/0241751 | A1 * | 10/2006 | Marmo et al. | 623/5.11 |
| 2010/0036488 | A1 * | 2/2010 | de Juan et al. | 623/5.16 |

\* cited by examiner

ANTERIOR SIDE
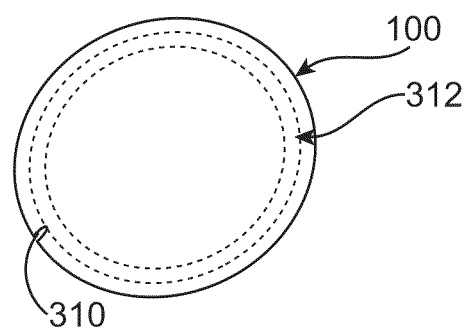
FIG. 3A1
POSTERIOR SIDE
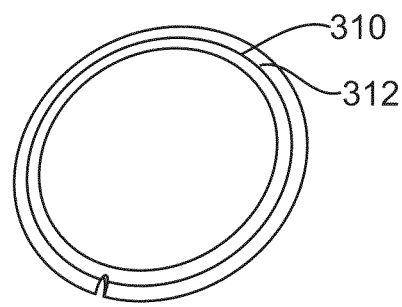
FIG. 3A2

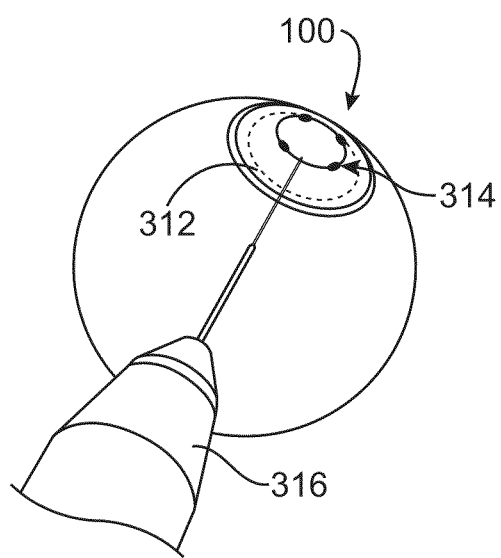
FIG. 3B1

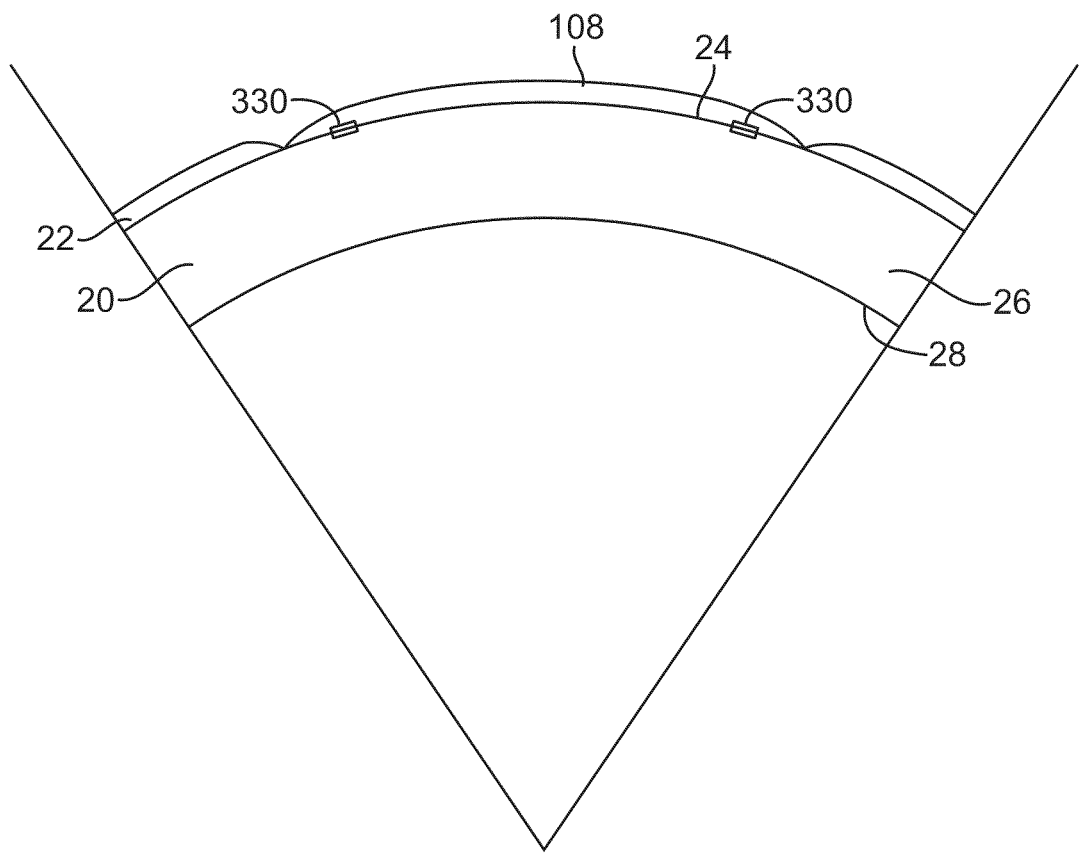
FIG. 3C
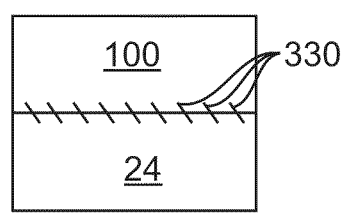
FIG. 3C1

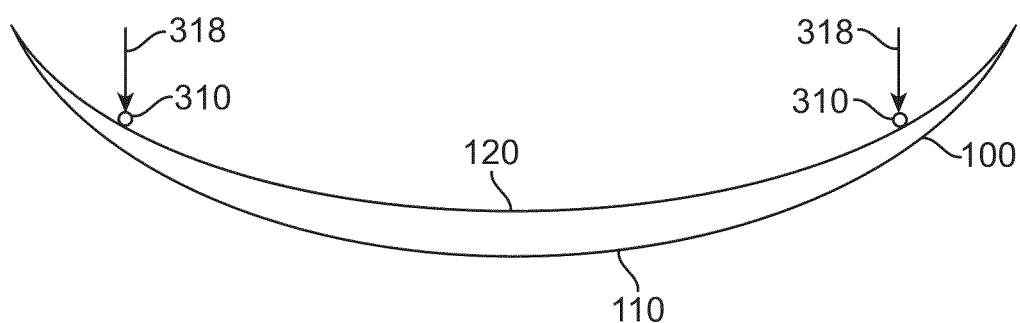
FIG. 3D
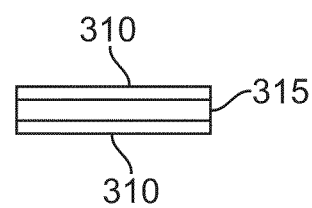
FIG. 3D1

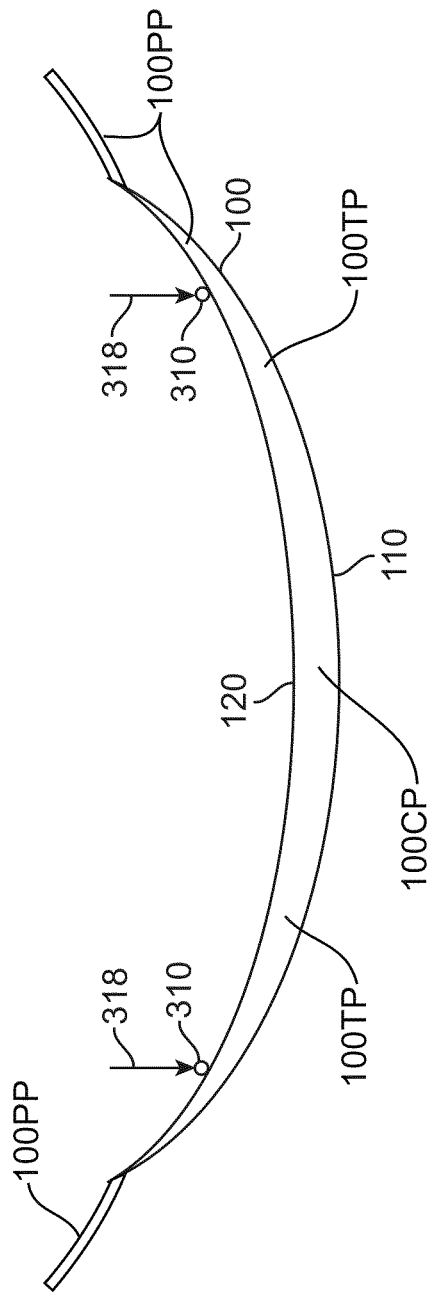
FIG. 3D2

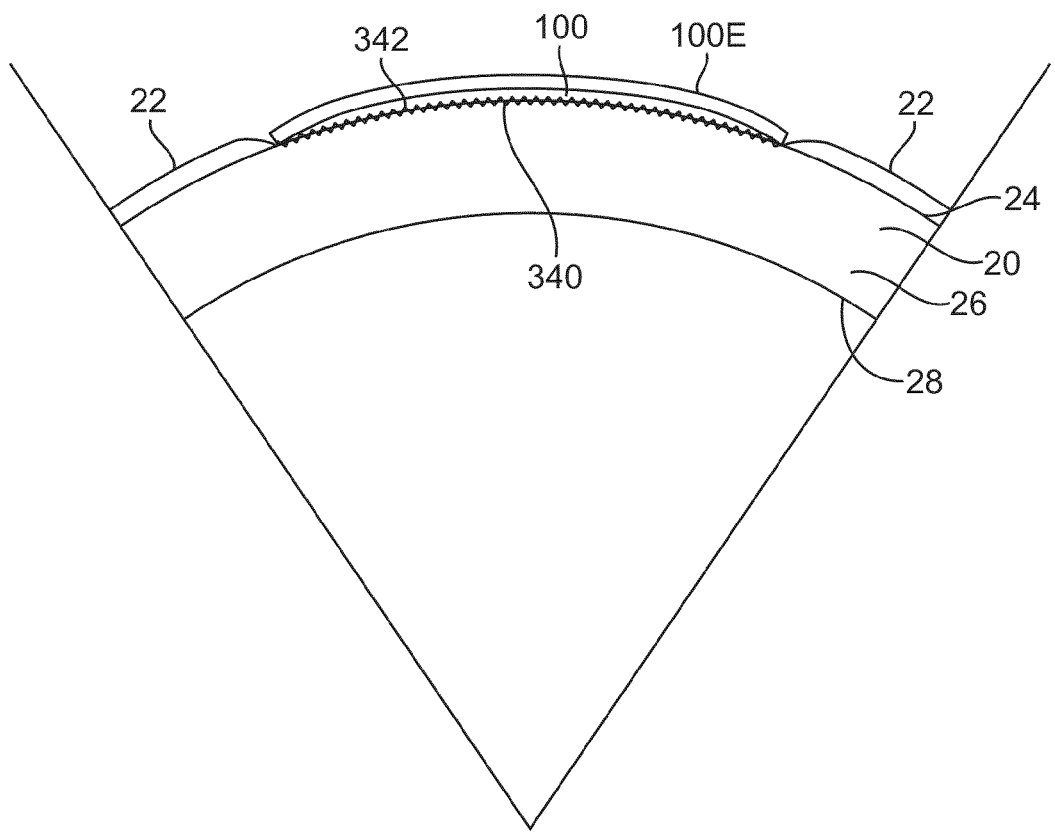
FIG. 3E
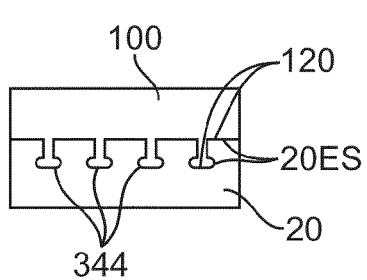
FIG. 3E1
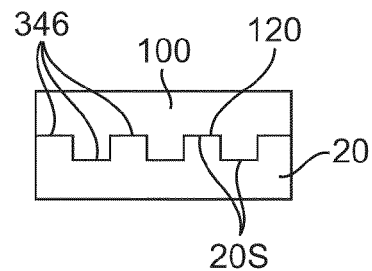
FIG. 3E2

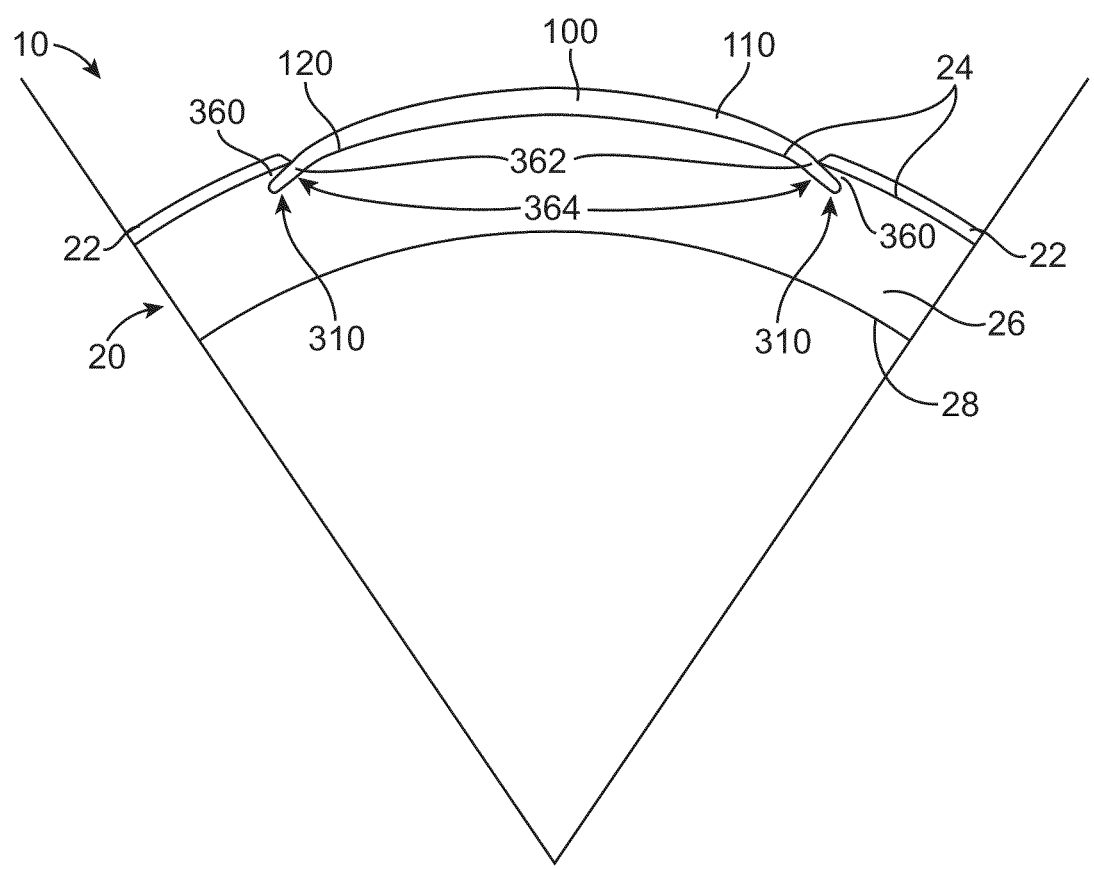
FIG. 3G1

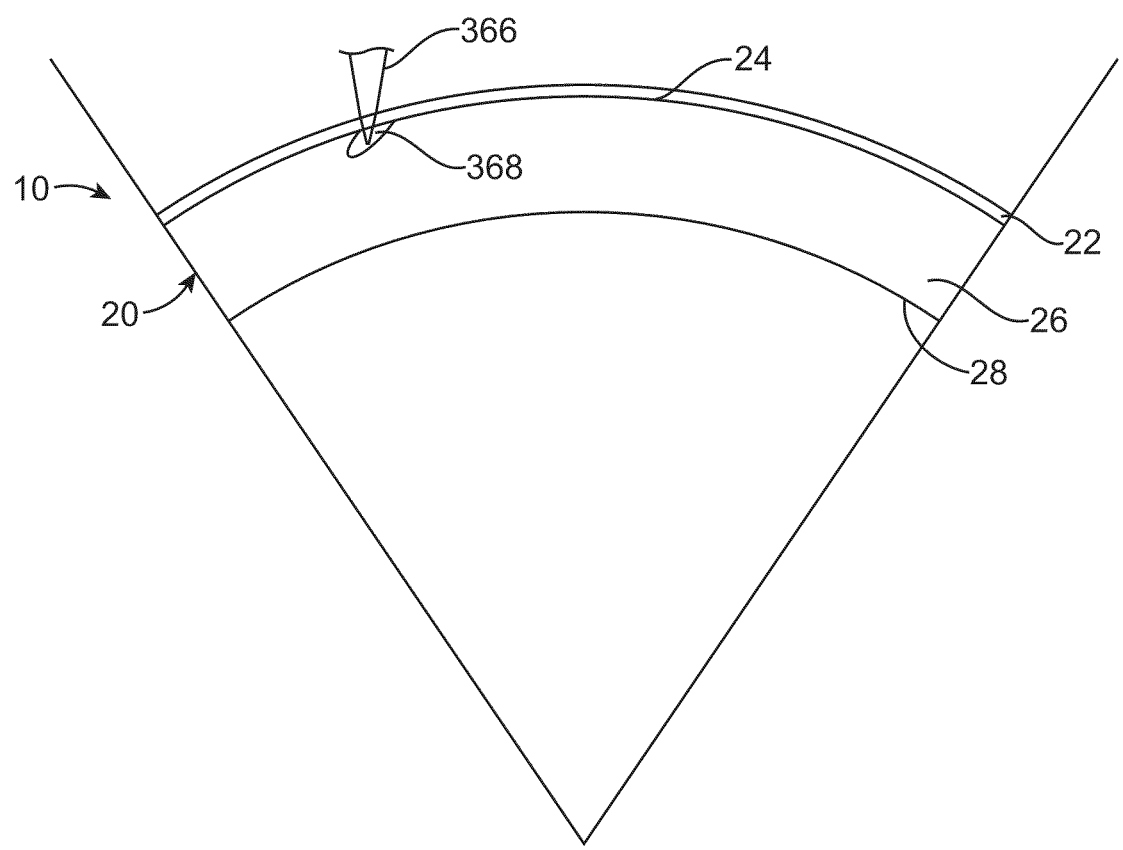
FIG. 3G2

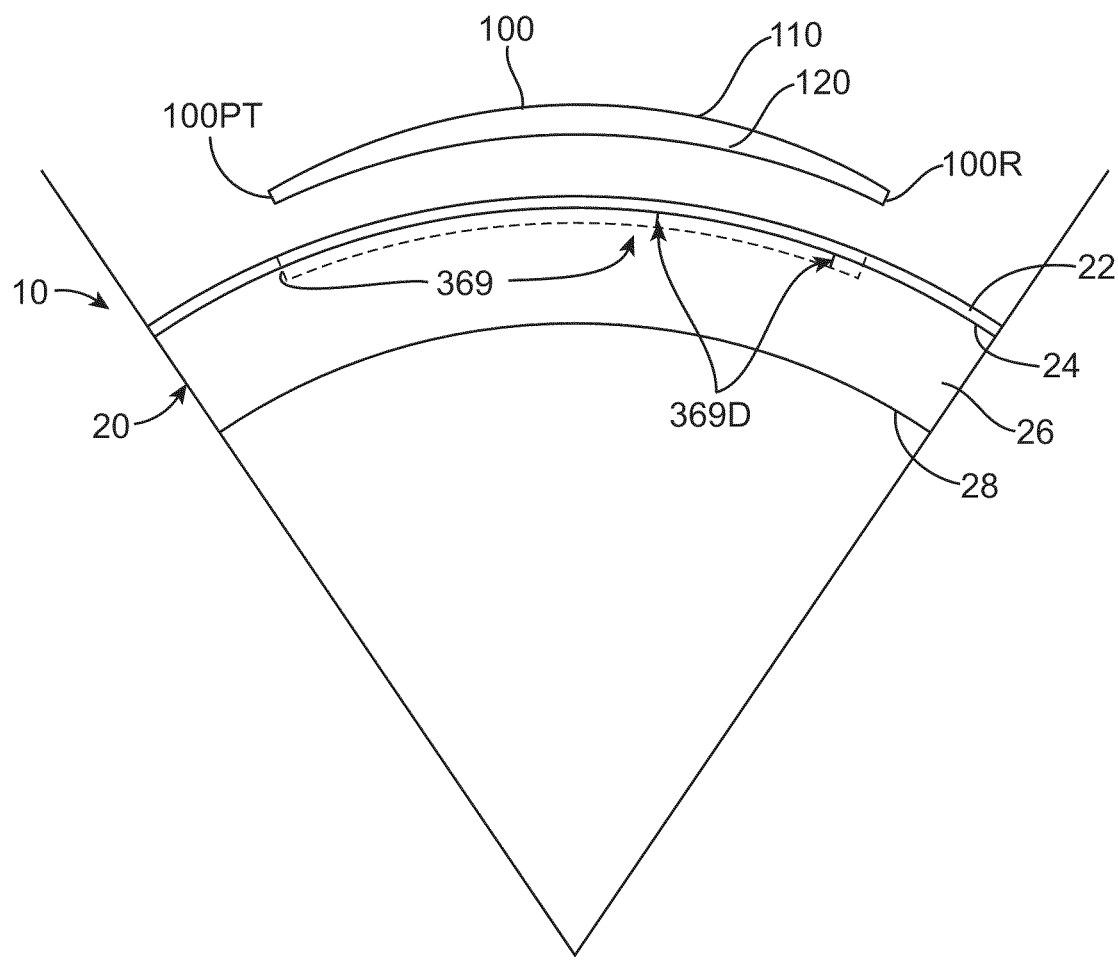
FIG. 3G3

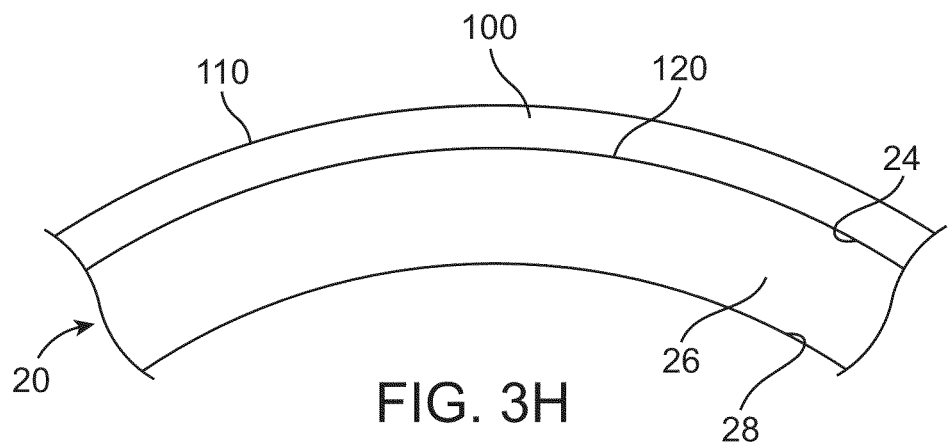
FIG. 3H
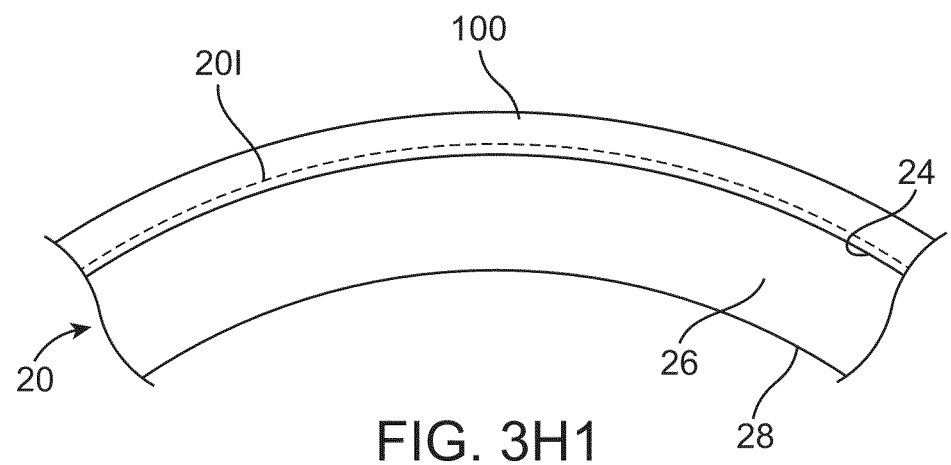
FIG. 3H1

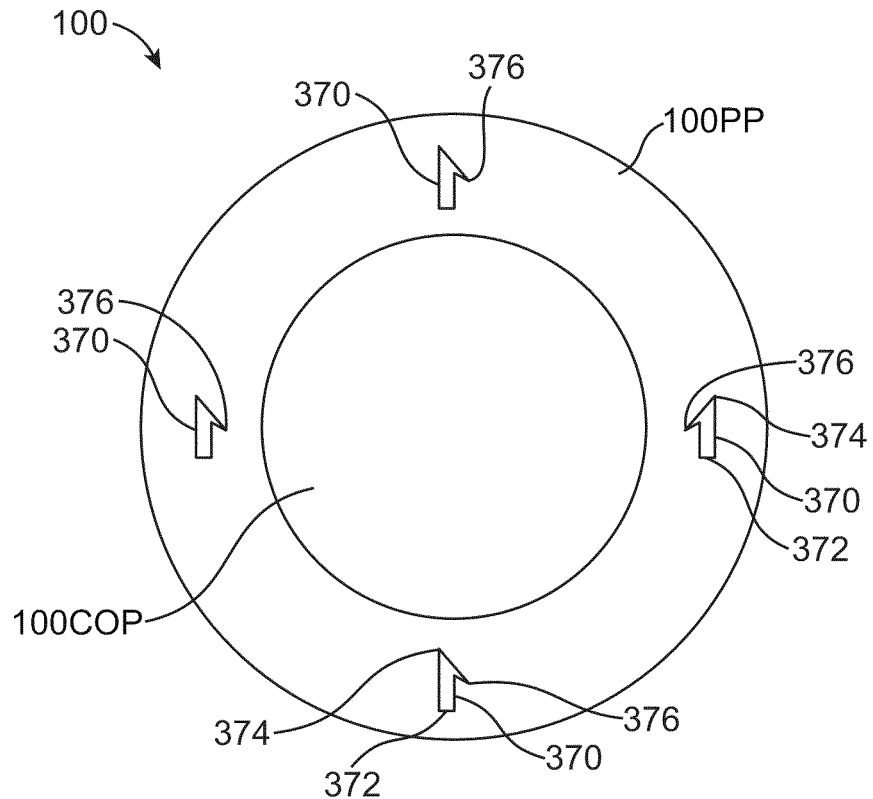
FIG. 3I1
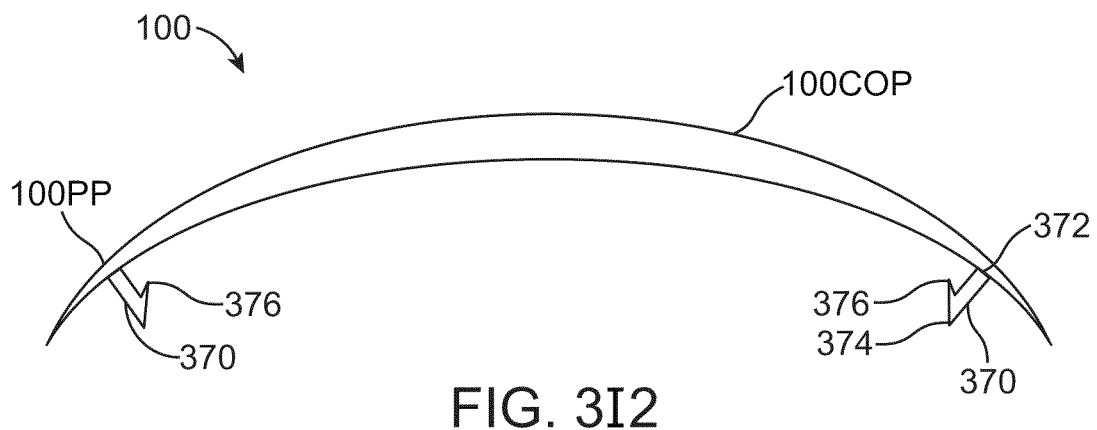
FIG. 3I2

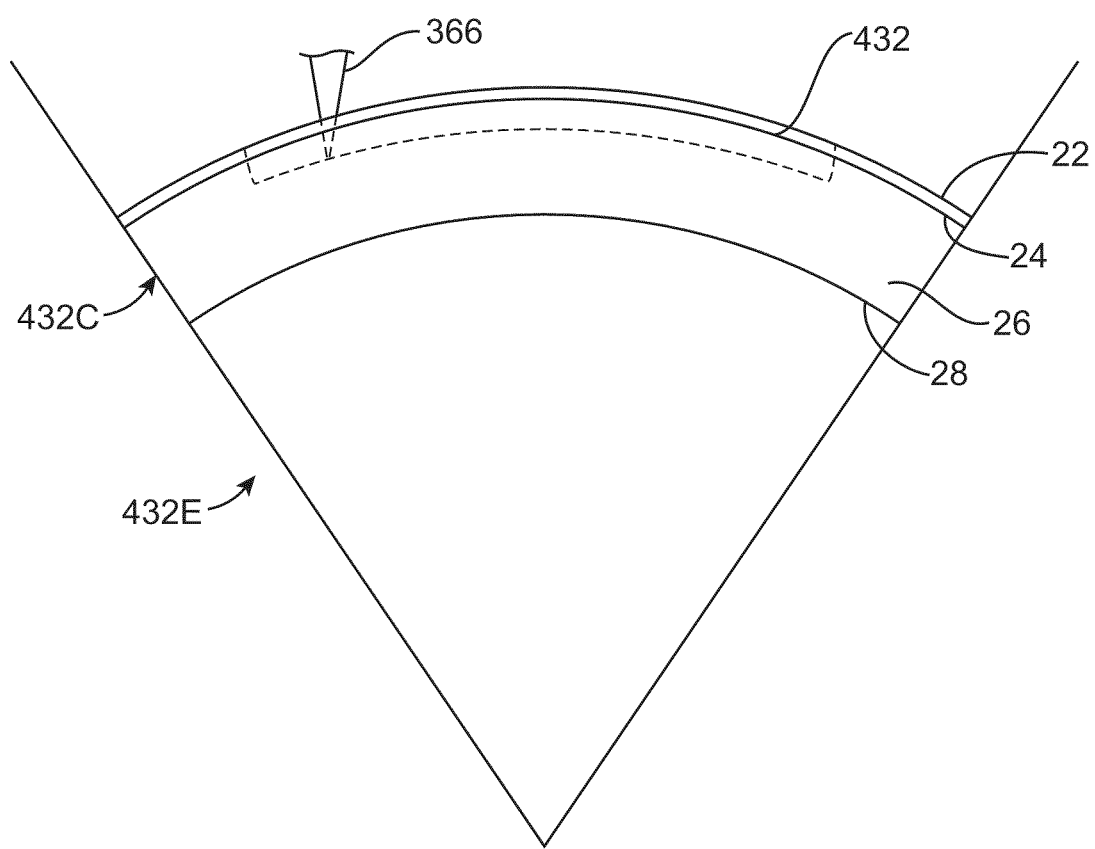
FIG. 4C1

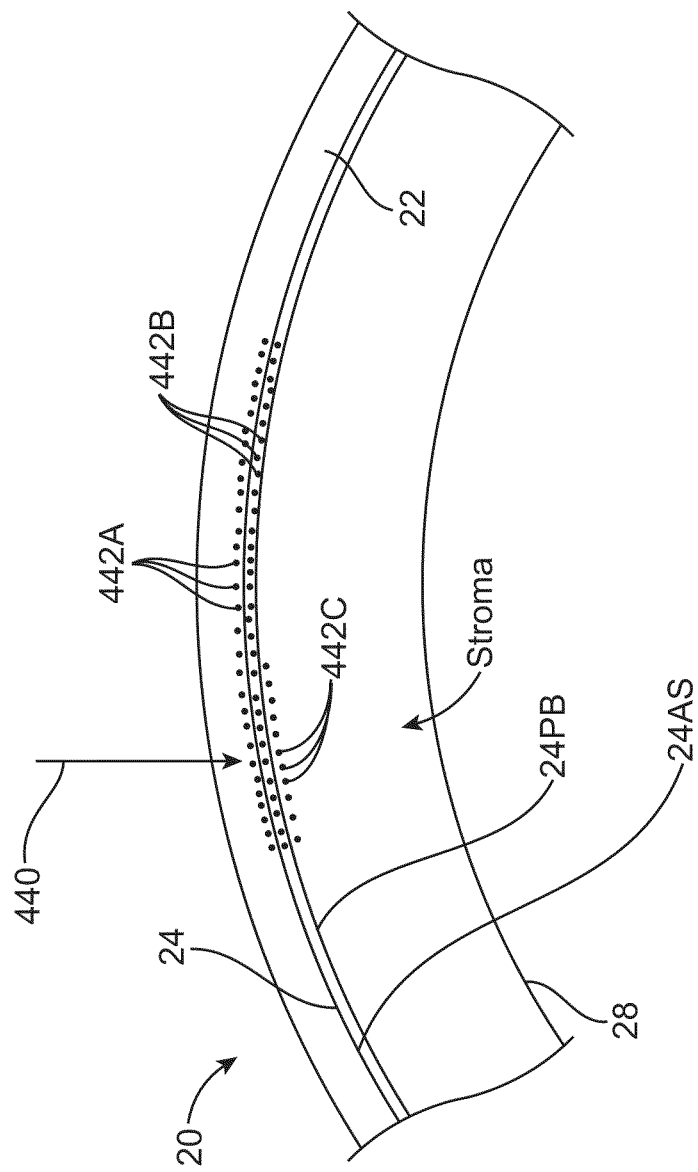

METHOD OF CORRECTING VISION USING CORNEAL ONLAYS

CROSS-REFERENCES TO RELATED APPLICATIONS

The present application is a Continuation of PCT/US2009/039675 filed Apr. 6, 2009, which application claims priority to U.S. Appln. Nos. 61/042,589 filed Apr. 4, 2008, entitled "CORNEAL ONLAY DEVICE AND METHODS,"; 61/050,106 filed May 2, 2008, entitled "CORNEAL ONLAY DEVICE AND METHODS,"; 61/042,594 filed Apr. 4, 2008, entitled "Therapeutic Device for Pain Management and Vision,"; 61/050,147 filed May 2, 2008, entitled "Therapeutic Device for Pain Management and Vision,"; 61/191,915 filed Sep. 11, 2008, entitled "Therapeutic Device for Pain Management and Vision"; 61/119,712 filed Dec. 3, 2008, entitled "Therapeutic Device for Pain Management and Vision"; and 61/211,815 filed on Apr. 3, 2009, entitled "Therapeutic Device for Pain Management and Vision"; the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

1. Field of the Invention

The present invention is generally directed to correction of refractive error and/or aberrations of the eye. Although specific reference is made to corneal onlays placed on an eye, embodiments of the present invention can be used in many applications where a lens is fabricated and/or adhered to tissue.

The eye includes several tissues that allow patients to see. The eye generally includes a cornea, a lens and a retina. The cornea and lens focus light on the retina so as to form an image that can be perceived by the patient. The cornea of the eye is an anterior tissue of the eye that is clear in healthy eyes. The lens is disposed posterior to the cornea and can also focus light to allow a patient to see. The aqueous humor is a fluid disposed between the cornea and lens. The retina is disposed posterior to the lens and includes many photo receptors to sense an image formed on the retina by the cornea and lens.

Many patients suffer from some form of optical defect of the eye. Commonly known optical defects of the eye include refractive errors such as nearsightedness, also referred to as myopia, far sightedness, also referred to as hyperopia, and astigmatism. In addition, many eyes have some level of higher order aberration such as coma, and spherical aberration. These higher order aberrations can be measured with optical systems such as wavefront systems, and may affect vision in some patients, for example with large pupil sizes at night.

Work in relation to embodiments of the present invention suggests that current techniques to correct optical defects of the eye may be less than ideal in at least some instances. Eyeglasses and contact lenses may not be suitable for some patients, and in many instances may not correct higher order aberrations of the eye. For example, eyeglasses can be difficult for active patients to wear. In at least some instances, contact lenses may cause irritation of the eye. Many of the current surgical methodologies involve cutting and/or removal of tissue. In at least some instances, this cutting and removal of tissue may weaken the eye and limit the size of optical correction on the eye. In at least some patients, the size of optical correction may be smaller than the pupil at night, such that aberrations may be induced by the surgery that is intended to correct vision of the eye. Examples of surgeries that cut and/or remove tissue include photorefractive keratectomy (hereinafter "PRK") and laser assisted in situ keratomileusis (hereinafter "LASIK").

One approach that provides an optical correction by adding material to the eye is to place a lens on or in the cornea of the eye, referred to as corneal onlays and corneal inlays, respectively. Corneal onlay generally refers to a lens placed on the eye under an epithelial layer and/or on an exposed surface after the epithelial layer has been removed. In human patients with normal eyes the exposed tissue layer under the epithelium is referred to as Bowman's membrane. With corneal onlays in human patients with normal eyes, the corrective lens can be placed on Bowman's membrane after removal of the corneal epithelium. In human patients who have undergone PRK and some animals, the layer of tissue exposed with removal of the epithelium can include corneal stroma, and an onlay positioned on such patients can be positioned on corneal stroma.

Although corneal onlays may provide some advantages over current methodologies that remove tissue, work in relation to embodiments of the present invention suggests that current corneal onlays may be less than ideal. One problem that may occur with corneal onlays in some instances is that epithelial tissue may grow under the onlay so as to dislodge the onlay from the eye. Many patients would like to receive correction of wavefront aberrations of the eye. Wavefront correction that may require that the onlay lens have a complex shape on the eye that is within a few microns, or less, of the intended shape. At least some of the current methodologies of fabricating and placing corneal onlays on the eye may not be able to consistently provide complex shapes on the eye with the required accuracy for all patients. Because of the above potential short comings of corneal onlays and current refractive surgeries, at least some patients may receive a correction that is less than ideal.

In light of the above, it would be desirable to provide improved treatments for epithelial defects of the cornea. Ideally, these treatments would avoid at least some of the deficiencies of known techniques while providing improved patient vision.

2. Description of the Background Art

The following patents and publications may be relevant to the present application U.S. Pat. Nos. 4,126,904; 4,268,131; 4,346,482; 4,452,776; 4,452,925; 4,563,779; 4,581,030; 4,612,912; 4,624,669; 4,676,790; 4,693,715; 4,715,858; 4,799,931; 4,810,082; 4,834,748; 4,851,003; 4,923,467; 4,973,493; 4,979,959; 4,983,181; 4,994,081; 5,019,097; 5,108,428; 5,112,350; 5,114,627; 5,156,622; 5,163,596; 5,171,318; 5,192,316; 5,196,027; 5,213,720; 5,244,799; 5,263,992; 5,292,514; 5,401,508; 5,489,300; 5,522,888; 5,552,452; 5,713,957; 5,716,633; 5,836,313; 6,055,990; 6,090,995; 6,454,800; 6,544,286; 6,607,522; 6,645,715; 6,689,165; 6,702,807; 6,880,558; 7,004,953; 7,077,839; 7,229,685; US2004/0170666; US2005/028723; US2006/0034807; US2006/013050; US2006/0134170; US2006/0246113; and US2007/002046.

BRIEF SUMMARY OF THE INVENTION

The present invention is generally directed to correction of refractive error and/or aberrations of the eye. Although specific reference is made to corneal onlays placed on an eye, embodiments of the present invention can be used in many applications where a lens is fabricated and/or adhered to tissue.

In many embodiments, improved tissue adhesion inhibits, for example minimizes, and may even avoid, epithelialization under the onlay. In some embodiments, structures can be provided on the eye and/or the onlay to adhere the onlay to the exposed recipient corneal tissue. The adhesion may comprise suction of a water inhibiting material or water inhibiting layer that inhibits swelling of the cornea when the cornea is sealed with the water inhibiting material. At least one of an epithelial layer or the water inhibiting layer can be provided on or over the onlay, for example a natural epithelial layer or water inhibiting layer that inhibits or minimizes water penetration into the onlay, so as to adhere the onlay to the eye with pumping of the endothelium. The water inhibiting layer may comprise an erodible biomaterial disposed on the onlay and configured to degrade such that the water inhibiting layer degrades when the epithelium covers the onlay. A therapeutic covering may comprise the water inhibiting layer. The therapeutic covering that can be positioned over the onlay so as to suck down onto the cornea to inhibit swelling of the cornea and adhere the onlay to the cornea, and the covering can be removed when the epithelium has regenerated. The posterior surface of the onlay may be shaped so as to fit the anterior exposed surface of the cornea.

The therapeutic covering may comprise an inner portion shaped with the optical correction and an outer portion configured to conform to irregularities of the cornea so as to form a seal against the corneal epithelial tissue. The inner portion can be more rigid than the outer portion, such that the inner correction retains the optical shape when the outer portion deforms to the irregularities of the cornea. A therapeutic covering comprising a water inhibiting layer to substantially inhibit water passed through the covering into the cornea. The water inhibiting layer can form a seal with the corneal epithelium so as to inhibit swelling of the cornea when the epithelium regenerates. The water inhibiting layer can substantially decrease edema after surgery, which can increase recovery of visual acuity, decrease pain and improve adherence of the onlay.

In many embodiments, improved fabrication of onlays can provide complex onlay shapes on the cornea of the eye, for example with a jet deposition process and/or ablation of the onlay. The complex shapes can be formed in response to wavefront aberration of the eye and/or refraction of the eye such as manifest refraction.

The onlay may be composed of a biocompatible material, for example a biocompatible material that allows innervation with corneal nerves when the onlay is disposed on the eye.

In a first aspect, embodiments of the present invention provide a corneal onlay for placement on an exposed surface of a cornea of an eye to correct vision of the eye. The onlay comprises a lens, in which the lens comprises an optically transmissive material, and the lens is configured to adhere to the cornea.

In many embodiments, the optically transmissive material comprises at least one of a donor cornea material, a human donor cornea material, an artificial human cornea material, an innervated artificial human cornea material, a xenograft cornea material, a porcine cornea material, or a lyophilized xenograft cornea material.

In many embodiments, the optically transmissive material comprises at least one of a collagen based material, a human recombinant material, a fibrogen material, a collagen plus polymer material, a neoglycopolymer crosslinked polymer matrix material, a biosynthetic matrix material, a collagen hydrogel, material a collagen PEA hydrogel material, a collagen acrylate material, a muco adhesive or a polysaccharide multiarm glue.

In many embodiments, the optically transmissive material comprises at least one of a plastic material, a hydrogel material, or an acrylate material.

In many embodiments, the lens is configured to adhere to a Bowman's membrane and/or a stroma with covalent bonding of the lens to the Bowman's membrane and/or the stroma.

In many embodiments, the onlay comprises at least one of a glue, a bi-functional cross-linking agent, a multi-functional cross-linking agent to covalently bond the lens to the stroma and/or Bowman's. The at least one of the bifunctional agent or the multifunctional agent may comprise at least one of glutaraldehyde or PEG.

In many embodiments, the lens is configured to adhere to a Bowman's membrane and/or a stroma with mechanical adhesion. For example, a glue can be configured for mechanical adhesion of the onlay to the stroma and/or the Bowman's membrane.

In many embodiments, the lens comprises a peripheral portion configured for surgical tucking into the stroma and/or the Bowman's membrane.

In many embodiments, peripheral portion comprises an adhesive. For example, the peripheral portion may comprise a photosensitizer to weld the peripheral portion to the stroma and/or the Bowman's membrane.

In many embodiments, the lens is configured to stabilize from a liquid to a solid and/or adhere to the cornea with a protein cross-linking agent.

In many embodiments, the lens is configured to stabilize from a liquid to a solid and/or adhere to the cornea with photoactivated cross-linking agent. The photoactivated cross-linking agent may be capable of activation with at least one of UV light, blue light, visible light, or infrared light. The photoactivated cross-linking agent may comprise a heterobifunctional cross-linking agent with a photoactivated group. The photoactivated cross-linking agent may comprise at least one of riboflavin, indocyanine green, Janus green, rose Bengal or methylene blue.

In many embodiments, an adhesive disposed on a posterior surface of the lens to adhere the lens to the cornea. The adhesive may comprise a glue. The glue may comprise at least one of fibrin, polyethylene glycol, albumin, cyanoacrylate, methylmethacrylate, modified protein with an activated functional group, succinylated collagen, or a polysaccharide multi-arm.

In many embodiments, the adhesive comprises a photoactive tissue welding agent. The photoactive tissue welding agent may comprise at least one of riboflavin, indocyanine green, Janus green, rose Bengal, or methylene blue. The photoactive tissue welding agent can be responsive to at least one of UV light, blue light, visible light or infrared light.

In many embodiments, the adhesive comprises a protein cross liking agent. The protein cross-linking agent may comprise a heterobifunctional with a photoactivated group and a cross-linking group.

In many embodiments, the lens comprises a central portion to correct the vision of the eye and a peripheral portion to adhere the lens to the cornea, in which the adhesive is disposed on the peripheral portion to at least one of inhibit or minimize interference of the adhesive with the vision of the eye. The peripheral portion may comprises an annular shape, and the adhesive can be disposed on the annular shape. The adhesive can be disposed on the peripheral portion with at least one of a sheet, a drop, a ring or a spray.

In many embodiments, the adhesive is configured to at least one of inhibit or minimize epithelialization along the posterior surface. For example, the adhesive may comprise a compound reactive with the epithelium so as to inhibit epithelialization along the posterior surface between the posterior surface and a Bowman's membrane of the cornea.

In many embodiments, the posterior surface comprises an agent to inhibit epithelialization along the posterior surface. For example, the lens may comprise an anterior surface without an agent to inhibit epithelialization so as to promote epithelialization along the anterior surface.

In many embodiments, the lens has been molded with a mold prior to placement on the exposed surface of the cornea.

In many embodiments, the lens comprises an ablatable material suitable for ablation when the lens is adhered to a surface of the cornea.

In many embodiments, the lens comprises a shape to correct aberrations of the eye in response to a wavefront aberration measurement of the eye.

In many embodiments, the lens comprises an anterior surface profile formed with stereolithography.

In many embodiments, the lens comprises an anterior surface and an agent to promote epithelialization along the anterior surface. The agent to promote epithelialization may comprise at least one of fibronectin, tethered enhancer molecules, a photochemically reactive group, or an amino acid sequence to promote binding of the GPIIB/IIIA cell receptor binding. The amino acid sequence to promote binding of the GPIIB/IIIA cell receptor binding may comprise an RGD amino acid sequence.

In many embodiments, the lens comprises an anterior surface and structure on the anterior surface to promote epithelialization along the anterior surface. The structure to promote epithelialization may comprise at least one of indentations, protrusions or castellation.

In many embodiments, the lens comprises an anterior surface and epithelial cells on the anterior surface to promote epithelialization along the anterior surface. The epithelial cells on the lens may comprise epithelial cells adhered to the lens and grown on the lens prior to placement to adhere the cells to the lens. The epithelial cells on the lens may comprise epithelial seed epithelial cells.

In many embodiments, the lens comprises a central optical portion to correct vision and a peripheral portion with indicia to align the lens with the eye.

In many embodiments, the optically transmissive material is capable of receiving corneal nerve fibers grown into the material to innervate the lens.

In many embodiments, the layer comprises at least one of a synthetic adhesive, a natural and/or biologically derived adhesive, a recombinant adhesive or a hybrid adhesive or derivatives thereof. The synthetic adhesive may comprise a least one of a polylysine adhesive, a cyanoacrylate adhesive or a polyethylene glycol adhesive or derivative thereof. The natural and/or biologically derived adhesive may comprise at least one of a fibrin adhesive or an RPG adhesive or derivatives thereof. The recombinant adhesive may comprise at least one of a fibrin adhesive, a polylysine adhesive, a biologically derived adhesive from plasma or an RPG adhesive or derivatives thereof. The hybrid adhesive may comprise an albumin with glutaraldehyde adhesive.

In many embodiments, the onlay comprises at least one of an antibiotic, a steroid, a non-steroidal anti-inflammatory (hereinafter "NSAID"), an analgesic or an anesthetic.

In many embodiments, the onlay comprises a therapeutic agent and the therapeutic agent comprises at least one of at least one of an analgesic, an anti-inflammatory, an antibiotic, a non-steroidal anti-inflammatory, a steroid or an epithelial growth factor to enhance epithelialization. The analgesic may comprises at least one of proparacaine, lidocaine, or tetracaine or a derivative thereof. The antibiotic may comprise tobramycin or a derivative thereof. The non-steroidal anti-inflammatory may comprise at least one of diclofenac, nepafenac, or suprofen or a derivative thereof. The steroid may comprise at least one of fluorometholone, dexamethasone or prednisolone or a derivative thereof. The growth factor may comprise at least one of fibroblast growth factor, fibronectin, or arginine glycine aspartic acid (RGD) comprising peptide sequence or a derivative thereof.

In many embodiments, the onlay comprises a muco-adhesive configured to release therapeutic agent.

In many embodiments, the onlay is configured to adhere to the cornea with at least one tack disposed on a peripheral portion of the onlay. The at least one peripheral tack may comprise a bioerodable material configured to erode when the epithelium has grown over the onlay. The at least one peripheral tack may comprise at least one of an inwardly inclined tack, an outwardly inclined tack, a suture or a barb.

In another aspect embodiments of the present invention provide a corneal onlay lens for placement on a cornea of an eye to correct vision of the eye. The onlay comprises a lens, in which the lens comprises biocompatible material, and the lens is configured to adhere to the cornea with at least one of the epithelium or a water inhibiting material disposed over the lens. The lens may be configured to adhere to the cornea without an adhesive. The at least one of the epithelium or the water inhibiting material may comprise the water inhibiting material, or the epithelium, or both.

In many embodiments, the water inhibiting material comprises a degradable material. The degradable material can be configured to degrade when epithelium is positioned over the onlay. The degradable material can be configured to degrade within about one week of placement on the cornea, for example within about 4 days so as to correspond with re-epithelialization of the cornea. The degradable material may comprise at least one of poly lactic acid (PLA), poly glycolic acid (PGA) or PLA/PGA copolymer. For example, the hydrophobic bioerodable material may comprise a degradable hydrophobic suture material configured to degrade in less than about one week and disposed on the anterior surface of the onlay to inhibit water.

In many embodiments, the lens comprises an anterior water inhibiting layer, and a posterior water permeable layer with a posterior surface shaped to fit an anteriorly exposed surface of the cornea, such that the lens is configured to adhere to the cornea in response to a pumping of water from the cornea with an endothelium of the cornea. For example, the anterior water resistant layer may comprise an epithelial layer and the posterior water permeable layer may comprise a stromal layer, in which the posterior surface and the anteriorly exposed surface of the cornea each comprise laser micromachined structures to connect the posterior surface with the anteriorly exposed surface.

In many embodiments, the lens comprises a posterior surface and the cornea comprises an anteriorly exposed surface of a Bowman's membrane and/or a stroma and wherein the posterior surface and the anteriorly exposed surface each comprise interlocking structures to attach the posterior surface of the lens to the anteriorly exposed surface.

In many embodiments, the lens comprises a posterior surface and the cornea comprises an anteriorly exposed surface of a Bowman's membrane and/or a stroma, and the posterior surface comprises a first charge and the anteriorly exposed surface comprises a second charge, and wherein the first charge is opposite from the second charge to attach the posterior surface of the lens to the anteriorly exposed surface.

In many embodiments, the lens comprises a peripheral portion to attach the lens to the cornea and a central optical portion and wherein the peripheral portion comprises structures to attach to at least one of a peripheral cut or a peripheral abrasion of the cornea.

In many embodiments, the material is configured to integrate with at least one a Bowman's membrane and/or a stroma of the cornea along the posterior surface of the lens so as to adhere the lens to the Bowman's membrane and/or the stroma.

In another aspect embodiments of the present invention provide a method of correcting vision with a corneal onlay lens on a surface of a cornea of an eye. A lens comprising an optically transmissive material is shaped in situ on the surface of the cornea, in which the lens is adhered to the surface of the cornea.

In many embodiments, the lens is molded in situ on the surface of the cornea and the surface comprises at least one of a Bowman's membrane and/or a stroma.

In many embodiments, the lens is deposited with a jet deposition process in situ on the surface of the cornea and wherein the surface comprises at least one of a Bowman's membrane and/or a stroma.

In many embodiments, the jet deposition process is configured to apply microparticles of the optically transmissive material to the exposed surface to form the lens in situ.

In many embodiments, the optically transmissive material comprises collagen applied to the eye from a cartridge.

In many embodiments, the jet deposition process comprises a first cartridge comprising a first component and a second cartridge comprising a second component and wherein the first component and the second component are applied sequentially to form the lens.

In many embodiments, the jet deposition process deposits components of the optically transmissive lens material over time to form the lens in situ on the exposed surface.

In many embodiments, the jet deposition process comprises sputtering at least one component of the optically transmissive material on the exposed surface.

In many embodiments, the jet deposition process comprises computer control to deposit at least one component of the optically transmissive material so as to form a customized shape.

In another aspect, embodiments provide an apparatus to form a lens on an exposed surface. At least one jet forming structure is configured to form a jet. At least one cartridge is coupled to the at least one jet forming structure, and the at least one cartridge comprises at least one material component of the lens. The jet forming structure is configured to deliver the at least one material to the exposed surface to form the lens.

In another aspect, embodiments of the present invention provide a deposition process to form a lens in a cornea of an eye, the cornea comprising an epithelium and a Bowman's membrane and/or a stroma. A material is applied to the cornea so as to penetrate the epithelium and deposit the material in or on the Bowman's membrane and/or the stroma and wherein the material is deposited over time to form the lens in or on the Bowman's membrane and/or the stroma. The lens can be removed with at least one of ultrasound and/or laser radiation. The material may comprise an optically transmissive material. The process may comprise a tattoo deposition process.

In another aspect, embodiments of the present invention provide a method of adhering an onlay on a cornea. The onlay is adhered to a surface of the cornea with Van der Waals forces.

In another aspect, embodiments of the present invention provide a corneal onlay for placement on an exposed Bowman's membrane and or cornea. A lens comprises an anterior surface and a posterior surface, in which the posterior surface comprises nano-structures to adhere the onlay to the cornea Van der Waals forces.

In another aspect, embodiments of the present invention provide a method of adhering an onlay on a cornea. The anterior surface of the cornea is sealed with the onlay so as to adhere the onlay to the cornea with endothelial pumping of water from the cornea.

In another aspect, embodiments of the present invention provide a method of adhering an onlay on a cornea. The anterior surface of the cornea is sealed with the onlay so as to adhere the onlay to the cornea with suction.

In many embodiments, the suction comprises water suction.

In another aspect, embodiments provide a method of adhering an onlay on a cornea, in which the cornea comprises a stroma and/or a Bowman's membrane. A peripheral portion of the stroma and/or the Bowman's membrane is cut and/or excised. A peripheral portion of the onlay is inserted into the peripheral portion.

In many embodiments, the peripheral portion is of the stroma and/or the Bowman's membrane is ablated with a laser beam comprising at least one of an excimer laser beam or a femtosecond laser beam to cut and/or excise the peripheral portion of the stroma and/or the Bowman's membrane.

In many embodiments, the peripheral portion is of the stroma and/or the Bowman's membrane is ablated with a laser beam comprising at least one of an excimer laser beam or a femtosecond laser beam to cut and/or excise the peripheral portion of the stroma and/or the Bowman's membrane.

In many embodiments, peripheral portion of the stroma and/or the Bowman's membrane is cut so as to form a flap and wherein the peripheral portion of the onlay is tucked under the flap.

In many embodiments, an adhesive is cured to adhere the peripheral portion of the onlay to the peripheral portion of the stroma and/or the Bowman's membrane.

In many embodiments, the peripheral portion of the stroma and/or the Bowman's is irradiated with a light beam to adhere the peripheral portion of the contact lens to the peripheral portion of the stroma and/or the Bowman's.

In many embodiments, the peripheral portion of the stroma and/or the Bowman's is irradiated with a laser light beam to weld the peripheral portion of the stroma and/or the Bowman's. The onlay can be aligned with the eye before the peripheral portion of the stroma and/or the Bowman's is irradiated with the light beam.

In another aspect, embodiments provide a method of treating a keratoconus of a cornea of an eye, in which the cornea comprises an epithelium and a Bowman's membrane and/or a stroma. At least a central portion of the epithelium is removed to expose an anterior surface of the Bowman's membrane and/or the stroma. A corneal onlay is adhered to the exposed anterior surface of the Bowman's membrane and/or the stroma.

In another aspect, embodiments provide an onlay to treat a cornea of the eye, in which the cornea comprising an epithelium and a Bowman's membrane and/or a stroma. The onlay comprises a first portion, a second portion an a third portion.

The first portion is configured to correct an optical defect of the eye. The second portion is configured to adhere a to a conjunctiva of the eye. The third portion extends from the second potion to third portion so as to anchor the onlay to the conjunctiva.

In another aspect, embodiments provide a system to correct vision of an eye having a cornea, the cornea comprising a stroma and/or a Bowman's membrane under an epithelium. The system comprises an onlay and a covering. The onlay is configured to correct vision when positioned on the stroma and/or the Bowman's membrane. The covering comprises a layer of a water impermeable material positionable over the onlay on the stroma and/or Bowman's membrane of the eye.

In many embodiments, the covering is configured to inhibit swelling of the cornea. The layer can be configured to inhibit swelling of the cornea for a plurality of days cornea when positioned on the eye over the onlay. The layer can be configured to minimize swelling of the cornea for the plurality of days.

In many embodiments, the layer is configured to conform to irregularities of the cornea to inhibit the swelling.

In many embodiments, a hydrophobic material is disposed along a lower surface of the covering to adhere to the cornea and wherein a hydrophilic material is disposed along an upper surface of the covering to contact a tear liquid of the eye.

In many embodiments, the layer is configured for the eye to view through the layer for a plurality of days when positioned over the onlay on the eye.

In many embodiments, the layer is configured to adhere to the epithelium for a plurality of days. The therapeutic covering can be configured to separate from the epithelium such that the epithelium remains on the onlay and the Bowman's and/or stroma. The layer may be configured to separate from the epithelium with a removal agent.

In many embodiments, the layer is configured to provide functional vision for the eye when the epithelium has a defect.

In many embodiments, the layer is configured to enhance the optical properties of the cornea when the epithelium heals over the onlay.

In another aspect, embodiments provide a system to correct vision of an eye having a cornea, in which the cornea comprises a stroma and/or a Bowman's membrane. An onlay is configured to correct vision when positioned on the stroma and/or Bowman's membrane. A covering comprises at least one layer of a therapeutic material, covering is positionable over onlay to inhibit water flow to the stroma and/or the Bowman's membrane.

In many embodiments, an epithelium and a tear liquid are disposed over the stroma and/or the Bowman's membrane and wherein the at least one layer is configured to inhibit water flow from the tear liquid of the eye to the stroma and/or Bowman's membrane.

In many embodiments, the at least one layer is configured to decrease swelling of the cornea to within about 5% of a thickness of a pre-operative value of the cornea. For example, the at least one layer can be configured to decrease swelling of the cornea to within about 2.5% of a thickness of a pre-operative value of the cornea.

In many embodiments, the at least one layer comprises at least one of a solid, an adhesive, a gel, a low adhesion gel or a liquid.

In many embodiments, the at least one layer comprises a lower surface configured to adhere to the onlay. The lower surface may comprise a hydrophobic material to adhere to the cornea. For example, the lower surface can be configured to adhere to the epithelium with the hydrophobic material.

In many embodiments, the at least one layer comprises a hydrophilic upper surface configured to contact the tear liquid of the eye.

In many embodiments, an anterior refracting surface is disposed on the at least one layer to correct vision of the eye.

In many embodiments, the therapeutic material comprises a bio-compatible material configured to detach the lower surface from the onlay when the epithelium regenerates.

In many embodiments, the at least one layer comprises a lens. The lens may comprise an upper surface, the upper surface may be curved and configured to contact the tear liquid, and the upper surface may comprise a curvature so as to correspond to a curvature of an anterior surface of the onlay to within about +/−1 Diopter. The at least one layer may comprise a lower surface configured to contact the onlay, in which a thickness of the at least one layer from the lower surface to the upper surface is uniform to within about +/−10 microns so as to correspond to the curvature of an anterior surface of the onlay.

In many embodiments, the therapeutic material comprises an optically clear material configured to transmit light.

In another aspect, embodiments provide a system to correct vision of an eye of a patient, in which the eye comprises a cornea. An onlay is configured for placement on a Bowman's membrane of the eye. A covering comprises a first portion and at least a second portion. The first portion comprises a lens configured for positioning on the eye. The at least a second portion is configured to conform to irregularities of the epithelium to adhere to the first portion and the onlay to the cornea to inhibit motion.

In many embodiments, the at least the second portion is configured with a lower hydrophobic surface to adhere the first lens portion and the onlay to the cornea with mechanical resistance sufficient to resist a blink of the eyelid.

In another aspect, embodiments provide a system to correct vision of an eye having a cornea having an epithelium. The system comprises an onlay to correct the vision of the patient and a covering. The covering comprises at least one region adapted to conform to the shape of cornea to decrease swelling of the cornea and adhere the onlay to the cornea.

In many embodiments, the covering is configured to at least one of deturgesce or minimize swelling of the cornea when the covering is placed on the cornea over the onlay.

In many embodiments, the covering comprises a thickness of no more than about 200 microns and a width of at least about 5 mm to conform to the cornea and the onlay.

In many embodiments, the covering comprises at least one of a hydrophobic layer or an upper hydrophobic surface extending along at least an inner portion of the covering to inhibit water flow through the covering. The at least one of the hydrophobic layer or the upper hydrophobic surface may comprise at least one of silicone, elastomer, silicone elastomer or polyurethane.

In many embodiments, the covering comprises at least one of a lower hydrophilic layer or a hydrophilic surface extending along at least a inner portion of the covering to inhibit sliding of the covering along the cornea. The at least one of the lower hydrophilic layer or the lower hydrophilic surface may comprise at least one of hydrogel, 2-hydroxyethylmethacrylate (HEMA), methacrylic acid (MA), methyl methacrylate (MMA), N,N-dimethylacrylamide (DMA); N-vinyl pyrrolidone (NVP), phosphorylcholine (PC), poly vinyl alcohol (PVA) or polyvinyl pyrrolidone (PVP), tris-(trimethylsiloxysilyl)propylvinyl carbamate (TPVC); N-carboxyvinyl ester (NCVE); silicone hydrogel, poly[dimethylsiloxyl]di[silylbutanol]bis[vinyl carbamate] (PBVC); silicate, plasma treated silicone hydrogel, plasma coating producing glassy islands, 25 nm plasma coating with high refractive index, fibrin, or bioglue.

In many embodiments, the covering comprises an oxygen Dk parameter of at least about 80. For example, the covering comprises a thickness within a range from about 25 to about 100 microns and an oxygen Dk parameter of at least about 80. The oxygen Dk parameter may comprise at least about 350 or more to inhibit swelling when the covering is worn for a plurality of days.

In many embodiments, the covering comprises an upper optical surface extending along at least an inner portion of the covering.

In many embodiments, the covering comprises an inner portion adapted to conform to the onlay when positioned on the cornea.

In many embodiments, the covering comprises at least an inner portion having a substantially uniform thickness extending from a lower surface to an upper surface such that the covering has an optical power within a range from about −5 D to about +5 D along at least the inner portion of the covering. The range can be less, for example from about −1 D to about +1 D.

In many embodiments, the covering comprises a lower curved surface extending along at least an outer portion of the covering, the lower curved surface shaped to fit the cornea away from the onlay.

In many embodiments, the outer portion is adapted to form a seal with an epithelium of the cornea away from the onlay. The outer portion may comprise a covering radius of curvature and is configured to stretch when the peripheral portion of the covering is placed against a peripheral portion of cornea away from the onlay and wherein the covering radius of curvature is less than a radius of curvature of the cornea.

In many embodiments, the inner portion comprises a soft material and a thickness of no more than about 200 microns such that the inner portion conforms to a contour of an anterior surface of the onlay when the outer portion forms a seal with the epithelium away from the onlay.

In many embodiments, the covering comprises an inner portion and an outer portion and wherein the inner portion comprises a lower hydrophilic surface sized to contact the onlay under an epithelial defect and wherein the outer portion comprises a hydrophobic lower surface sized to contact the epithelium.

In many embodiments, the inner portion is adapted to conform to an anterior surface profile of the onlay and inhibit sliding along the onlay and wherein the outer portion is adapted to form a seal when the outer portion contacts the epithelium.

In many embodiments, the system further comprises a contact lens configured to hold the covering against an epithelial defect when the epithelial defect heals, and the covering is adapted to conform to a curved surface contour of the cornea when the contact lens retains the covering against the epithelial defect.

In another aspect, embodiments provide a method of correcting vision of a patient having an eye and a cornea. An onlay is provided on the cornea to correct vision. A covering is placed on the cornea over the onlay, and the covering is adhered to the cornea to reduce swelling of the cornea.

In many embodiments, the epithelium is separated from a Bowman's membrane to position the onlay on the Bowman's membrane and wherein the epithelium regenerates between the onlay and the covering. The onlay may be positioned in an epithelial pocket with epithelium disposed between the onlay and the covering. The epithelium can be debrided to expose the Bowman's membrane and the onlay positioned on the Bowman's membrane. The onlay may be molded in situ on the cornea.

In many embodiments, the covering forms a seal with the cornea to decrease water flow into the cornea.

In many embodiments, the covering comprises an outer periphery and wherein the epithelium grows over at least a portion of the outer periphery. The covering may be placed on the epithelium such that the epithelium is disposed under the outer periphery when the epithelium grows over the outer periphery.

In many embodiments, the covering is placed over an epithelial defect of the cornea and wherein the covering is removed when the epithelial defect is healed. The epithelium may remain on the cornea and the onlay and separates from the covering when the covering is removed. Water can be provided to the eye so as to loosen the covering from the epithelium when the covering is removed.

In many embodiments, the covering comprises a substantially water impermeable material to inhibit swelling of the cornea when the seal is formed.

In many embodiments, the covering comprises a substantially oxygen permeable material.

In many embodiments, the cornea comprises an epithelial defect when the covering is placed on the cornea, the method further comprising removing the covering when epithelial defect is healed.

In many embodiments, the cornea is measured to determine a characteristic of the covering, and the covering is selected from among a plurality of coverings in response to the characteristic such that the seal is formed when the covering is placed on the cornea. For example, the cornea can be measured to determine a curvature of the cornea and the characteristic comprises a radius of curvature of a lower surface of the covering. The covering may comprise an optical power within a range from about −5 D to about −5 D. The range can be from about −1 D to about +1 D.

In another aspect, embodiments provide a system to correct vision of an eye of a patient, in which the eye has a cornea. An onlay is configured for placement on the cornea to correct the vision of the patient. A covering comprises an inner portion and an outer portion. The covering comprises an inner portion comprising a lens. The outer portion is configured to conform to irregularities of the cornea of the eye to retain the inner portion comprising the lens over the onlay.

The irregularities may comprise many irregularities of the cornea. The irregularities may comprise an epithelial defect, a stromal defect, or a Bowman's membrane defect.

In many embodiments, a water impermeable layer extends across the inner portion and the outer portion to adhere the inner portion and the outer portion to the cornea with water suction.

In many embodiments, the inner portion comprises rigidity to retain optical smoothness of a front surface of the lens when the lens is placed over the onlay with epithelial irregularities disposed therebetween.

In many embodiments, the inner portion comprises a first rigidity to retain optical smoothness of a front surface of the lens when the lens is placed over the onlay and the outer portion comprises a second rigidity to conform to the cornea and seal an epithelial defect, the first rigidity greater than the second rigidity. The inner portion may be configured to comprise a first inner configuration prior to placement on the eye and a second inner configuration after placement on the eye, the second inner configuration substantially similar to the first inner configuration to retain optical properties of the lens. The outer portion can be configured to comprise a first outer configuration prior to placement on the eye and a second outer configuration after placement on the eye, and the second outer configuration may be substantially different from the first outer configuration such that the second configuration conforms to the epithelium to seal the outer portion against the epithelium.

In many embodiments, the inner portion and the outer portion each comprise a hydrophobic layer to inhibit water and an upper hydrophilic layer and a lower hydrophilic layer, the hydrophobic layer disposed between the upper hydrophilic layer and the lower hydrophilic layer.

In many embodiments, the outer portion comprises an oxygen permeability Dk parameter of at least about 200. The outer portion may comprise an oxygen permeability Dk parameter of at least about 350. For example, the outer portion comprise an oxygen permeability Dk parameter of at least about 400, or at least about 500.

In many embodiments, the inner portion comprises an oxygen permeability Dk parameter of at least about 100. The inner portion may comprise an oxygen permeability Dk parameter of at least about 200. For example, the inner portion comprises an oxygen permeability Dk parameter of at least about 350. The inner portion may comprise an oxygen permeability Dk parameter of at least about 400, or at least about 500.

The inner portion and the outer portion may each comprise a suitable hardness parameter. The inner portion may comprise a hardness parameter within a range from a Shore A durometer of about 30 to about 94 M on a Rockwell scale. The outer portion comprises a Shore A durometer hardness parameter within a range from about 20 to about 80.

In many embodiments, the hydrophobic layer of the inner portion and the hydrophobic layer of the outer portion comprise silicone having a Dk of at least about 200.

In many embodiments, the inner portion comprises a thickness of no more than about 200 um.

In many embodiments, the outer portion comprises a peripheral thickness of no more than about 100 um and extends toward the central portion with an increase in thickness.

In many embodiments, the outer portion comprises a radius of curvature along a lower surface. The outer portion can be configured to conform to a boundary of the epithelial defect. The outer portion of the covering can be configured to conform to a first curvature of the cornea outside a debrided zone and conform to a second curvature of the cornea within the debrided zone such that the cornea is sealed over the debrided zone.

In many embodiments, the inner portion comprises a first piece of material and the outer portion comprises a second piece of material adhered to the first piece.

In many embodiments, the inner portion and the outer portion comprise a similar material and wherein the inner portion comprises a first thickness and the outer portion comprises a second thickness less than the first thickness such that the inner portion is configured to retain an optical front surface when placed on the cornea and the outer portion is configured to conform to the irregularities of the cornea.

In many embodiments, the inner portion comprises a first hardness and the outer portion comprises a second hardness, the first hardness greater than the second hardness such that the inner portion is configured to retain an optical front surface when positioned on irregularities of the cornea. The irregularities of the cornea comprise irregularities of a Bowman's membrane, a stroma or irregularities of an epithelium.

In another aspect, embodiments provide a method of treating vision of an eye having a cornea. An onlay is provided on the cornea. A covering is placed on the cornea of the eye over the onlay. Swelling of the cornea decreases when the covering is positioned over the onlay and adhered to the cornea.

In many embodiments, the covering is adhered to the cornea with water suction. The endothelium may pump water from the cornea so as to suck the covering onto the cornea.

In many embodiments, a contact lens is placed over the covering to adhere the covering to the cornea. The contact lens can be removed from the covering when the covering is adhered to the cornea with the onlay positioned under the covering. For example, the contact lens may be removed from the covering no more than about one hour after the contact lens is positioned on the covering.

In many embodiments, the therapeutic covering corrects optical aberrations of the eye when the covering is positioned over the onlay and adhered to the cornea. The optical aberrations correspond to irregularities of the cornea, irregularities of Bowman's membrane, irregularities of the stroma, or irregularities of the epithelium.

BRIEF DESCRIPTION OF THE DRAWINGS

FIG. 2A-1 shows an onlay as in FIG. 2A with suction and partial re-epithelialization, in accordance with embodiments;

FIG. 3A1 shows an anterior view of an onlay as in FIG. 3A with adhesive on a posterior surface of the onlay visible through the onlay;

FIG. 3A2 shows a posterior view of an onlay as in FIG. 3A with adhesive disposed in an annular track on the posterior surface of the onlay;

FIG. 3B1 shows adhesion of an onlay as in FIG. 2A with tissue welding, according to embodiments of the present invention;

FIGS. 3C and 3C1 show adhesion of an onlay as in FIG. 2A with a protein cross-linking agent, according to embodiments of the present invention;

FIG. 3D shows application of adhesive to an onlay as in FIG. 2A, according to embodiments of the present invention;

FIG. 3D1 shows a double sided sticky tape adhesive suitable for use with an onlay;

FIG. 3D2 shows an onlay shaped to cover at least a portion of the conjunctiva; according to embodiments of the present invention;

FIG. 3E shows microshaped corneal tissue to adhere an onlay as in FIG. 2A, according to embodiments of the present invention;

FIG. 3E1 shows interlocking structures to adhere an onlay as in FIG. 3E;

FIG. 3E2 shows nano structures to adhere an onlay as in FIG. 3E;

FIG. 3G1 shows surgical tucking of the onlay into the stroma and/or Bowman's membrane, according to embodiments of the present invention;

FIG. 3G2 shows incision in tissue of the cornea to prepare to cornea as in FIG. 3G1;

FIG. 3G3 shows an excision in tissue of the cornea shaped to receive an onlay, according to embodiments of the present invention;

FIGS. 3H and 3H1 show integration of the implant matrix with the host cornea, according to embodiments of the present invention;

FIG. 3I1 shows a bottom view of an onlay with anchors comprising bioadhesive tacks used to adhere the onlay to the cornea;

FIG. 3I2 shows a side cross-sectional view of the onlay as in FIG. 3I1;

FIG. 3J-1 shows a degradable water inhibiting barrier layer disposed on an upper side along an anterior surface of an onlay;

FIG. 3J-2 shows a degradable water inhibiting barrier layer disposed on a lower side of an onlay;

FIG. 3J-3 shows a degradable water inhibiting barrier layer disposed along on an inner layer of an onlay;

FIG. 4C1 shows use of a femto second laser to make a button as in FIG. 4C;

FIG. 4E shows a penetrating (tattoo) deposition process through the epithelium to form a lens on and/or in Bowman's membrane and/or stroma, according to embodiments of the present invention;

FIG. 9A-1 shows a therapeutic covering as in FIG. 9A positioned over an onlay, with the outer portion conforming to one or more irregularities on the underlying Bowman's membrane and/or epithelial tissue, so as to seal the covering over the onlay and adhere the onlay to the cornea when the epithelium grows over the onlay;

DETAILED DESCRIPTION OF THE INVENTION

The corneal onlays described herein can be used to correct myopia, hyperopia, astigmatism, presbyopia and high order aberrations of the eye such as spherical aberration and coma measured with wavefront systems, and additional aberrations. The corneal onlays may also be used to correct the vision of eyes with corneal pathology, for example eyes with keratoconus. Eyes with keratoconus can be thinner centrally, and the onlay described herein can thicken the cornea centrally and may correct aberrations of the eye associated with keratoconus.

The eye may comprise many tissues suitable for combination with the onlay so as to correct vision. The human of the cornea comprises a Bowman's membrane (hereinafter "Bowman's") disposed under the epithelium, and Bowman's membrane is suitable for receiving an onlay. Under Bowman's membrane, the cornea comprises stromal tissue that can be suitable for receiving the onlay, for example when a layer of human corneal tissue comprising Bowman's membrane is excised. The cornea of some animals may not comprise a Bowman's membrane and may comprise stroma under the epithelium. The onlays described herein can be adhered to Bowman's membrane, the stroma, or both. As used herein the term Bowman's membrane and/or stroma encompasses: the Bowman's membrane or the stroma, or both.

I. Removal of Epithelium

Figure 1A:
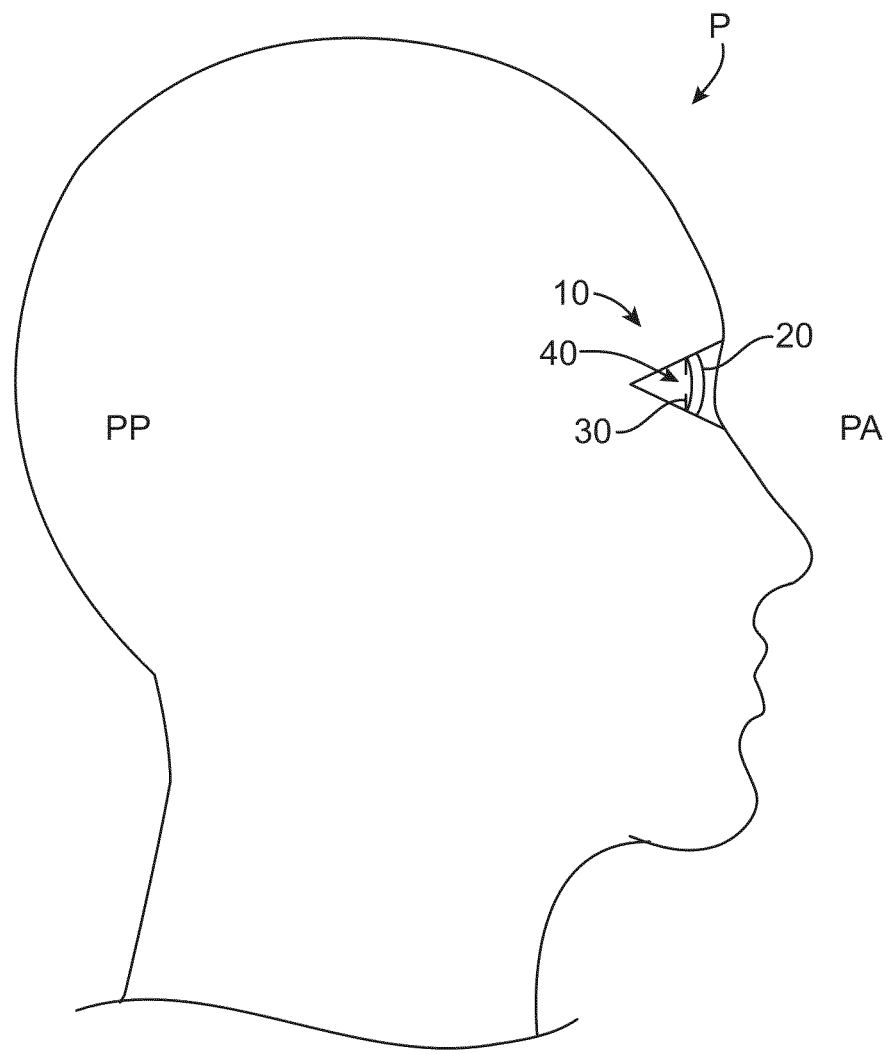
FIGS. 1A and 1B show an eye of a patient and removal of an epithelial layer of an eye to expose Bowman's membrane and/or stroma, according to embodiments of the present invention.
Figure 1B:
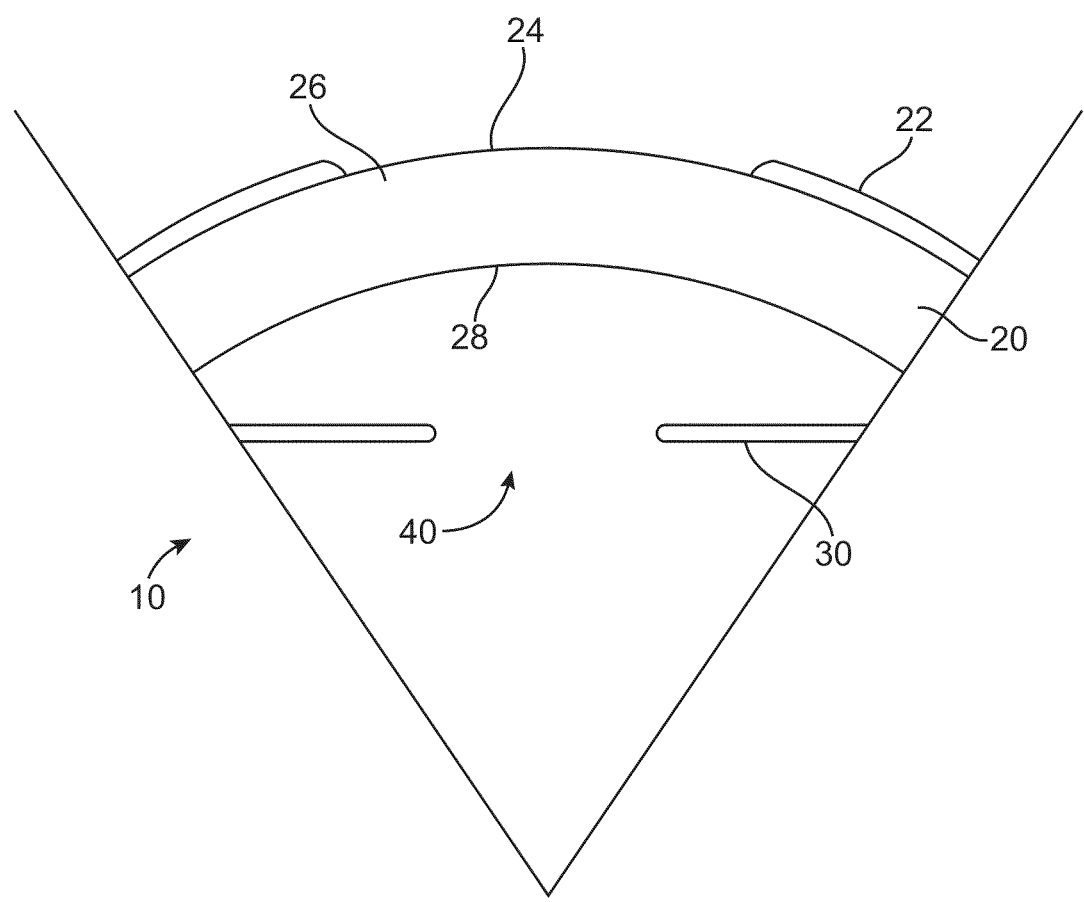

FIGS. 1A and 1B show an eye of a patient P and removal of an epithelial layer 22 of an eye so as to expose Bowman's membrane 24 and/or stroma 26 to prepare the eye to receive the onlay. The cornea of the eye is disposed anteriorly on an anterior side PA the patient. The iris of the eye is disposed posterior to the cornea toward a posterior side PP of the patient. The cornea 20 of the eye includes the epithelium 22, Bowman's membrane 24, the stroma 26, and the endothelium 28.

The epithelium can be removed with many known ways including at least one of a brush, a trephine, ethanol, cocaine, laser ablation, lifting a continuous portion of epithelium, or a separator having an edge. Removal of the epithelium exposes an anterior surface of Bowman's membrane. In some animals, Bowman's membrane is not present such that removal of the epithelium exposes stromal tissue. In patients who have undergone PRK, removal of the epithelium exposes stromal tissue and may also expose Bowman's membrane, for example near the periphery of the ablation. Therefore, as used herein the Bowman's membrane and/or the stroma encompasses Bowman's membrane, or the stroma, or both.

II. Onlay Materials and Epithelialization Over Anterior Surface of Onlay

Figure 2A:
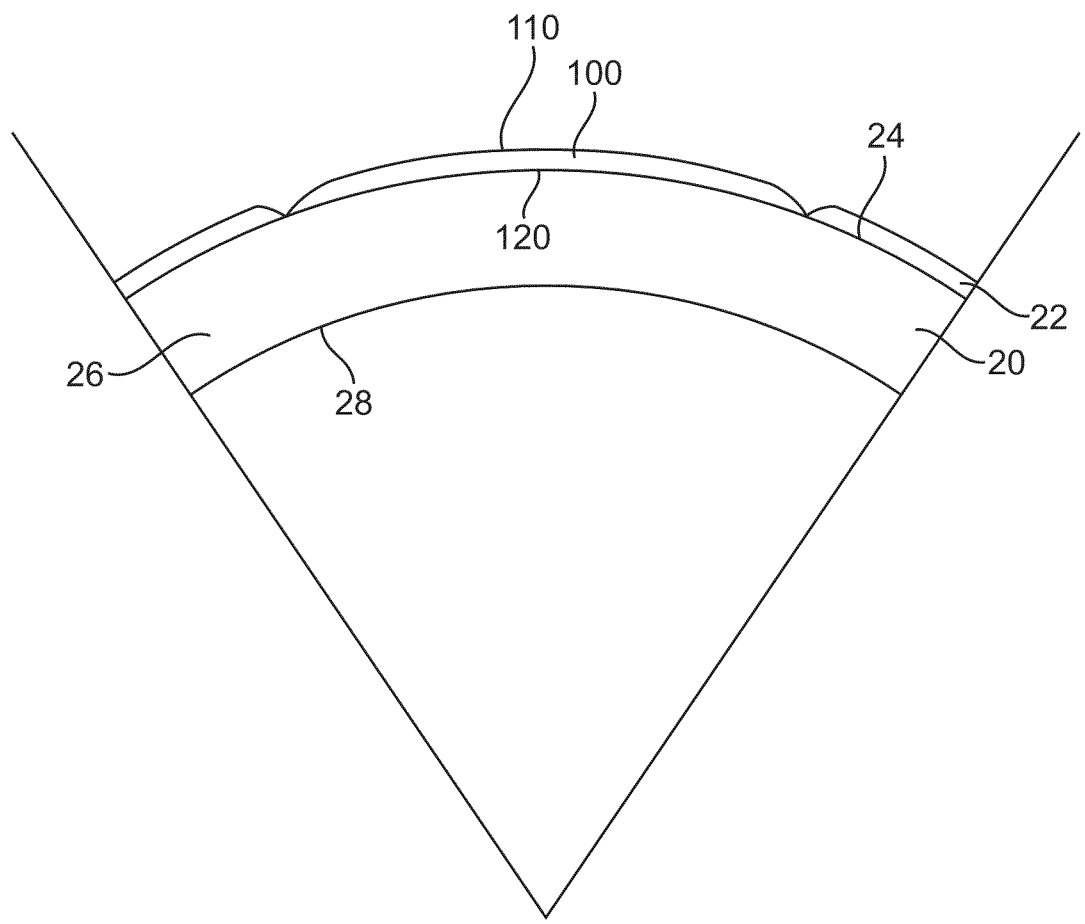
FIG. 2A shows an onlay positioned on an exposed surface of an eye as in FIGS. 1A and 1B.

FIG. 2A shows onlay 100 positioned on an exposed surface of an eye as in FIG. 1B. The onlay includes anterior surface 110 and posterior surface 120. The posterior surface of the onlay can be disposed on the exposed anterior surface of Bowman's membrane 24 of the cornea 20. The corneal onlay is shaped to correct vision of the eye. The onlay can be used to correct myopia, hyperopia, astigmatism, presbyopia and high order aberrations of the eye such as wavefront aberrations comprising spherical aberration and coma, and may comprise known shapes based on the index of refraction of the onlay material. The onlay can be surrounded by an annular epithelium that has not been removed from the cornea, such that the epithelium can grow over the onlay, referred to as epithelialization.

The onlay lens material may comprise a water barrier layer, such that the onlay can be sucked down onto the cornea, for example with endothelial suction. The water barrier layer may comprise a hydrophobic barrier layer to inhibit water penetration of the onlay. For example the onlay may comprise a hydrophobic layer, which hydrophobic layer coated on each of the upper and lower surfaces with a hydrophilic layer. The silicone may comprise a low water content silicone, for example no more than about 5% water, or even 1% water or less.

The onlay lens material may comprise a water barrier layer, such that the onlay can be sucked down onto the cornea, for example with endothelial suction. The water barrier layer may comprise a hydrophobic barrier layer to inhibit water penetration of the onlay. For example the onlay may comprise a hydrophobic layer, which hydrophobic layer coated on each of the upper and lower surfaces with a hydrophilic layer. The silicone may comprise a low water content silicone, for example no more than about 5% water, or even 1% water or less.

The onlay lens material and thickness may be configured with substantial oxygen permeability, for example with an oxygen Dk parameter of at least about 350, such that endothelial pumping is not inhibited during re-epithelialization. Depending on the onlay material and thickness, the oxygen Dk parameter may comprise at least about 400, for example 500 or more. The onlay lens material and barrier may comprise many known materials with high oxygen permeability, for example silicone.

Figures 1, 2A:
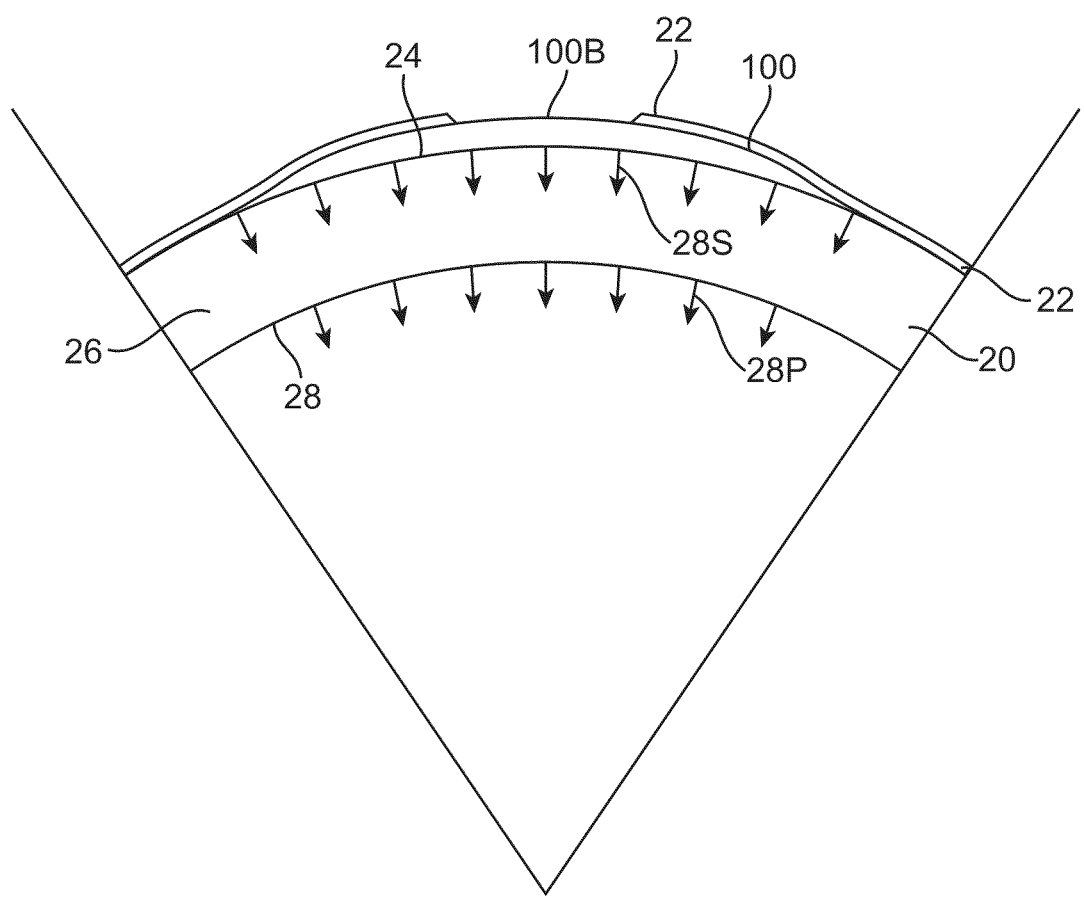

FIG. 2A-1 shows an onlay as in FIG. 2A with suction and partial re-epithelialization. The endothelium 28 is capable of removing water from the cornea with endothelial pumping 28P. The onlay may comprise a water barrier 100B, such that pumping of water from the cornea by the endothelium can adhere the onlay to the cornea with suction 28S. As the onlay comprises a water barrier, water flow through the onlay is inhibited, such that the onlay is adhered onto the cornea.

Figure 2B:
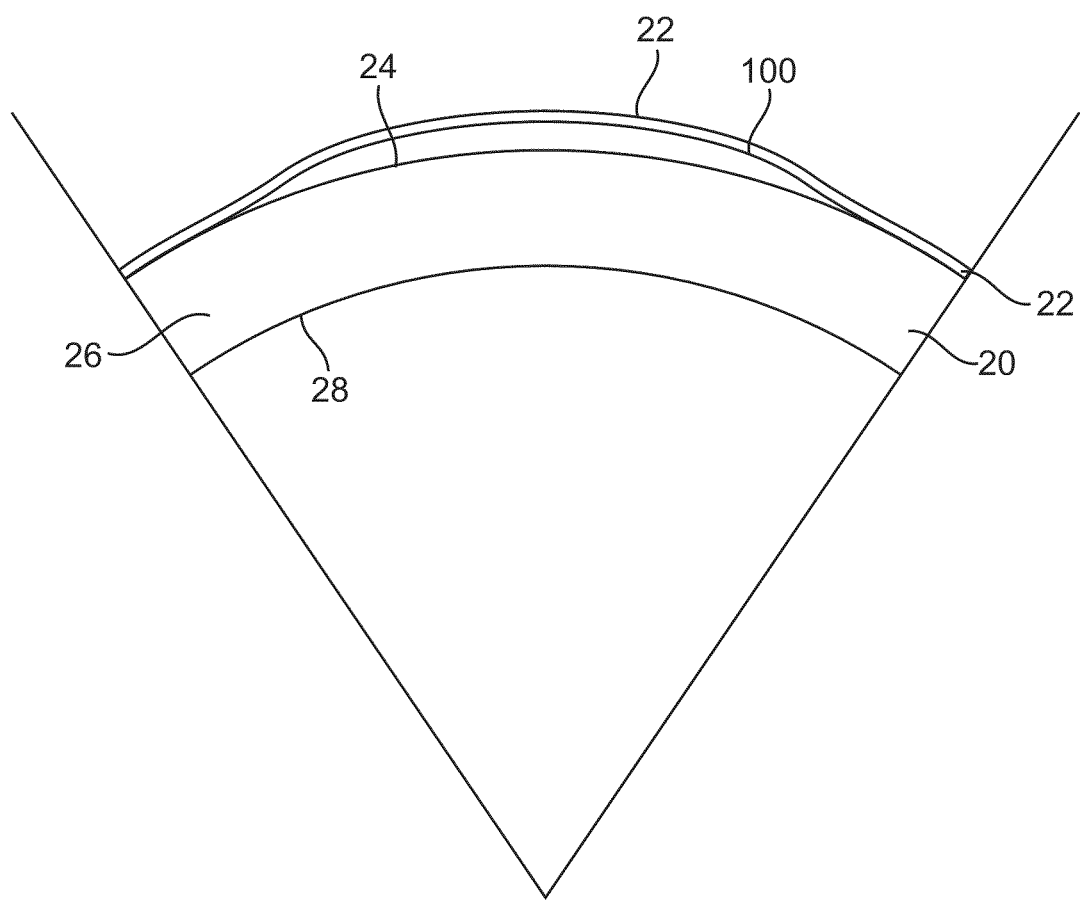
FIG. 2B shows an onlay positioned on an exposed surface of an eye as in FIG. 2A with epithelialization over the anterior surface of the onlay.

FIG. 2B shows an onlay positioned on an exposed surface of an eye as in FIG. 2A with epithelialization over the anterior surface of the onlay. The epithelium has grown over the onlay on the anterior surface of the onlay. The onlay may be comprised of many materials so as to permit epithelialization, innervation and/or integration of the onlay with the cornea. The onlay may comprise at least one of a donor cornea, a collagen based material, or synthetic material.

Although the healthy corneal epithelium comprises a barrier in the natural and healthy cornea, the healthy epithelium can pass at least some water therethrough. The corneal onlay with the water barrier can further inhibit the flow of water, such that the onlay can remain adhered to the cornea with suction after the epithelium has regenerated.

Figure 2C:
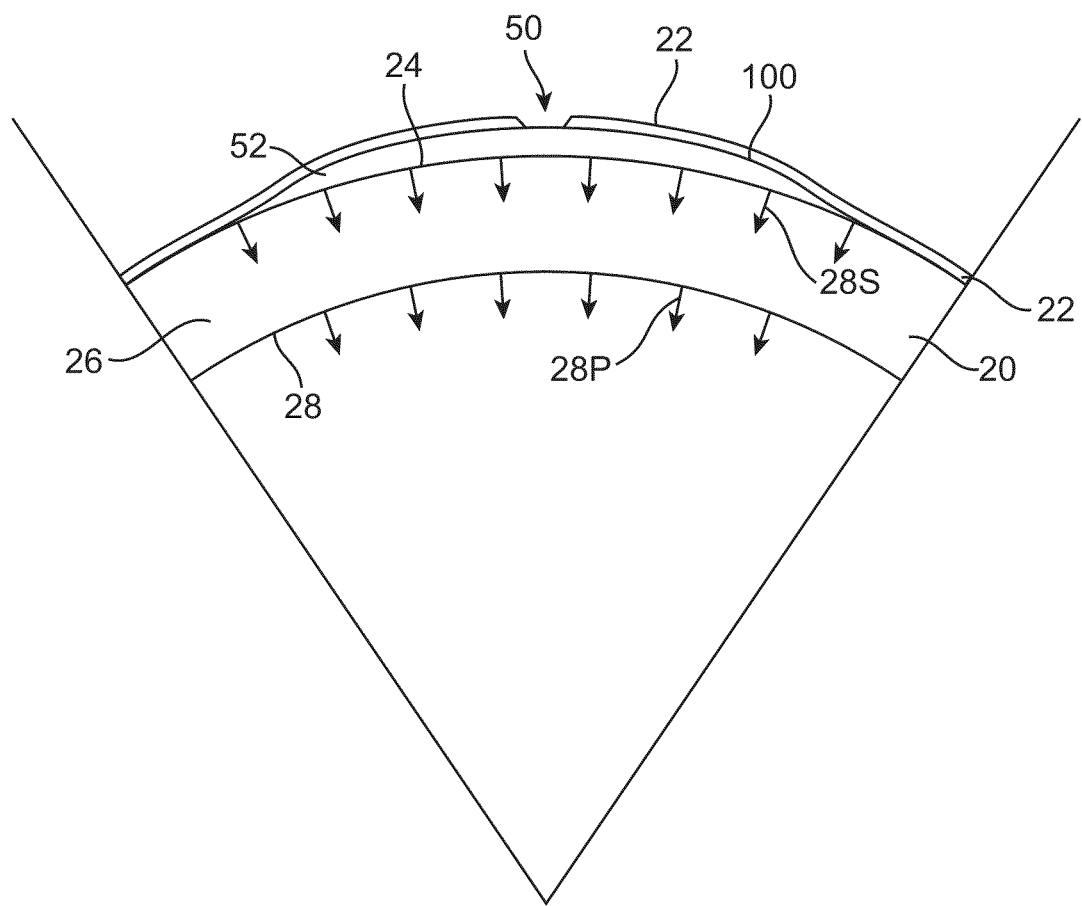
FIG. 2C shows an onlay as in FIG. 2A placed in a surgically formed epithelial pocket to hold the onlay.

FIG. 2C shows an onlay as in FIG. 2A placed in a surgically formed epithelial pocket to hold the onlay. The epithelium can be removed such that the epithelium substantially covers the onlay at the completion of surgery. The epithelium substantially covering the onlay can help to adhere the onlay to Bowman's membrane, for example with endothelial suction of the onlay as described herein below. A flap of epithelial tissue may be removed to expose Bowman's membrane, the onlay positioned on the exposed Bowman's membrane, and the flap placed over the onlay to cover substantially the onlay. The flap may comprise a hinge at the edge such that the flap remains attached to Bowman's membrane. A pocket 50 may be formed in the epithelium surgically thorough an incision 52 so as to separate the epithelium from Bowman's membrane, such that the epithelial cell layer is separated from Bowman's membrane so as to define the pocket 52. The onlay can be inserted into the pocket, such that the epithelium substantially covers the onlay and retains the onlay.

II. A. Donor Cornea

The onlay may comprise tissue from a donor cornea, and the donor cornea may comprise a human donor cornea, also referred to as an allograft. Known methods of preparing a donor cornea can be used, for example epikeratophakia (hereinafter "EPI-K"). In some embodiments, the donor cornea may comprise an artificial human donor cornea, for example a known artificial human donor cornea. The donor cornea may comprise an artificial human cornea capable of innervation when placed on the cornea. In some embodiments, the donor cornea may comprise a xenograft, for example porcine or bovine cornea. The donor tissue may comprise homologous donor tissue, for example from a sheet of excised tissue and/or a cell line.

II. B. Collagen Based Materials

The onlay may comprise many collagen based materials. The onlay may comprise human recombinant material, for example fibrogen. The onlay material may comprise collagen plus a polymer, for example a neoglycopolymer-crosslinked biopolymer matrix, a biosynthetic matrix, collagen hydrogel, for example collagen with poly ether amide (PEA) hydrogel and collagen with acrylate. Collagen based materials that may be used in accordance with some embodiments of the present invention are described in the following U.S. patents and patent applications U.S. Pat. Nos. 4,452,925; 4,983,181; 5,213,720; 5,522,888; 5,114,627; 5,716,633; 5,836,313; 6,645,715; 2006/0034807; US2006/013050; US2006/0134170; 2006/0246113; and 2007/002046, the disclosures of which may be suitable for combination in accordance with embodiments described herein.

The collagen based material may comprise collagen from a human cell line used to generate a collagen based material.

The above donor and collagen based materials can be stabilized and/or solidified by soaking in a photosensitizer, for example riboflavin, and exposed to light so as to induce photocatalyzed crosslinking, for example with UV or blue light.

II. C. Synthetic

The onlay lens material may comprise a known synthetic material, for example porous hydroxyethyl methacrylate (HEMA) hydrogel, hydrogel, silicone, for example hydrated silicone and derivatives thereof.

The onlay lens material may comprise a synthetic water barrier layer, such that the onlay can be sucked down onto the cornea, for example with endothelial suction. The synthetic water barrier layer may comprise a hydrophobic barrier layer to inhibit water penetration of the onlay. The hydrophobic layer may comprise a degradable material such that the layer is configured to degrade when epithelium is positioned over the onlay. For example, the degradable material can be configured to degrade within about one week of placement on the cornea. The degradable material comprises many known degradable materials, for example at least one of poly lactic acid (PLA), poly glycolic acid (PGA) or PLA/PGA copolymer. The material may comprise a hydrophobic bioerodible and degradable suture material disposed on the anterior surface of the onlay to inhibit water as noted above.

In many embodiments, the onlay comprises hydrophilic material on at least one of a lower surface or an upper surface. The lower hydrophobic material may comprise at least one of a lower hydrophilic layer or a hydrophilic surface extending along at least a inner portion of the onlay. The at least one of the lower hydrophilic layer or the lower hydrophilic surface may comprise at least one of hydrogel, 2-hydroxyethyl-methacrylate (HEMA), methacrylic acid (MA), methyl methacrylate (MMA), N,N-dimethylacrylamide (DMA); N-vinyl pyrrolidone (NVP), phosphorylcholine (PC), poly vinyl alcohol (PVA) or polyvinyl pyrrolidone (PVP), tris-(trimethylsiloxysilyl)propylvinyl carbamate (TPVC); N-carboxyvinyl ester (NCVE); silicone hydrogel, poly[dimethylsiloxyl]di[silylbutanol]bis[vinyl carbamate] (PBVC); silicate, plasma treated silicone hydrogel, plasma coating producing glassy islands, 25 nm plasma coating with high refractive index, fibrin, or bioglue. The upper hydrophilic surface may comprise similar materials.

III. Adhesion of Onlay to Bowman's Membrane and/or the Corneal Stroma.

The onlay may comprise at least one of a synthetic adhesive, a natural and/or biologically derived adhesive, a recombinant adhesive or a hybrid adhesive or derivatives thereof. The adhesive may be combined with additional adherence, for example suction based adherence. The synthetic adhesive may comprise, for example, a least one of a polylysine adhesive, a cyanoacrylate adhesive or a polyethylene glycol adhesive or derivative thereof. The natural and/or biologically derived adhesive may comprises, for example, at least one of a fibrin adhesive or an RPG adhesive or derivatives thereof. The recombinant adhesive may comprise, for example, at least one of a fibrin adhesive, a polylysine adhesive, a biologically derived adhesive from plasma or an RPG adhesive or derivatives thereof. The hybrid adhesive comprises an albumin with glutaraldehyde adhesive.

In some embodiments a tie layer, for example a glue, may adhere or tie the onlay to the surface of the eye. The tie layer remain optically clear with no adverse impact on visual acuity, and may resorb over time.

Figure 3A:
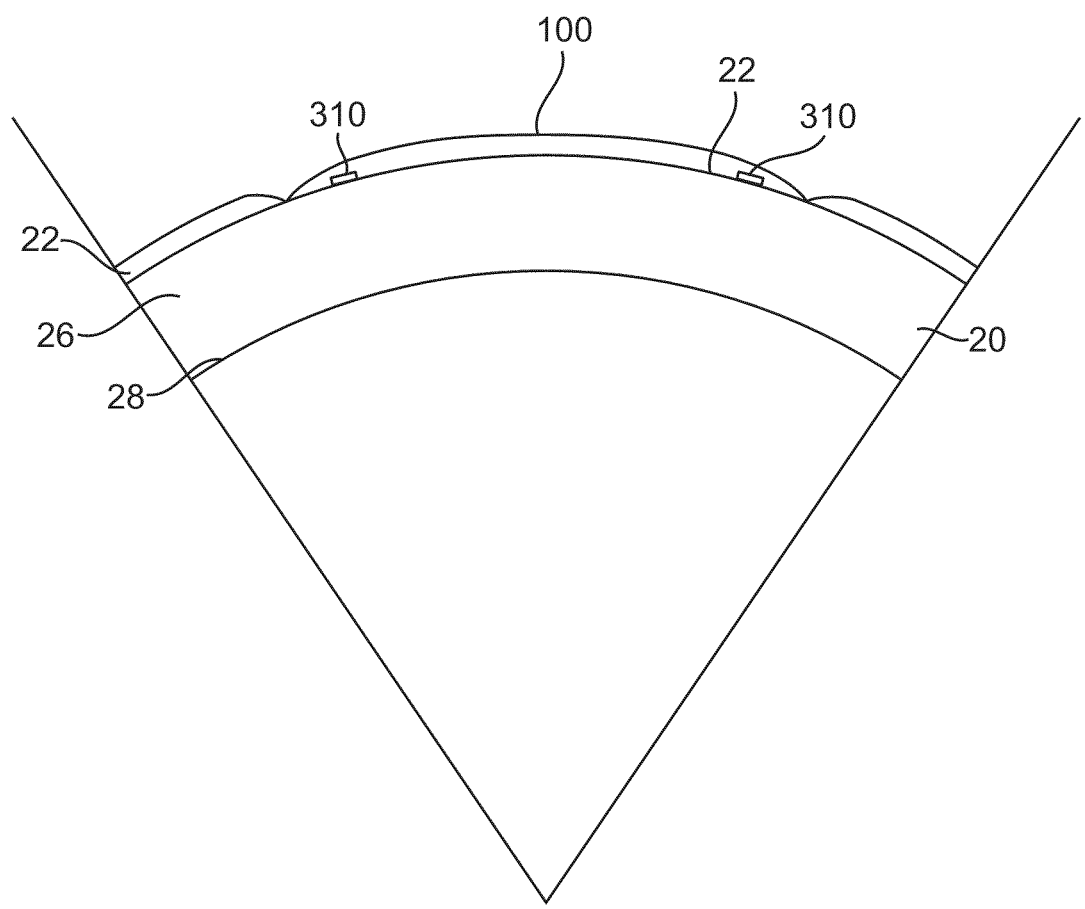
FIG. 3A shows adhesion of an onlay as in FIG. 2A with a glue, according to embodiments of the present invention.

FIG. 3A shows adhesion of an onlay as in FIG. 2A with an adhesive 310. The adhesive can hold the onlay in place on the cornea as the epithelium grows over the anterior surface of the onlay. The adhesive can be applied in many ways.

FIG. 3A1 shows an anterior view of an onlay as in FIG. 3A with adhesive 310 on a posterior surface of the onlay visible through the onlay prior to implantation. The adhesive may be applied along an adhesive track 312.

Figure 3B:
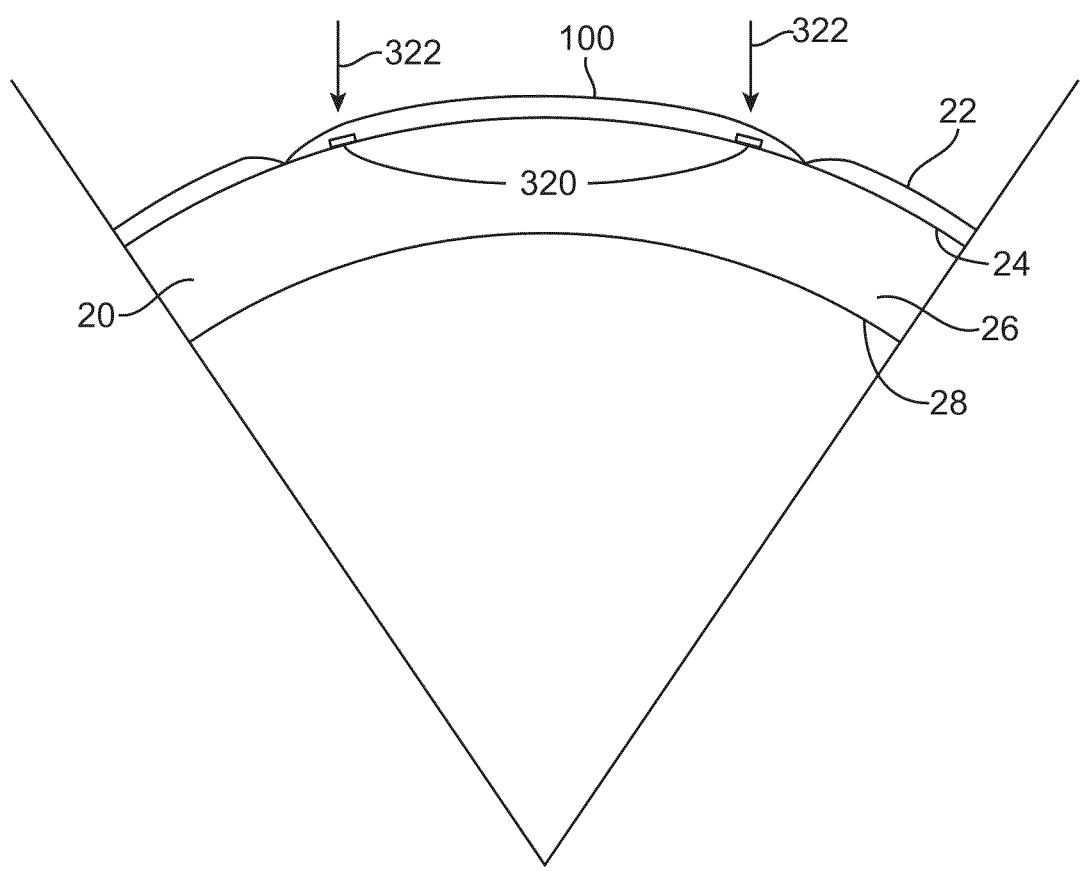
FIG. 3B shows optical tissue welding with an annular track of light sensitive material with an onlay as in FIG. 2A, according to embodiments of the present invention.
Figure 3F:
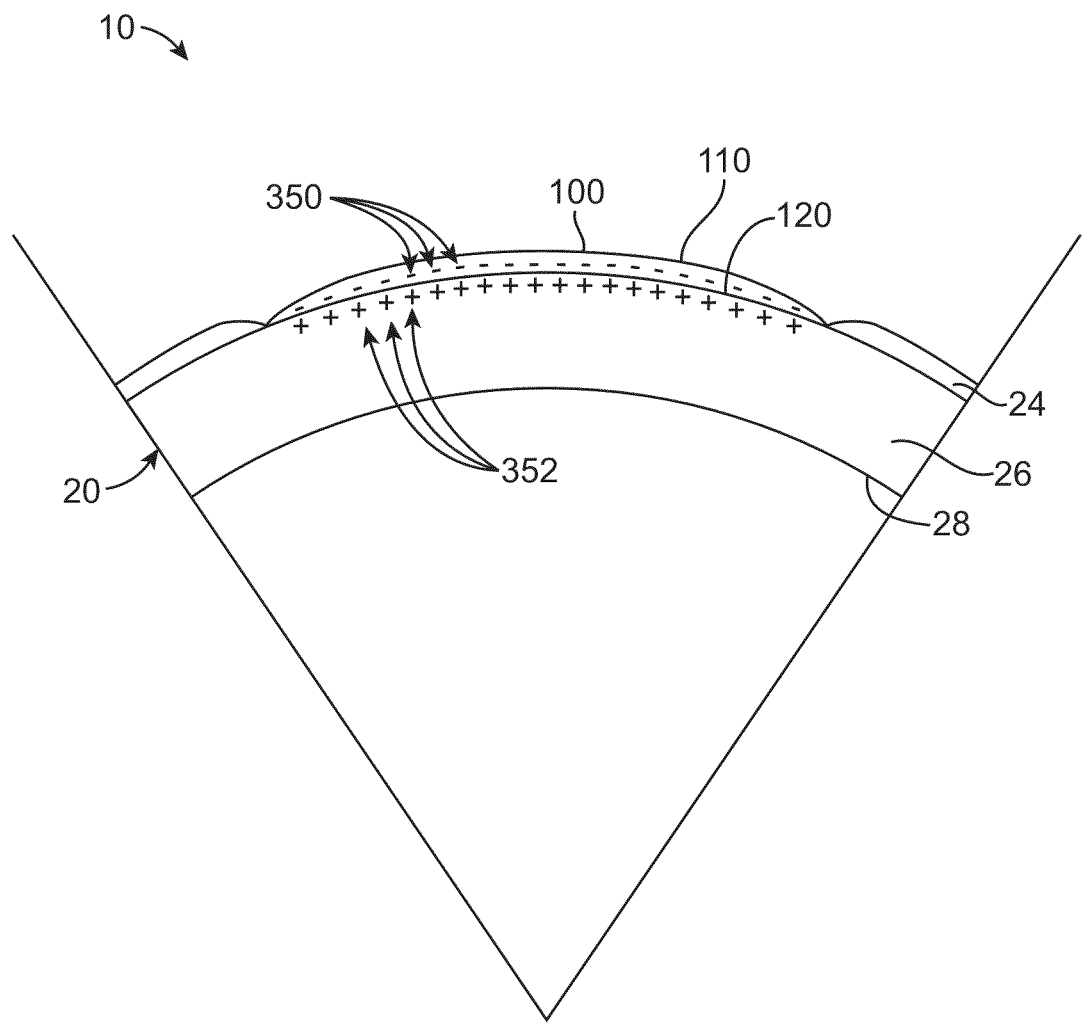
FIG. 3F shows charge to adhere an onlay as in FIG. 2A, according to embodiments of the present invention.
Figure 3G:
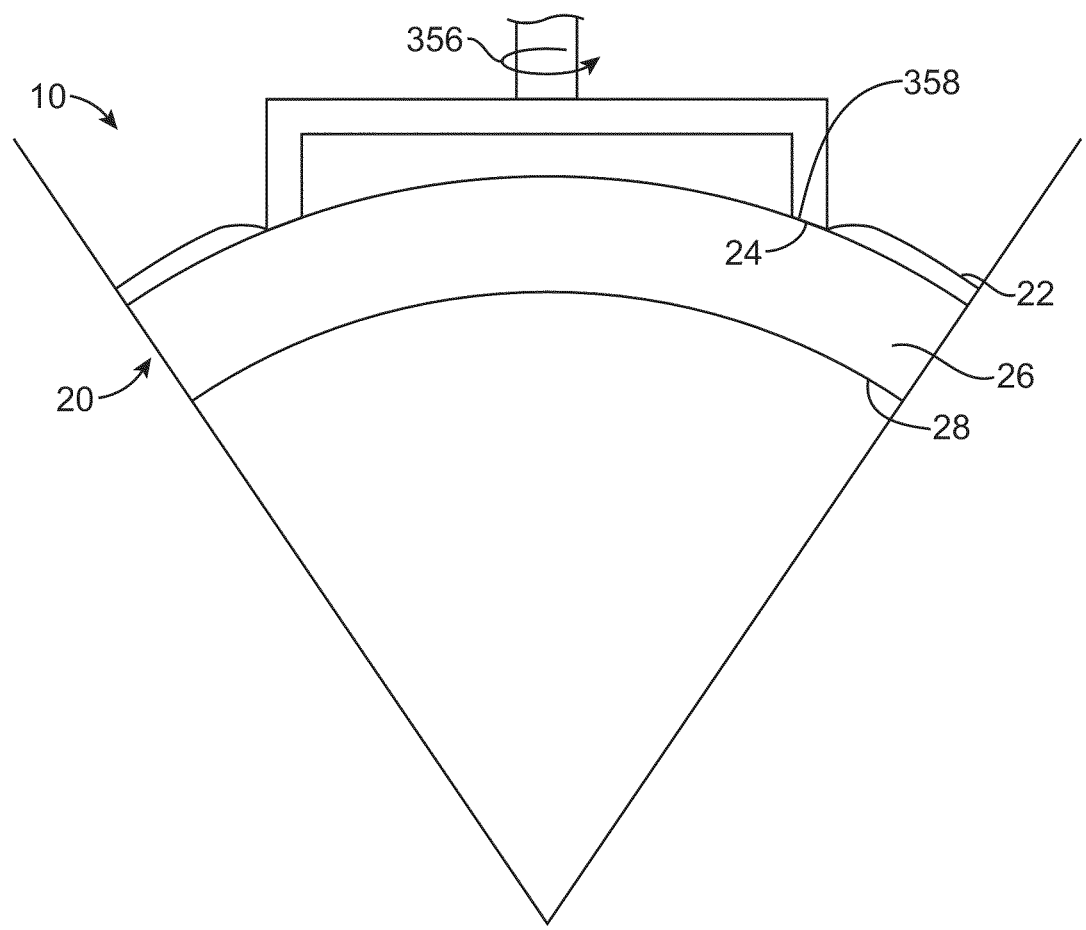
FIG. 3G shows cutting and/or abrading to adhere an onlay as in FIG. 2A, according to embodiments of the present invention.
Figures 1, 3J:
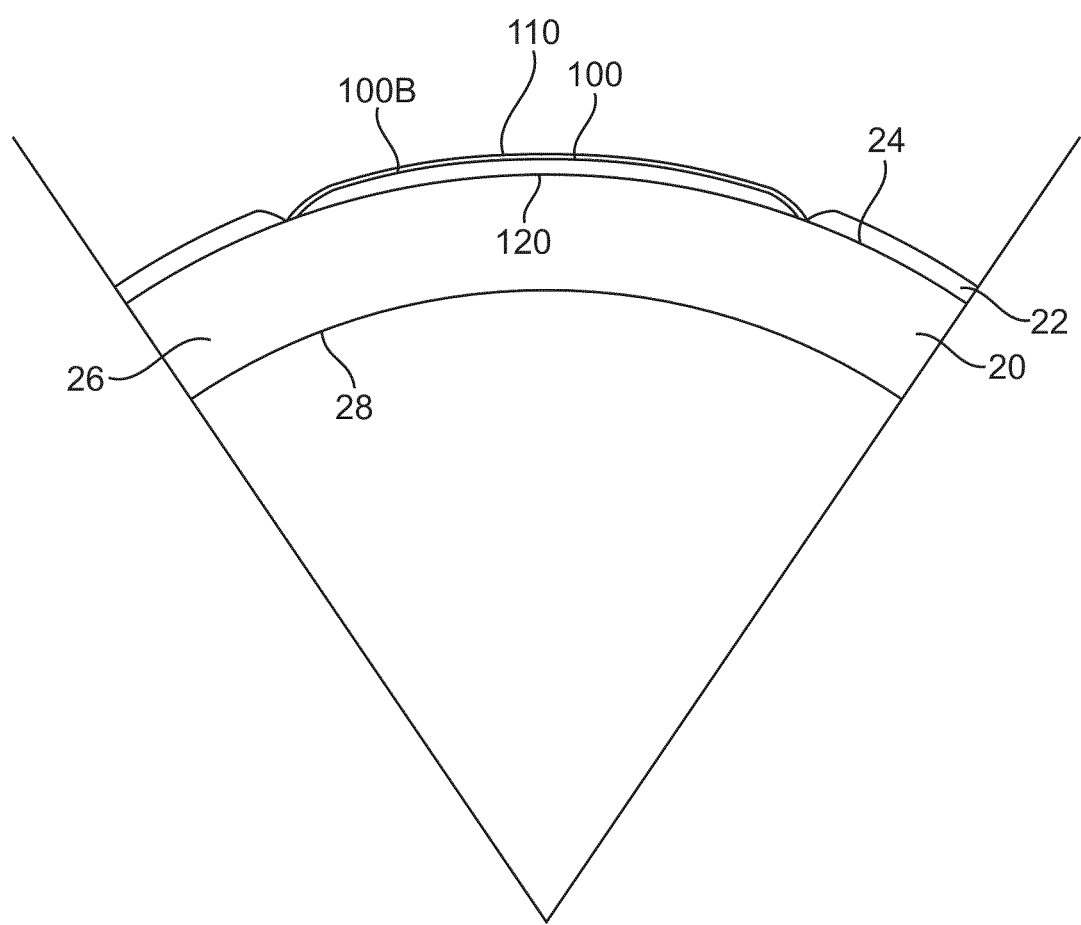
Figures 2, 3J:
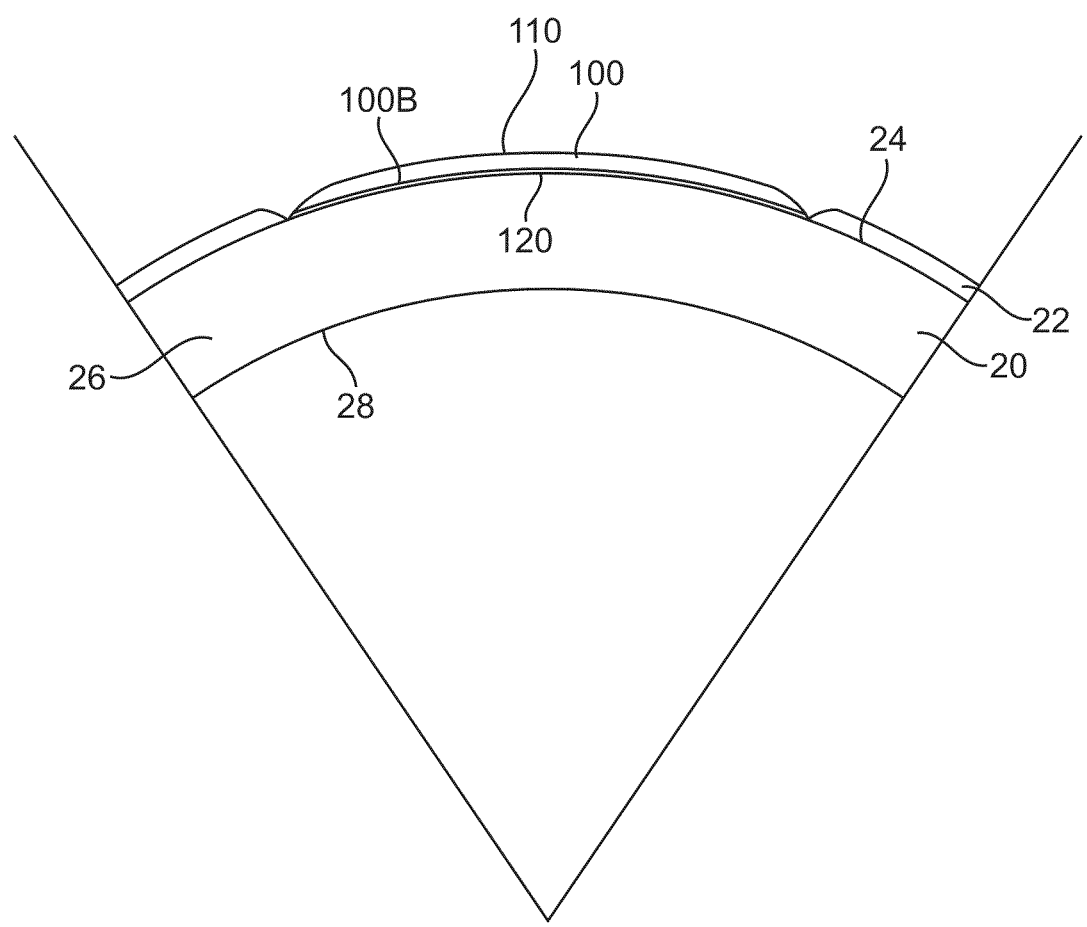

FIG. 3A2 shows a posterior view of an onlay as in FIG. 3A1 with the adhesive disposed in the annular track on the posterior surface of the onlay. Although an annular track is shown, the adhesive can be disposed in many shapes and/or patterns.

III. A. Glue

In many embodiments, the adhesive comprises an adhesive glue. The adhesive glue may comprise many known surgical sealant. The adhesive may comprise a synthetic adhesive, a natural or biologically derived adhesive, a hybrid adhesive, and/or a recombinant adhesive. The synthetic adhesive may comprise, for example, poly-lysine, cyanoacrylate, and/or polyethylene glycol. The natural or biologically derived adhesive may comprise, for example, known fibrin adhesive. The hybrid adhesive may comprise, for example, albumin with glutaraldehyde, and/or modified proteins with activated functional groups, such as such as succinylated collagen. The recombinant adhesive may comprise recombinant fibrin bio-derived from plasma and/or poly-lysine.

In specific embodiments, the adhesive may comprise a fibrin and/or fibrinogen adhesive, commercially available as Tisseal™. The adhesive may comprise a two part component. For example, the fibrinogen component can be placed on cornea, the onlay soaked in thrombin, then applied to cornea so as to form fibrinogen and covalently bond the onlay to the exposed Bowman's and/or stroma, for example with a collagen or collagen based onlay.

The optical clarity of the fibrin adhesive may be modulated by altering the fibrin structure (solid phase) within the fibrin gel, for example when the adhesive is spayed onto the eye to form a layer with a thickness from about 10 to 100 microns. This may be accomplished by altering the gelation time (thrombin concentration between 1-1000 units/mL) or by altering the ionic strength of the liquid phase of the gel. A more opaque ("coarse") gel is created by lower ionic strength and slower gelation times (low thrombin concentration). A clear or "fine" gel can be made by increasing the ionic strength or decreasing the gelation time (almost instantaneous at a high thrombin concentration, while several minutes at a low thrombin concentration). As gelation time usually is preferably consistent for a given medical application, it may be more convenient to alter the ionic strength of the liquid phase by increasing or decreasing the salt concentration (as an example, if using sodium chloride, the concentrations range between 0-500 mM). For example, lyophilized thrombin may be reconstituted in a low ionic strength buffer with the requisite calcium chloride (required for covalent crosslinking of the resultant gel by the transamidation reaction of Factor XIII) in order to create a more opaque gel. To create an optically clear gel, a higher salt concentration buffer system (e.g., saline at twice or more physiological concentration) with calcium chloride can be used. Other ways of altering the ionic strength can be by use of compatible salts and buffers such as potassium chloride, calcium chloride, tris buffer, carbonate buffer, and the like. Alternately or in combination, sugar-based solutions can be used such as dextrose. Dextran solutions can also be used to alter the ionic strength. The buffer/salt solution can be used in either the fibrinogen component or the thrombin component, though it is most convenient to reconstitute and dilute the thrombin component in order to attain the desired gel time.

The adhesive glue may comprise polyethylene glycol (PEG) based adhesive, for example commercially available under the trade names Coseal™ and Duraseal™. The PEG components may be placed on cornea, and the onlay soaked in catalyst, for example a higher pH solution, and the onlay then applied to cornea.

Albumin based glue is commercially available and can be obtained commercially under the trade name Bioglue™.

Cyanoacrylate is commercially available and can be obtained commercially with the trade name Dermabond™ and Histocryl™. Commercially available methylmethacrylate can be obtained and may be used.

The glue may comprise BSA-GTA glue known as Bioglue from Cryolife. The glue may comprise BSA-GTA glue know as Artex™, available from Tenaxis medical. The Glue may comprise Polysacch Multi-arm known as OcuSeal™ available from HyperBranch Medical. The glue may comprise known PEG based glues, for example known as ProPEG™ and/or NeoMend™.

The glue may comprise a polysaccharide multi-arm crosslinked glue, for example commercially available gel available as OcuSeal™, available from HyperBranch Medical as noted above. The adhesive may comprise a two component system with a first cross-linking component and a second branched prepolymer component.

Many of the glues noted above may be used to form the onlay itself, such that the onlay adheres to the eye. For example, the crosslinked glues described above may be used to form the onlay itself and adhere to the cornea, for example with the glue cured in situ to the desired shape so as to adhere to the cornea. The onlay may comprise a mucoadhesive material formed as an optically shaped film and adhered to the cornea, for example at least one of the epithelium, the stroma, or Bowman's.

Many of the above adhesive glues, for example Fibrinogen and/or PEG based glues can be disposed as a dry material on the onlay, such that moisture from the cornea cures the glue when the adhesive is placed on the cornea.

The adhesive may comprise a reversible adhesive. Many of the adhesives described above can be reversed with a removal agent. The adhesive may comprise a removable adhesive that can melt when the removal agent is applied. The removal agent may comprise at least one of a tissue plasminogen activator (TPA) or a streptokinase. The adhesive may comprise fibrin, such that the adhesive can melt when the removal agent is applied to the adhesive.

III. B. Tissue Welding

FIG. 3B shows optical tissue welding with an annular track of light sensitive material with the onlay as in FIG. 2A. A light sensitive material 320 comprising a photo sensitizer may be disposed in the onlay, in the cornea, and or between the cornea and onlay, for example within an indentation of the onlay. Light 322 is applied to the onlay, for example with a laser beam. The applied light interacts with the photo sensitive material and welds the tissue. Although light welding is shown, other welding such as thermal welding may be used in some embodiments.

Many photosensitizers may be used and wavelengths of light may be used to initiate photo-chemical reactions and/or chemical bonding with an appropriate flux of the light energy. The corneal onlay material described above may be combined with the photosensitizer to adhere the onlay to the stroma and/or Bowman's, for example to form a covalent bond with the stroma and/or Bowman's. In some embodiments, UV or blue light may be used, for example with riboflavin as a photosensitizer with an appropriate flux of the light energy distributed over an area. Infrared (IR) light may be used with indocyanine green photosensitizer. Visible light and visible light photosensitizers, for example Janus green, rose Bengal and/or methylene blue may be used. Examples of known photo-sensitizers that may be used in accordance with some embodiments of the present invention are described in U.S. Pat. Nos. 5,552,452; 6,607,522; and 7,077,839.

Table 1 shows examples of photosensitizers and laser sources that may be used.

TABLE 1

| Photosensitizer | Laser Source | Wavelength |
| --- | --- | --- |
| Riboflavin-5-phosphate | Argon | 488-514 nm |
| Rose Bengal | Krypton Red | 600-670 nm |
| Porphyrins | Argon/Krypton/ | 488-514 |
| | Tunable Dye Lasers | 546, 600-670 nm |

Table 1 is merely an example of some of the electromagnetic radiation wavelength that may be used to achieve photo-activation, which may generally have a wavelength from about 10 nm to about 700 nm and will be within the visual, infra red or ultra violet spectra. The radiation may be supplied in the form of a monochromatic laser beam or other form of electromagnetic radiation source. The choice of energy source can be made in conjunction with the choice of photo-sensitizer employed in the composition. For example, an argon laser may be particularly suitable for use with flavins such as riboflavin-5-phosphate, i.e., flavins are optimally excited at wavelengths corresponding to the wavelength of the radiation emitted by the argon laser. For similar reasons, a diode laser can be suitable for use with chlorophylls such as bacteriochlorophyll A.

There are at least two major types of sensitized photo ¬ oxidative process, for example Type I and Type II. The sensitizer in its ground state can first absorbs light energy to form $S_x$ and $T_x$ which may comprise sensitizer molecules in their excited singlet and triplet states, respectively. Both Type I and Type II reactions can then proceed via the triplet state because it has a much longer lifetime than the singlet state.

In many Type I reactions, the sensitizer triplet T^ can then directly bind to the substrate to produce substrate free radicals or radical anions. The substrate radicals then can undergo further reactions, including that with molecular oxygen to form the superoxide anion $O_2$-. The superoxide anion then can react in numerous ways. For example, the superoxide anion can further react to generate hydrogen peroxide ($H_2O_2$) and the hydroxyl radical (OH*).

In Type II reactions, the sensitizer triplet may react first with molecular oxygen to produce singlet oxygen ($^1O_2$). The singlet oxygen can then oxidize the substrate to form photo-oxidation products. Direct electron transfer from triplet to oxygen can also occur to yield superoxide anions, but in some instances much less efficiently.

Photosensitizers can then cause oxidative damage to susceptible amino acid residues, for example histidine, tryptophan, tyrosine, cysteine, and methionine. They may cause non-disulfide covalent cross-links in susceptible proteins. This process can be oxygen dependent and may be mediated by singlet oxygen rather than by superoxide anions, hydrogen peroxide, or hydroxyl radicals. Natural collagen can be devoid of disulfide bridges Embodiments of the present invention enable one to produce non-disulfide covalent cross-links within collagen when exposed to light so to adhere an onlay to the stroma and/or Bowman's membrane.

In at least some embodiments of the present invention, water soluble photosensitizers that have high quantum efficiency for singlet oxygen production can be selected. These photosensitizers may include rose bengal (excited by the argon laser), riboflavin-5-phosphate (argon laser), porphyrins (argon/krypton) and methylene blue (krypton laser). The photosensitizer can then be mixed with a protein solder, applied to the wound, and exposed to the appropriate laser. An 18% fibrinogen solution may have the right consistency for ease of application and dissolved all photosensitizers without problem. Welded fibrinogen may resorb in vivo (Chuck R, Oz M C, Delohery T M, et al. "Dye-enhanced laser tissue welding." Lasers Surg Med. 1989; 9:471-477), and may be a good substrate for an organic glue in embodiments where resorbtion is used such that the onlay is temporarily adhered with the adhesive, for example prior to integration and/or re-epithelialization. Other proteins that may be used in accordance with embodiments of the present invention include albumin, zyplast collagen, myoglobin, glutathione, acid soluble collagen, $/3_H$ crystalline β crystallin and lysine, at various concentrations and in combinations with each other and with various photosensitizers and salts. For a more complete list of formulations, see Table 2, which shows protein and photosensitizer combinations that may be used.

TABLE 2

Protein and photosensitizer combinations.

PROTEIN/PHOTOSENSITIZER MIXTURES

Saline + Fluorescein isothiocyanate
Saline + Fluorescein isothiocyanate + HC03
25% Albumin + Fluorescein isothiocyanate
25% Albumin + Fluorescein isothiocyanate (1 1) + HA (1:1)
25% Albumin + Fluorescein isothiocyanate (1 1) + HC03**
25% Albumin + Fluorescein isothiocyanate (1 1) + HC03 + HA (1:1)
25% Albumin + Fluorescein isothiocyanate (10:1) + HC03
25% Albumin + Fluorescein isothiocyanate (10:1) + HC03 +HA
25% Albumin + Fluorescein isothiocyanate (1 1) + HC03 + 20% ETOH
25% Albumin + Fluorescein isothiocyanate (1 1) + HC03 + 50% ETOH
25% Albumin + Fluorescein
25% Albumin + Fluorescein + HA
Zyplast (collagen) + 10% Fluorescein
Zyplast + Saline + HC03 + Fluorescein isothiocyanate
Zyplast + Saline + HC03 + Fluorescein isothiocyanate + HA
35% Albumin + Fluorescein
35% Albumin + Fluorescein + HA
35% Albumin + Fluorescein isothiocyanate (1 1) +

TABLE 2-continued

Protein and photosensitizer combinations.

PROTEIN/PHOTOSENSITIZER MIXTURES

HC03 + 20% ETOH
35% Albumin + Fluorescein isothiocyanate (1 1) +
HC03 + 10% ETOH
35% Albumin + Red # 40**
35% Albumin + Yellow #6
50% Albumin (fatty acid, globulin free) +
Fluorescein isothiocyanate (1:1) + Saline + HC03
50% Albumin +Fluorescein isothiocyanate (1 1) + HC03 + 10% ETOH
50% Albumin + 10% ETOH
44% Myoglobin + Saline
44% Myoglobin + Saline + HA
10% Myoglobin + Saline
10% Myoglobin + Saline + HA
1% Myoglobin + Saline 1% Myoglobin + Saline + HA
5 uM Myoglobin (1:1 with Albumin) + 25% Albumin 10 uM Myoglobin
(2:1 with Albumin) + 25% Albumin
5 mm Glutathione + Saline + Fluorescein isothiocyanate + HC03 +
HA 50 mm Glutathione + Saline + Fluorescein isothiocyanate + HC03 + HA
5 mm Glutathione (1:1) + 35% Albumin +
Fluorescein isothiocyanate + HC03
5 mm Glutathione + 35% Albumin + Fluorescein isothiocyanate +
HC03 + HA
55 mg Glutathione (70:1) + 35% Albumin +
Fluorescein isothiocyanate + HC03
50 mm Glutathione + 35' Albumin + Fluorescein isothiocyanate +
HC03 50 mm Glutathione + 35' Albumin + Fluorescein isothiocyanate +
HC03 ■ HA
HA + Saline + Fluorescein isothiocyanate + HC03
Rose Bengal (2 mM) + 35% Albumin Rose Bengal (0.2 mM) +
35% Albumin Rose Bengal (0.02 mM) + 35% Albumin Rose
Bengal (20 uM) + 35% Albumin** Rose Bengal (2 uM) +
35% Albumin Rose Bengal (8 mM) Rose Bengal (1 mM)
Methylene Blue (500 uM) + 35% Albumin + Argon Laser
Methylene Blue (500 uM) + 35% Albumin + Krypton Laser
Methylene Blue (50 uM) + 35% Albumin + Krypton Laser
Methylene Blue (5 uM) + 35% Albumin + Krypton Laser
2% Collagen (from Calf Tendon, dissolved in acetic acid) + Rose Bengal
(1:1) (Ph adjusted to 9 with NaOH)
3.8% Fibrinogen + De-ionized H20 + Rose Bengal (Ph adjusted)
BH Crystallin + De I H20 + RB + NaOH BL Crystallin +
De I H20 + RB + NaOH
Collagen (1.7%) + Riboflavin-5-Phosphate (R5P) (Ph adjusted)
Collagen (1.7%) + (R5P) (Ph adjusted) + Glutathione (70:1)
3.8% Fibrinogen + R5P
3.8% Fibrinogen + R5P + Glutathione (70:1)
18% Fibrinogen + R5P (1:1)
18% Fibrinogen + R5P (10:1)**
18% Fibrinogen + R5P (10:1) + Na Azide
18% Fibrinogen + Fluorescein isothiocyanate + HC03**
18% Fibrinogen + Fluorescein isothiocyanate + HC03 + R5P (10:1)
Lysine + 18% Fibrinogen + R5P (10:1) Lysine + De I H20 + R5P (10:1)

Table 2 shows examples of photosensitizers that may be used and empirical experiments can be performed on a suitable number of animals and/or patients to determine appropriate characteristics to adhere and/or cure the onlay on the exposed surface of the stroma and/or Bowman's membrane. The photosensitizers of Table 2 can be combined with many of the onlay materials described and/or adhesives described herein to form a material suitable for adhesion to the stroma and/or Bowman's membrane.

FIG. 3B1 shows adhesion of onlay 100 as in FIG. 2A with tissue welding to hold the onlay in place while the adhesive sets. A photosensitizer may be disposed under the onlay and tack welded with laser and/or other light to weld the onlay to the tissue. In some embodiments, and additional adhesive may be employed, for example delivered with a deliver tool near the periphery of the onlay. The tack welds comprising dots 314 can hold the onlay in place while the adhesive sets.

In some embodiments, an annular track of adhesive may be disposed on the onlay as described above, and used with tack welding of the onlay with light. A delivery tool 316 may be used to deliver the adhesive.

III. C. Protein Crosslinking Agents

FIGS. 3C and 3C1 show adhesion of an onlay as in FIG. 2A with a protein cross-linking agent 330. Many protein cross-linking agents may be used, for example adhesives as described above. In some embodiments, a heterobifunctional with photo activated group and a cross-linking group can be employed so as to cross-link the onlay to the Bowman's membrane and/or stroma with covalent bonds in response to photo activation with an appropriate flux. In some embodiments, the cross-linking agent may crosslink the onlay to Bowman's membrane and/or the stroma without photo activation.

III. D. Application of Adhesive

FIG. 3D shows application 318 of adhesive 310 to an onlay as in FIG. 2A. The adhesive can be applied in many ways. The adhesive may be applied to a peripheral portion of the onlay, for example with an annular geometry to promote vision with a central portion of the onlay. The adhesive may be applied as a drop, a ring and or a spray. Known electrospray aerosol generators can be used to generate nanoparticles of adhesive, for example an known electrospray generator available TSI capable of generating 3 nm particles with a density as high as $10^7$ particles per $cm^3$. The adhesive may be applied in many patterns, for example annular dots along a circumference, and may soak into the onlay.

FIG. 3D1 shows a double sided sticky tape 315 comprising adhesive suitable for use with an onlay. The adhesive may comprise a biocompatible material formed as a sheet with an adhesive disposed on either side of the sheet.

The anterior side of the onlay may comprise the biocompatible material of the onlay so as to promote epithelialization, for example collagen and/or collagen based material. An agent to inhibit epithelialization under the onlay may be disposed under the onlay on the posterior surface. The agent to inhibit epithelialization under the onlay may comprise at least one of an immunosuppressant, for example, cyclosporine, an anti-hyperproliferative, for example 5-fluorouracil, and an anti-inflammatory, for example a steroid.

The adhesive may comprise a two component system. A first component may comprise protein and/or a prepolymer component. The protein may comprise, for example, fibrinogen, and the prepolymer may comprise, for example polyethylene glycol. A second component may comprise a catalyst and/or a cross-linker, for example glutaraldehyde. The onlay may be soaked in the protein and/or prepolymer, and the catalyst and/or cross-linker may be applied to the exposed tissue of the eye, for example the stroma and/or Bowman's. The onlay can then be positioned on the exposed tissue such that the first component reacts with the second component so as to adhere the onlay to the exposed tissue. In some embodiments, the onlay may be soaked in the catalyst and/or cross-linker, and the protein and/or pre-polymer applied to the exposed tissue, for example the stroma and/or Bowman's. The onlay can then be placed on the eye. At least one of the first component or the second component may comprise a photosensitizer for tissue welding and/or photoactivated curing.

The onlay can be shaped in many ways to adhere the onlay to the cornea. The onlay may comprise a central optical portion, a transition portion extending from the optical portion and a peripheral portion to adhere the onlay. The transition portion may extend over the optically used portion of the cornea, for example over the pupil, so as to at least one of inhibit or minimize aberrations and provide the intended optical effect of the optical portion. The peripheral portion may extend over the non-optically used portion of the cornea, for example away from the pupil, so as to at least one of inhibit or minimize interference of the peripheral portion with patient vision. The cornea may be debrided to a size, for example a diameter, larger than the optical zone. The debrided area may be at least 1 mm greater size than the optical zone, for example 2 mm diameter greater, such that the onlay can be adhered to the cornea with a size greater than the optical zone to promote adhesion.

FIG. 3D2 shows an onlay shaped to cover at least a portion of the conjunctiva. In some embodiments, the peripheral portion PP can extend so as to cover at least a portion of the conjunctiva, and can be adhered and/or anchored to the conjunctive with the methods, adhesives and/or structures as described herein. The onlay may comprise a central potion CP and a transitional portion TP disposed between the peripheral portion and the central portion.

III. E. Micro-Shape Corneal Tissue and Material to Adhere to Each Other

FIG. 3E shows microshaped corneal tissue to adhere an onlay as in FIG. 2A. The corneal tissue may be microshaped in many ways, for example with a femtosecond laser. The onlay 100 can comprise a microshaped onlay surface 342, and the cornea 20 can comprise a microshaped corneal tissue surface 340. Work in relation to embodiments of the present invention indicates that microshaping of the onlay and/or recipient Bowman's and/or stroma can provide adhesion. In some embodiments, the surface of the recipient cornea may be ablated and/or treated with a femtosecond laser so as to microfinish the surface with roughness, for example from disrupted collagen fibers of Bowman's and/or the corneal stroma. In some embodiments, a thin layer comprising at least a portion of Bowman's membrane may be perforated with the femtosecond laser and removed. The onlay can be treated with the femtosecond laser to roughen the surface so as to disrupt polymer chains of the onlay material, for example collagen fibers, so as to adhere the onlay to Bowman's and/or the stroma. In some embodiments both the posterior surface of the onlay and the Bowman's and/or stroma can be treated with the femtosecond laser so as to provide a microfinish and/or roughness on both surfaces. Microfinishing may provide increased surface area so as to adhere the onlay to the stroma and/or Bowman's with Van der Waals forces.

The onlay may comprise barrier to water penetration, for example a natural epithelium, such that the endothelium can maintain corneal deturgescence when the onlay is positioned on the eye. In some embodiments, endothelial pumping of water from the cornea may provide adhesion of the onlay to the stroma when the anterior surface of the onlay and the cornea comprises a water barrier, or minimizes water penetration, for example with a seal, such that the endothelial pumping of water sucks the onlay into position.

FIG. 3E1 shows microshaping comprising interlocking structures 344 to adhere an onlay as in FIG. 3E. The interlocking structures 344 may comprise barbs, hooks, and/or protrusions extending from a base on the posterior surface 120 of the onlay to an enlarged distal end. The interlocking structures can extend into the anterior exposed corneal surface 20ES.

FIG. 3E2 shows nano structures 346 to adhere an onlay as in FIG. 3E to an anterior corneal surface 20S. The nanostructures may comprise many structures, for protrusions and indentations such as castellation. In some embodiments, the nanostructures may comprise setae and/or fibers with spatulas on the end, so as to increase surface area and provide charge on the nano-structure of the onlay and/or cornea, for example with Van der Waals forces. Nano structures with adhesive properties suitable for incorporation in accordance with some embodiments of the present invention are described in U.S. Pat. No. 7,229,685. Such nano structures can be provided on the onlay and/or the cornea to adhere the onlay to the cornea. The nanostructures can be disposed on a peripheral portion of the onlay disposed away from a central vision correcting portion of the onlay.

III. F. Charge on Implant and Cornea

FIG. 3F shows charge to adhere an onlay as in FIG. 2A. Charge 350 on the posterior surface of the onlay and charge 352 on the surface of cornea can adhere the cornea to the onlay. Work in relation to embodiments of the present invention suggests that disruption of collagen fibers, for example with a femtosecond laser can provide charge to promote adhesion. Chemical treatment and/or scintillation may also be employed to promote adhesion of the onlay and cornea with charge. In some embodiments, the charge may comprise intermolecular forces, for example Van der Waals forces at the interface between the onlay and the Bowman's membrane and/or stroma.

III. G. Cutting, Ablating and/or Abrading the Cornea to Receive the Onlay

FIG. 3G shows cutting and/or abrading to adhere an onlay as in FIG. 2A. The cutting tool comprises an abrading/cutting surface. The cutting tool can be moved with rotation 356. An annular zone of Bowman's membrane can be cut and/or abraded to adhere the onlay to Bowman's membrane and/or the stroma. In some embodiments, a bed in the recipient cornea can be prepared with a femtosecond laser, for example similar to removal of a button of donor tissue, so as to provide a smooth transition of the corneal surface at the peripheral boundary of the onlay and the cornea.

FIG. 3G1 shows surgical tucking of the onlay into the stroma and/or Bowman's membrane. The onlay comprises anterior surface 110 and posterior surface 220. The anterior surface can be shaped for optical correction, as described above, and the posterior surface can be shaped to fit the anterior surface of the stroma and/or Bowman's membrane. The posterior surface may comprise a central portion shaped to fig along the anterior surface of Bowman's membrane and a peripheral portion shaped to fit into an excision and/or excision of the cornea. The peripheral portion of the onlay may comprise a flange, for example an annular flange 362, shaped to extend into an excision and/or excision 364 in the stroma and/or Bowman's membrane, for example under a flap 360 of tissue comprising Bowman's membrane. In some embodiments the incision and/or excision may comprise an annular incision shape to receive the peripheral portion of the onlay. Tissue along the incision and/or excision may be excised, for example removed with ablation, such that the incision and/or excision is shaped to receive flange such that the flange fits under the flap. The flap may comprise epithelial tissue along the anterior surface.

An adhesive, as described above, may adhere the onlay to the cornea. The adhesive may comprise a photosensitizer such that the flange can be adhered to the stroma and/or Bowman's under the flap, for example with irradiation after the onlay has been positioned and/or aligned on the eye. The flange can be adhered and/or welded to the flap with the irradiation.

The adhesive may comprise a reversible adhesive that can melt when the removal agent is applied, as described above. The removable adhesive may comprise a photosensitizer such that the onlay can be adhered to the eye with a light beam when the onlay is aligned with the eye, and the onlay can be removed, if desired, with application of the tissue removal agent.

FIG. 3G2 shows incision in tissue of the cornea to prepare to cornea as in FIG. 3G1. The tissue can be configured for excision 368. The incision can be formed with a laser beam, for example femtosecond laser beam 366, and may be formed with a mechanical tool such as a scalpel.

Figures 3, 3J:
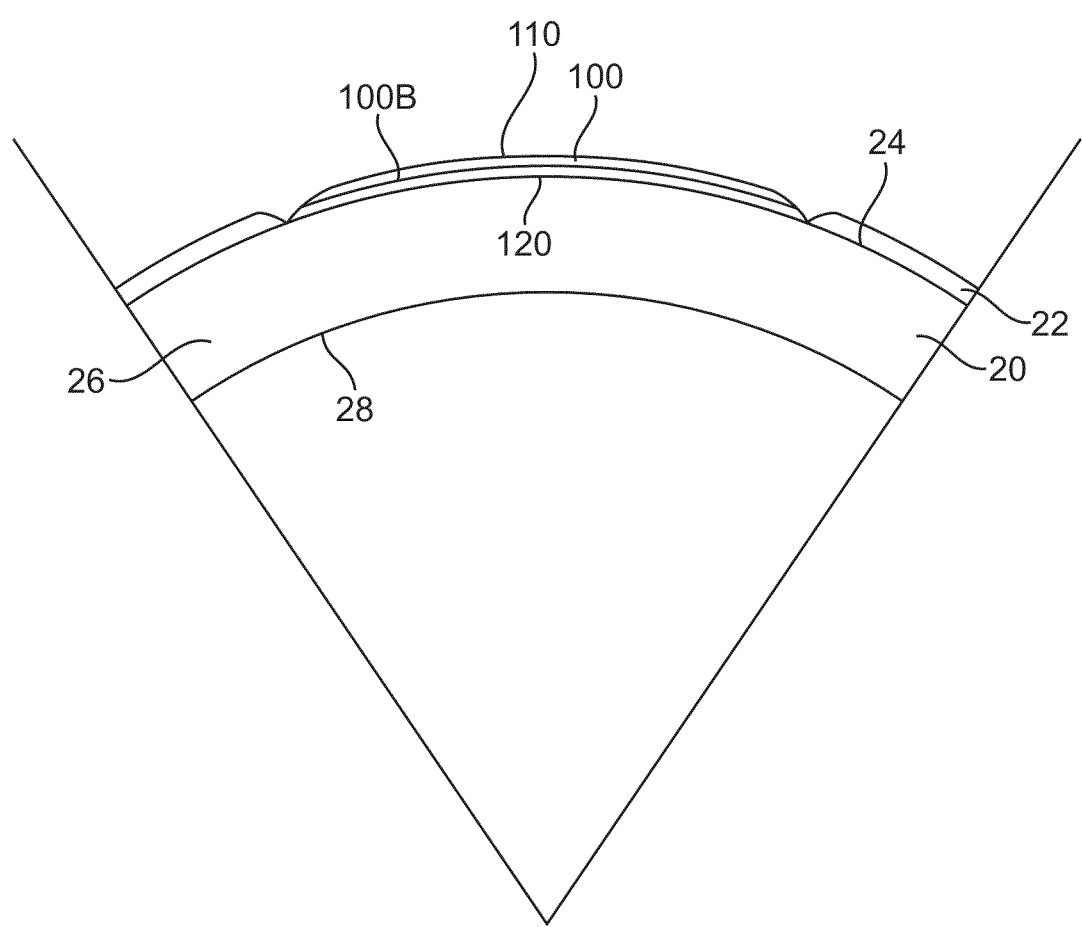

FIG. 3G3 shows an excision profile 369 in tissue of the cornea shaped to receive an onlay. The excision may comprise at least a portion of Bowman's membrane, and can comprise a uniform depth 369D. The excision may comprise steep walls and be shaped to receive the onlay. For example, the onlay may comprise a rim 100R that extends circumferentially around the onlay, and the excision may comprise an annular boundary shaped to receive the rim of the onlay with a diameter that is slightly larger than a diameter of the onlay. The excision profile may comprise a peripheral depth from the anterior surface of Bowman's membrane into the Bowman's membrane and/or stroma that corresponds to a peripheral thickness 100PT of the onlay, for example when the onlay is provided without an epithelium. The excision profile may comprise a peripheral depth from the anterior surface of the epithelium into the Bowman's membrane and/or stroma that corresponds to a peripheral thickness of the onlay, for example when the onlay is provided with an epithelium.

III. H. Integration of Implant Matrix with Host Cornea

FIGS. 3H and 3H1 show integration of the implant matrix with the host cornea. FIG. 3H illustrates the onlay in the immediate post-operative period prior to integration with the cornea. In many embodiments, the onlay material comprises a material capable of integration with the recipient cornea. The onlay material may integrate with the stromal tissue, such that onlay material adheres to the stromal tissue and/or Bowman's membrane. Integration of an onlay is described in U.S. 20060134170. Such onlay materials can be incorporated with the methods and devices described herein so as to integrate the onlay with the cornea once the onlay is adhered to the cornea and epithelialization of the onlay has occurred. Integration of the onlay may extend from the stroma and/or Bowman's into the onlay along an integration zone 201.

III. I. Mechanical Adhesion with Anchors

FIG. 3I1 shows a bottom view of an onlay with anchors comprising bioadhesive tacks 370 used to adhere the onlay to the cornea. Although four tacks are shown, as many tacks as are useful may be used, for example from one tack to about 20 tacks may be used. Each tack may comprise a base 372 and extend from the base to the tip 374. Each tack may comprise a barb 376 to anchor the tack in the tissue and can penetrate as far the epithelium, the Bowman's membrane, or the stroma. The onlay may comprise an inner portion, for example a central optical portion 10000P with optical correction, and the tacks may be disposed in an outer portion, for example peripheral portion 100PP of the onlay to adhere the onlay to the cornea.

FIG. 3I2 shows a side view of the onlay as in FIG. 3I1. Although shown extending normal to the surface, the tack may extend at any angle between 0 and 180 degrees relative to the bottom surface of the tack for example inclined centrally or peripherally. Each tack can extend normal to the surface and may be inclined relative to the surface.

The tack may comprise many materials. The tack may comprise a bioerodible material, such that the tack adheres the onlay to the cornea for a period of time, for example when the epithelium regenerates over the onlay, and then erodes sufficiently so as to break and release the onlay from the cornea after the epithelium has grown over the onlay. Many bioerodible materials can be used including poly lactic acid (hereinafter "PLA"). After the epithelium is regenerated, the material can erode sufficiently to release the onlay such that the onlay is adhered to the cornea with natural biological processes, for example with the epithelium and/or collagen deposition at the interface between the onlay and the stroma and/or Bowman's membrane. The tack can be configured to erode after at least three days, for example after at least one week. Alternatively, the tack may comprise a shape memory material, for example, Nitinol or a temperature sensitive shape memory alloy. The shape memory material may facilitate the removal of the onlay by allowing the tacks to straighten under certain conditions.

III. J. Adhesion with Suction

As noted above, the onlay may comprise a degradable barrier to water penetration, such that the endothelium can maintain corneal deturgescence when the onlay is positioned on the eye. The water inhibiting layer can degrade when the epithelium has regenerated over the onlay, such that nutrients can pass to the epithelium from the cornea through the onlay. In some embodiments, endothelial pumping of water from the cornea may provide adhesion of the onlay to the stroma when the anterior surface of the onlay and the cornea comprises a water barrier to inhibit water penetration, or even minimize water penetration, for example with a seal, such that the endothelial pumping of water sucks the onlay into position. The water barrier may comprise many known materials that inhibit the flow of water.

The water barrier layer may comprise a monolayer of molecules and may comprise a thickness within a range from about 1 nm to about 100 um. The water barrier may extend substantially across the thickness of the onlay. For example, the onlay may comprise a water barrier material, such as silicone. The water barrier material can be coated on one or more sides with a hydrophilic coating. The hydrophilic coating may comprise many of the coatings described herein for example a lubricous coating.

FIG. 3J-1 shows a degradable water inhibiting barrier layer 100B disposed on an upper side along anterior surface 110 of onlay 100. The water barrier may be coated with a hydrophilic layer along the upper surface. The placement of the water barrier along the upper side of the onlay 100 can form a seal along the epithelium extending over the onlay, such that the onlay can adhere to the Bowman's membrane of the cornea with suction when the epithelium regenerates over the anterior surface of the onlay. The material below the water barrier may comprise a material that allows nerve growth, for example collagen, such that nerve fibers can grow into the onlay. The water inhibiting layer may comprise a degradable barrier material such as PLA, PGA, or PLA/PGA copolymer, configured to degrade within about a week after placement on the cornea, for example within about 3 days. The barrier material may comprise a biodegradable and erorable suture material disposed on the onlay to inhibit water penetration as noted above.

FIG. 3J-2 shows degradable water inhibiting barrier layer 100B disposed on a lower side of an onlay. The water barrier may extend to the periphery of the onlay along the posterior surface of the onlay, so as to form a seal with the epithelium near the lower surface of the onlay, such that the onlay can adhere to the Bowman's membrane of the cornea with suction.

FIG. 3J-3 shows degradable water inhibiting barrier layer 100B disposed along on an inner layer of an onlay. The water barrier may extend to an outer periphery of the onlay to form a seal with the epithelium, such that the onlay can adhere to the Bowman's membrane of the cornea with suction.

IV. Shaping of Material

The corneal onlays described herein may be shaped in many ways, for example with molding, jet deposition and/or laser ablation. The material may be shaped with a complex shape, for example a wavefront derived shape, so as to correct lower order aberrations (sphere and cylinder) and high order aberrations such as coma and spherical aberration. The material may be shaped by deposition of particles. For example, known electrospray aerosol generators can be used to generate nanoparticles, for example an known electrospray generator available TSI capable of generating 3 nm particles with a density as high as $10^7$ particles per $.cm^3$. The material can be applied as a drop of liquid, for example from a syringe, that spreads along the prepared surface of the cornea and can be molded with a mold, for example a light transmitting mold to permit curing and/or welding of the lens.

IV. A. Molding

Figure 4A:
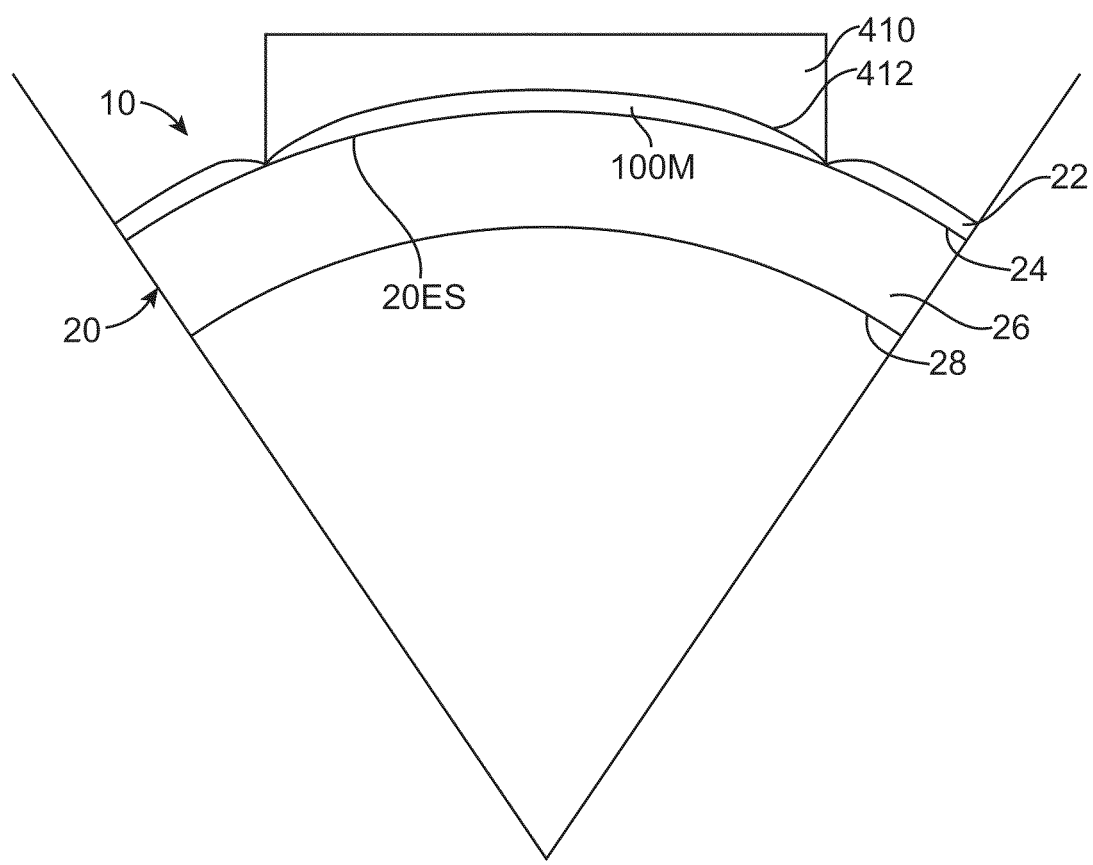
FIG. 4A shows in situ molding of the onlay lens on the exposed corneal surface, according to embodiments of the present invention.

FIG. 4A shows in situ molding of the onlay lens on the exposed corneal surface 20ES. The mold 410 can be positioned on the exposed Bowman's membrane and/or stromal surface. The mold 410 comprises a mold surface 412. After the lens material 100 M is cured, the mold can be removed. The lens materials, adhesives and/or photosensitizers as described above, can be used with the molds and adhered to the exposed surface of Bowman's membrane and/or the stroma, for example as described above. In some embodiments, the mold may comprise an optically transparent material so as to allow photo activation and/or welding of the lens to the Bowman's membrane and/or stroma. The lens may be molded in situ on the stroma and/or Bowman's membrane, with known molds, for example with molds as described in U.S. Pat. Nos. 4,983,181; 4,994,081 5,114,627; 5,163,596; and 6,055,990. In some embodiments, the mold may comprise a contact lens, for example a high water content contact lens. The mold may comprise a polished surface, a PTFE coating and/or known low adhesion and/or low frication surfaces, such that the mold comprising the contact lens can be removed from onlay when the layer is adhered and/or cured to the anterior stroma and/or Bowman's membrane. The light transmitting mold can allow the surgeon to align the mold with the eye. When the mold is aligned with the eye, the surgeon can activate a light source so as to cure and/or weld the onlay material in situ on the cornea so as to adhere the onlay to the stroma and/or Bowman's membrane.

The onlay may be molded prior to placement on the cornea with materials as described above, and the onlay may be adhered to the cornea as described above.

IV. B. Jet Deposition Process

Figure 4B:
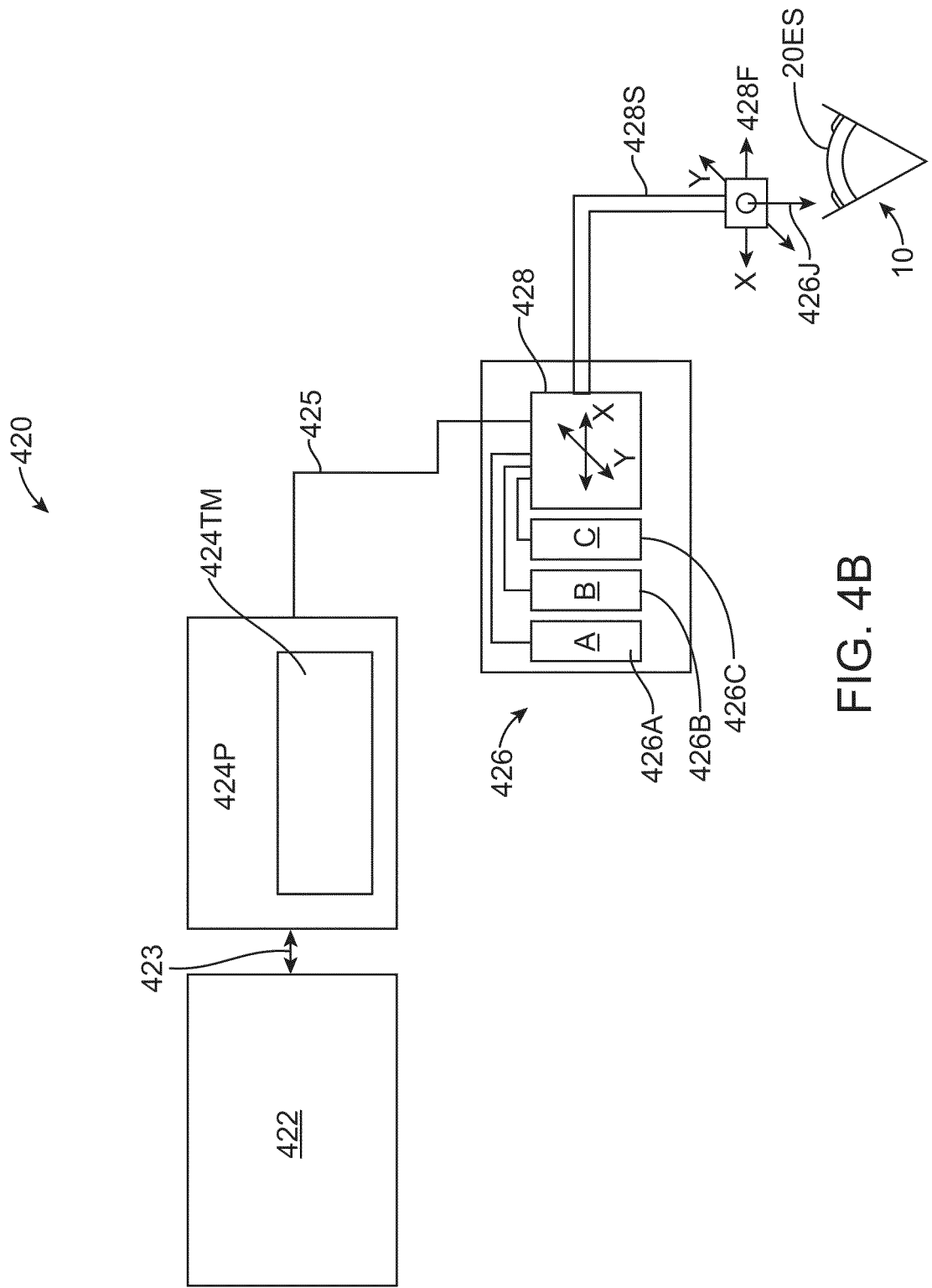
FIG. 4B shows a jet deposition system and process to form on onlay according to embodiments of the present invention.

FIG. 4B shows a deposition system 420 comprising a jet 426 and process that may be used to form on onlay in situ on an exposed corneal surface. The system may also be used to form custom onlays on a substrate for subsequent placement on the Bowman's and/or stroma. The system may comprise a wavefront system 422, a processor 424P, and jet forming device. An input device, for example comprising the eye wavefront measurement system can be used to determine a target shape of the onlay. Refractive data, for example patient refraction data, can also be used to define the target shape. The processor is capable of communication 423 with wavefront device and processor, such that the processor can receive the wavefront data. The processor comprises a tangible medium 424™ with instructions for the processor stored thereon. A control line 425 may extend from the processor to a jet deposition apparatus, similar to many known ink jet deposition apparatus. The jet deposition apparatus may comprise at least one cartridge 426, a drive mechanism 428, and a jet forming structure 428F. A support 428F extends between the jet forming structure and the drive mechanism. The at least one cartridge may comprise three cartridges for example cartridge 426A, cartridge 426B and cartridge 426C. Each cartridge may comprise components for forming the onlay, for example components of the adhesives and/or materials as described above. The drive mechanism may move the jet forming structure, so as to control the position of the jet on the eye, such that the jet can be scanned over the eye under computer along at least two directions, for example X and Y directions along the exposed surface. The jet may comprise a pulsed jet comprising the material from one of the cartridges. A sequence of pulsed jets comprising the material from the cartridges can be sequentially applied to the exposed surface of the cornea so as to form the onlay with the desired shape, for example the wavefront derived shape on the eye.

The jet may apply micro particles of collagen. The at least one cartridge may comprise a collagen cartridge similar to a cartridge for a printer. A first cartridge, for example cartridge A, and a second cartridge, for example cartridge B, may comprise components of a two component system in which the first part comprises protein second part curing agent. The jet deposition apparatus can build up the onlay over time and sputter the onlay material onto the exposed surface so as to form the onlay lens. The lens can be fabricated in situ on the eye. A third cartridge may comprise a photosensitizer. The photosensitizer can be applied with the jet to provide the photosensitizer at a level of the deposition to cure the lens and/or adhere the lens to the stroma with light activation. A light beam can be used to cure the material comprising the photo sensitizer and/or the first two components, for example first two components from cartridge A and cartridge B, respectively. In some embodiments, the lens may be fabricated on a support substrate, for example at fabrication center, similar to semiconductor processing. The onlay may comprise a customized computer based shape profile, for example a three dimensional shape profile with X-Y coordinates.

IV. C. Laser Ablation

Figure 4C:
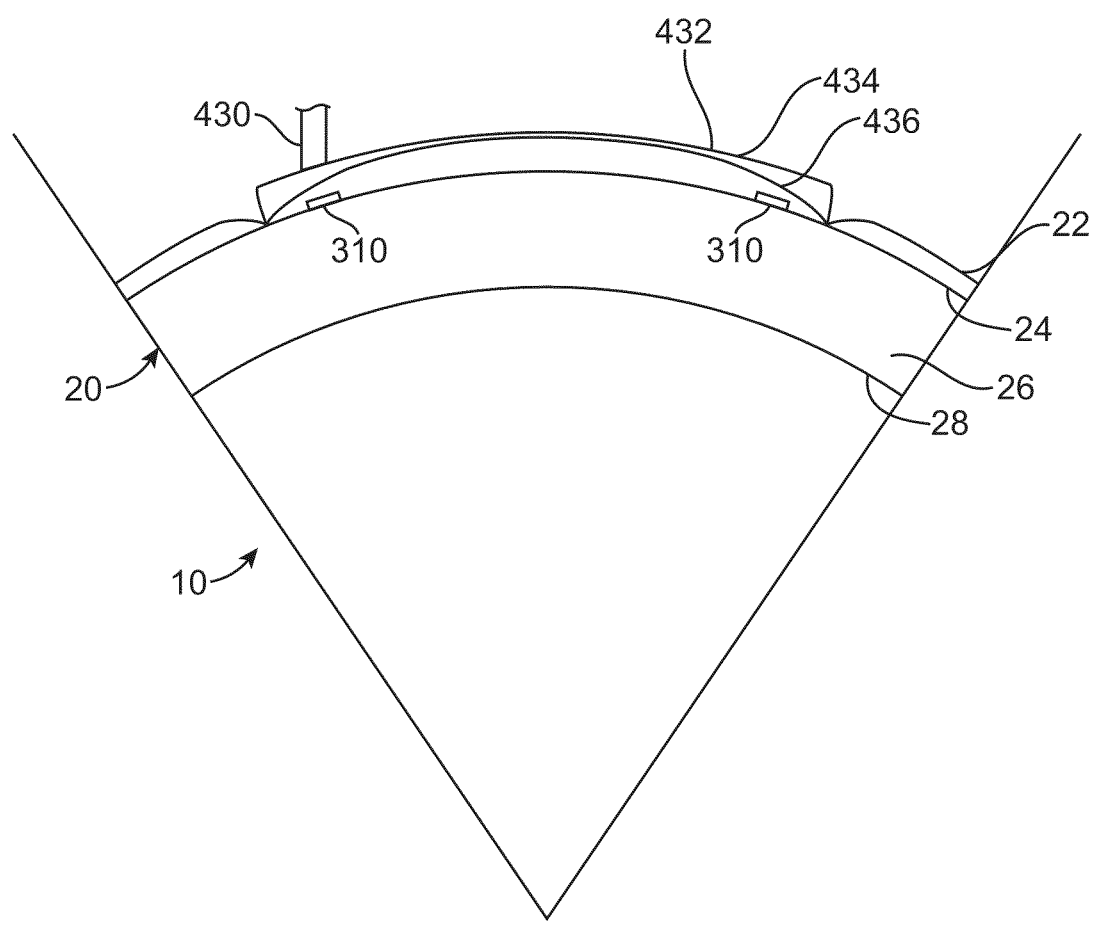
FIG. 4C shows laser ablation of an onlay, according to embodiments of the present invention.

FIG. 4C shows laser ablation of an onlay to shape the onlay to correct vision of the patient. The onlay may comprise a material, as described above, in the shape of a donor button, for example an epikeratophakia button 432 of substantially uniform thickness. The epikeratophakia button can be adhered to the eye as described above, for example with an adhesive. The onlay comprises an initial profile 434, for example a profile when adhered to the cornea. The excimer laser beam, for example a scanning excimer laser beam 430 can be used to ablate the onlay to an ablated profile 426 so as to correct vision of the patient.

FIG. 4C1 shows use of a femto second laser to make a button 432 as in FIG. 4C. A donor eye may comprise a donor cornea 432C, for example as described above. The donor cornea can be ablated with a femto second laser beam 366, for example known femto second lasers, so as to perforate and/or ablate the cornea with the shape of the onlay button, for example as shown in FIG. 4C. The onlay button can be removed from the donor cornea and adhered to the recipient cornea. The recipient cornea may be prepared to receive the donor onlay in many ways as described above, for example prepare with a micro-finishing.

IV. D. Wavefront Mapping for Shaping the Onlay

Figure 4D:
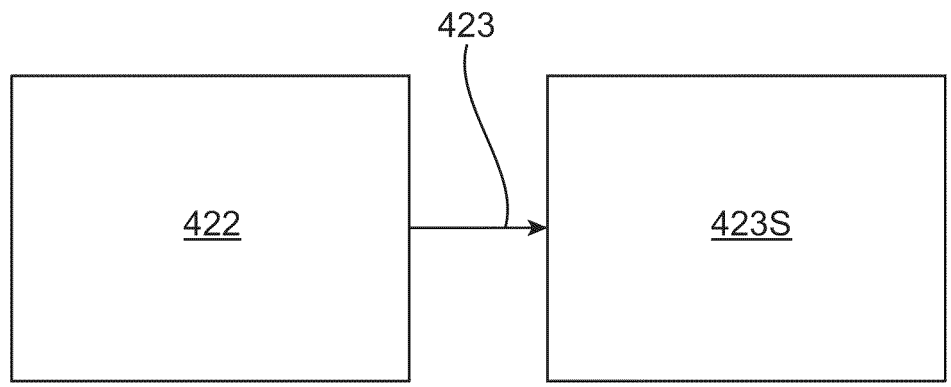
FIG. 4D shows synthesis of an onlay for correcting aberrations in response to a wavefront aberration measurement, according to embodiments of the present invention.

FIG. 4D shows synthesis of an onlay for correcting aberrations in response to a wavefront aberration measurement. The system comprises a wavefront system 422, an onlay shaping system 423S, and a communication system 423S therebetween. The desired onlay shape can be determined in many known ways to correct vision of the patient, for example with manifest refraction, cycloplegic refraction and/or wavefront measurement. The onlay may be formed and/or shaped as described above.

IV. E. Trans Epithelial Deposition Process

FIG. 4E shows an epithelium a penetrating deposition process 440 that deposits lens material through the epithelium to form a lens on and/or in Bowman's membrane and/or stroma. Bowman's membrane comprises an anterior surface 24AS and a posterior boundary 24PB that may be separated by a distance of about 10 um. The epithelium deposition process can include many known tattoo deposition processes used to tattoo skin. The epithelium penetrating deposition may deposit particles and/or molecules 442A on Bowman's membrane, inside Bowman's membrane 442B, under Bowman's membrane and/or in the corneal stroma 442C. The particles and/or molecules may comprise materials as described above so as to alter the shape and/or index of refraction of the cornea so as to correct vision of the patient. The particles and/or molecules can be deposited sub-epithelial so as to build up material in the stroma and/or Bowman's membrane and correct the vision of the patient. In some embodiments, the deposited particles and/or molecules can be removed with ultrasound and/or laser irradiation, similar to the removal of tattoos.

IV. F. Stereolithography Lens Fabrication

Figure 4F:
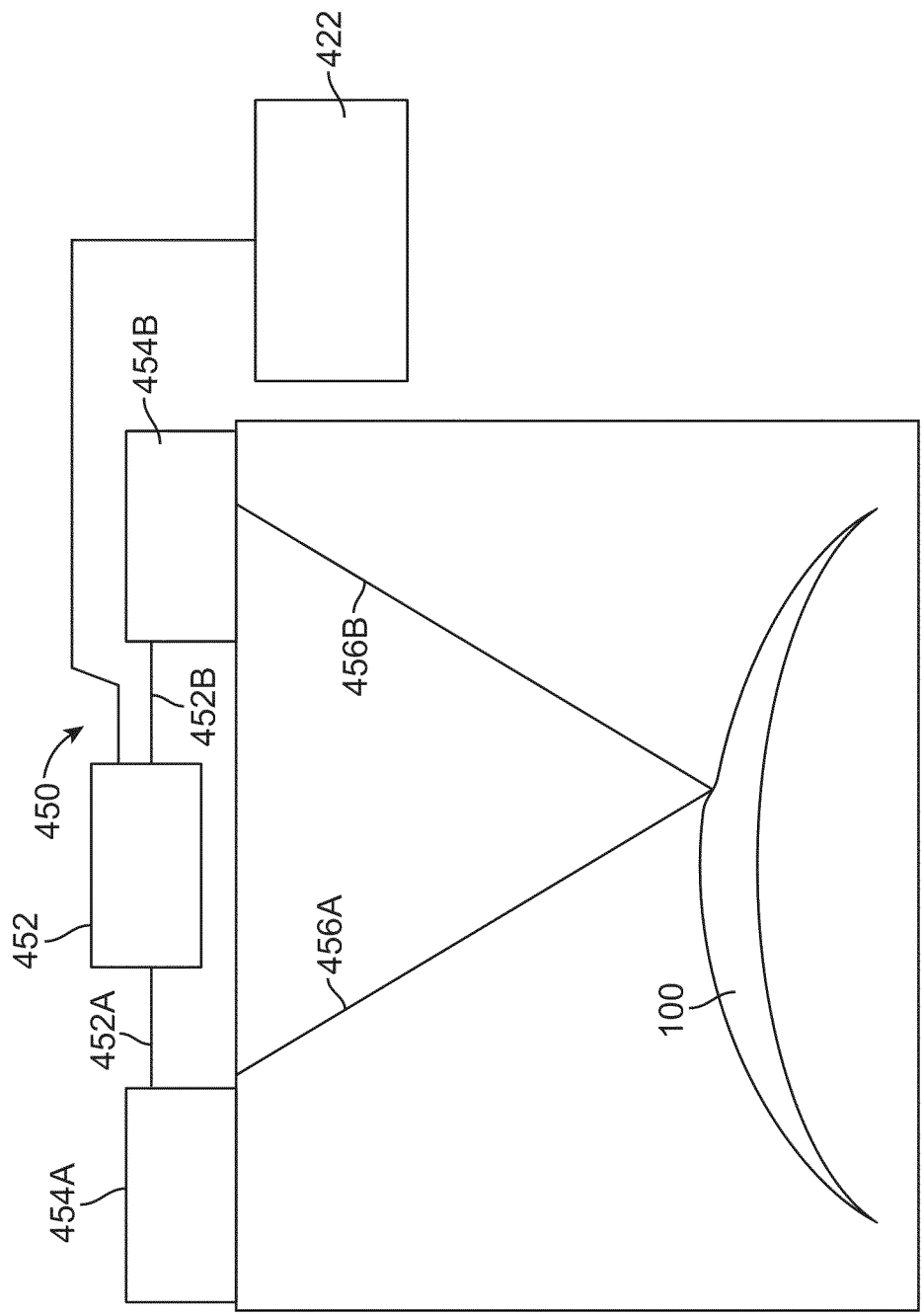
FIG. 4F shows stereo lithographic fabrication of an onlay lens, according to embodiments of the present invention.

FIG. 4F shows stereolithography to fabricate an onlay lens. The stereolithography system 450 may comprise many known stereolithography systems that incorporate the materials and/or photosensitizers as described above. The onlay 100 can be formed in a tank that retains a liquid such that the onlay can be formed where light beams 456A, 456B, are aligned. A wavefront from a wavefront measurement system 422 and/or patient refraction data can be used to determine the shape of the only. The stereolithography system (hereinafter "S.L.S.") comprises a controller 452 in communication with light source/scan modules 454A, 454B, to scan the light beams. The controller can align the light beams under computer control to fabricate the onlay.

V. Adhesion of Epithelium to Onlay

Figure 5A:
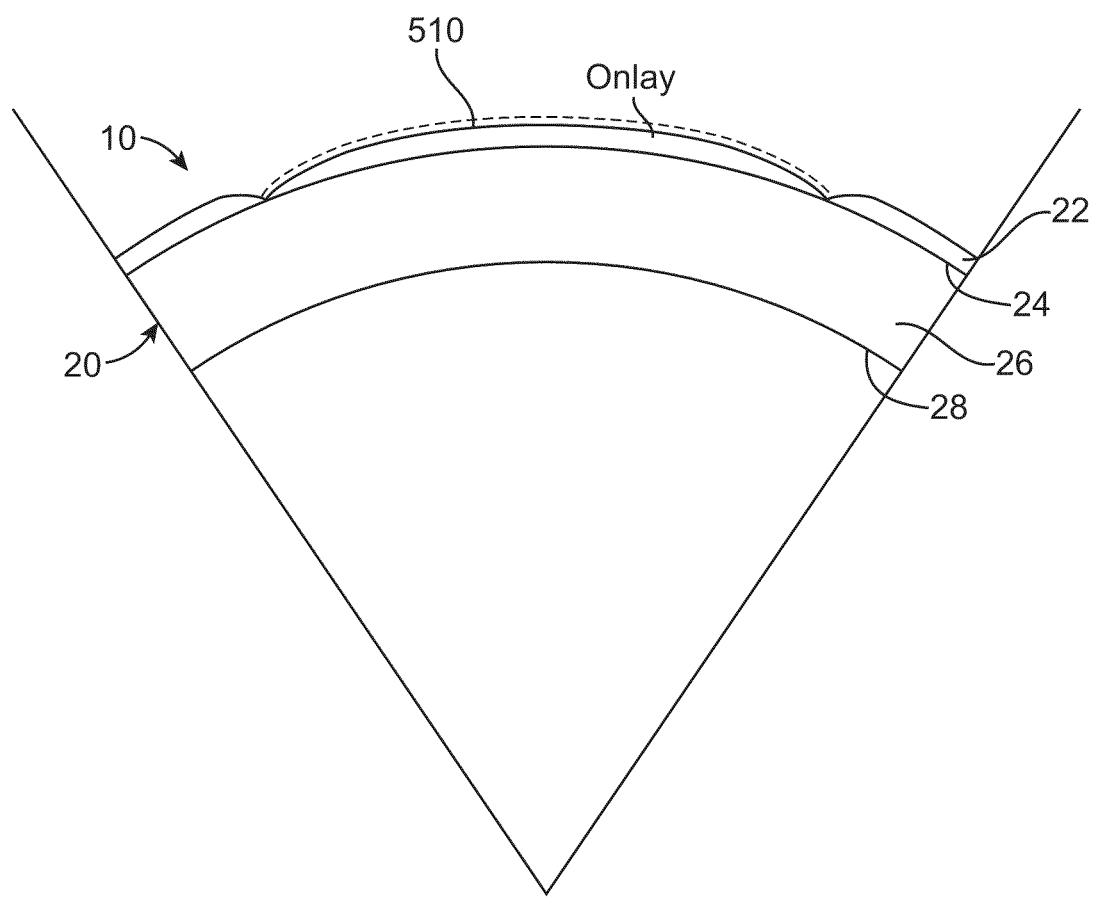
FIG. 5A shows an agent on an anterior surface of an onlay to promote epithelialization and adhesion of the epithelium to an onlay, according to embodiments of the present invention.

FIG. 5A shows an agent 510 on an anterior surface of an onlay to promote epithelialization and adhesion of the epithelium to an onlay. The anterior surface of the onlay may comprise known agents such to promote epithelialization such as tethered enhancer molecules, fibronectin and/or fibrinogen, photolysing of groups on the surface, photochemically reactive groups and/or photo treatment of the surface.

The onlay may comprise an adhesive, for example at targeted adhesive to adhere to the epithelium to the onlay, for example bioadhesives and/or mucoadhesive compositions to target adherence with the epithelium, for example as described in U.S. Pat. Nos. 5,814,329; 5,942,243 and 6,958, 148; and U.S. Pub No. 2004/0143026, the disclosures of which may be suitable for combination in accordance with some embodiments of the present invention. The onlay may comprise micro-particles to attached to the epithelium, for example with delivery agents as described in U.S. Pat. No. 6,958,158, the disclosure of which may be suitable for combination in accordance with some embodiments of the present invention.

Figure 5B:
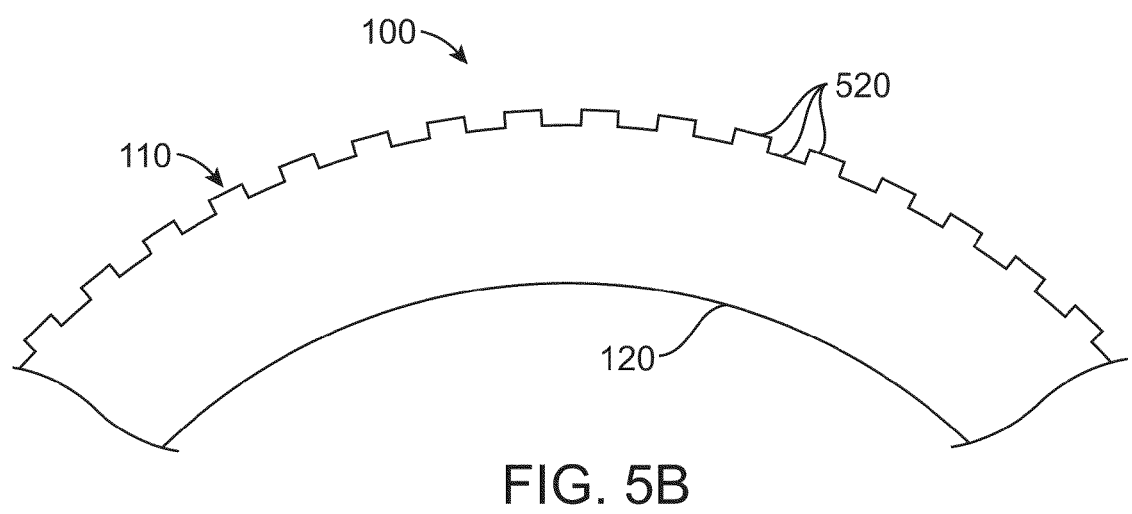
FIG. 5B shows structures on an onlay to promote epithelialization and adhesion of the epithelium to an onlay, according to embodiments of the present invention.

FIG. 5B shows structures 520 on an onlay to promote epithelialization and adhesion of the epithelium to an onlay, according to embodiments of the present invention. The structures can be disposed on the anterior surface of the onlay. The structures may comprise at least one of indentations, castellation, nanostructures, structures to create Van der Waals forces and/or surface roughening, for example as described above.

Figure 5C:
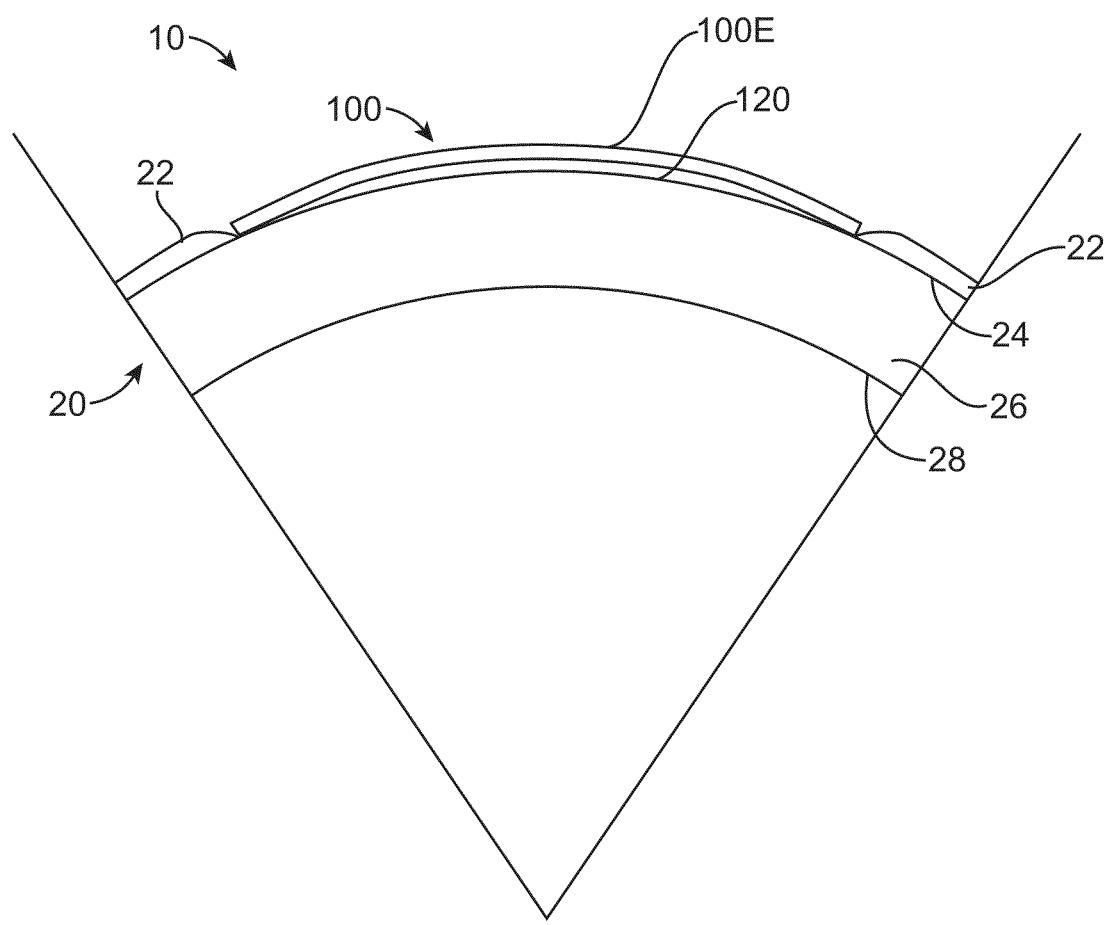
FIG. 5C shows epithelial cells on an anterior surface of an onlay prior to implantation, according to embodiments of the present invention.

FIG. 5C shows an epithelium 100E comprising epithelial cells on an anterior surface of an onlay prior to implantation. The epithelial cells may comprise epithelial cells grown on the onlay prior to placement on the eye. The onlay may be seeded with epithelial cells to promote epithelialization, for example seeded subsequent to adherence of the onlay on the cornea.

VI. Positioning of Onlay

Figure 6A:
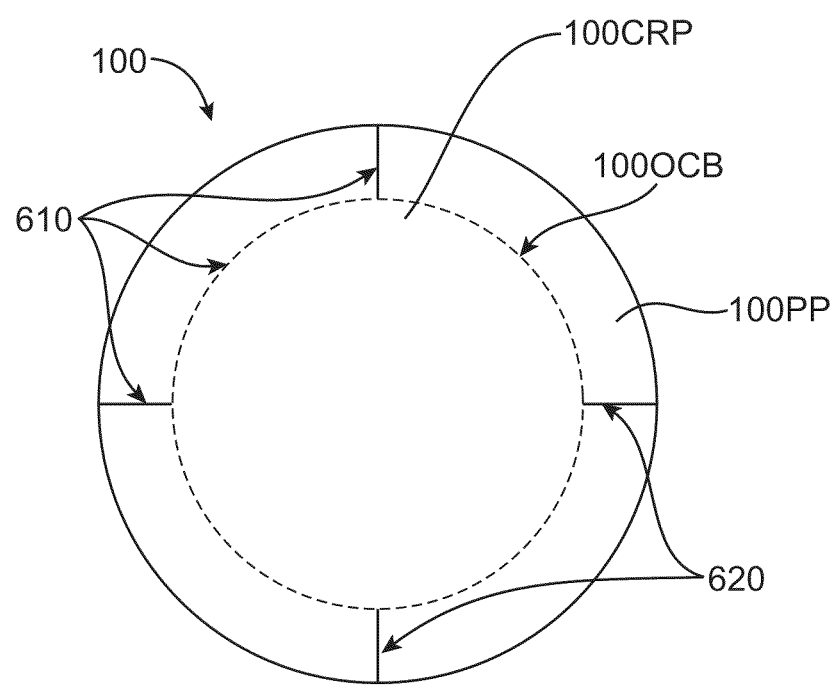
FIG. 6A shows indicia on an onlay for positioning the only on the cornea, according to embodiments of the present invention.

FIG. 6A shows indicia 610 on onlay 100 for positioning the onlay on the cornea. The indicia may be visible through an operating microscope to allow the physician and/or surgeon to align the onlay with the eye. The indicia may comprises axis, dots or other marks to indicate an axis, for example an axis of astigmatism. The indicia may include axes 620 for correction of astigmatism and high order aberrations. The indicia may comprise a circle to indicate a boundary of the optical zone of the onlay, for example a boundary between a central portion of the onlay for optical correction and a peripheral portion of the onlay for adherence to the cornea. The circular indicia may allow the surgeon to align the onlay with the optically useful region of the cornea, for example over the pupil.

VII. Innervation of Onlay

Figure 7A:
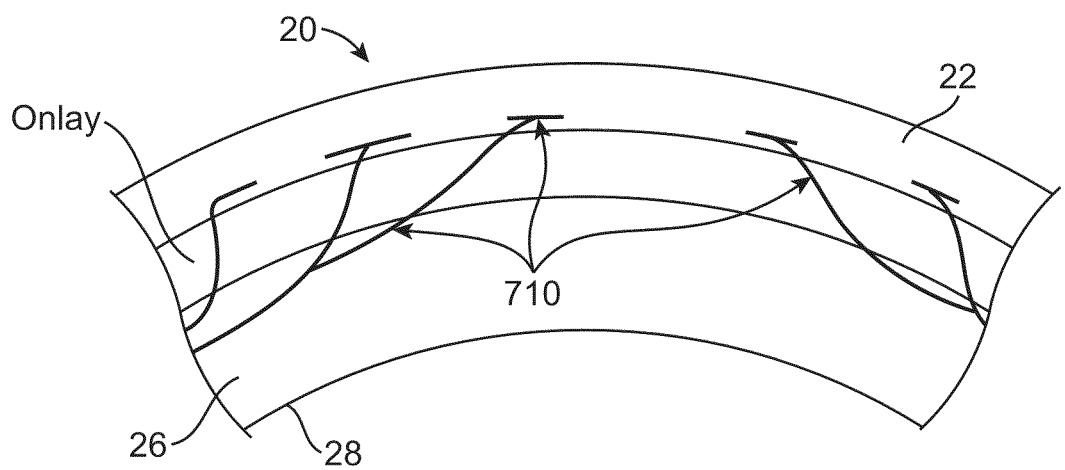
FIG. 7A shows innervation of an onlay, according to embodiments of the present invention.

FIG. 7A shows innervation of an onlay subsequent to placement on the eye. Innervation of the onlay can provide a stimulus to the patient to blink, for example when the eye is dry, such that the onlay and anterior surface of the eye can be hydrated naturally by the patient so as to improve biocompatibility. The cornea includes nerve fibers 710 that can regenerate and/or grow. The nerve fibers can extend from the stroma into the onlay, and in some embodiments may extend through the onlay to the epithelium. The onlay may comprise many materials and can be adhered, welded, formed and/or shaped as described above, and an onlay material as described in US 2006/0134170, may be used so as to allow innervate the onlay subsequent to placement on the eye.

VIII. Delivery of Therapeutic Agent from Onlay

The corneal onlays as described above may comprise at least one of an antibiotic, a steroid, a non-steroidal anti-inflammatory (hereinafter "NSAID"), an analgesic or an anesthetic.

The onlay may comprise a therapeutic agent. The therapeutic agent may comprise at least one of an analgesic, an anti-inflammatory, an antibiotic, a non-steroidal anti-inflammatory, a steroid or an epithelial growth factor to enhance epithelialization. The analgesic may comprise at least one of gabapentin, proparacaine, lidocaine, or tetracaine or a derivative thereof. The antibiotic may comprise tobramycin or a derivative thereof. The non-steroidal anti-inflammatory may comprises at least one of diclofenac, nepafenac, or suprofen or a derivative thereof. The steroid may comprise at least one of fluorometholone, dexamethasone or prednisolone or a derivative thereof. The growth factor may comprise at least one of fibroblast growth factor, fibronectin, or arginine, glycine aspartic acid (RGD) comprising peptide sequence or a derivative thereof. The therapeutic agent may comprise a nerve growth factor (NGF) for innervation of the onlay.

In some embodiments, an analgesic therapeutic agent may comprise an anesthetic therapeutic agent configured for delivery to the cornea at an amount so as to have an analgesic effect and reduce pain, for example without numbing the cornea.

The onlay may comprise a sustained release material, for example a bioadhesives and/or mucoadhesive compositions as described in U.S. Pat. Nos. 5,814,329; 5,942,243; and U.S. Pub No. 2004/0143026; the disclosures of which U.S. patents and publications may be suitable for combination in accordance with some embodiments of the present invention described herein. The onlay may comprise micro-particles, for example with delivery agents as described in U.S. Pat. No. 6,958,158, the disclosure of which may be suitable for combination in accordance with some embodiments of the present invention. The onlay may comprise a drug eluting structure, for example a layer of drug releasing material. The drug eluting structure may be disposed near a surface of the onlay, such that the structure elutes the drug toward through the surface toward a targeted tissue disposed near the surface of the onlay, for example a target surface in contact with the surface of the onlay.

IX. Therapeutic Coverings to Inhibit Edema.

Coverings can be configured for positioning over the onlays so as to inhibit swelling following implantation surgery. The therapeutic coverings may comprise a water inhibiting layer, high oxygen permeability, a conforming outer portion and an optical inner portion.

Figure 8A:
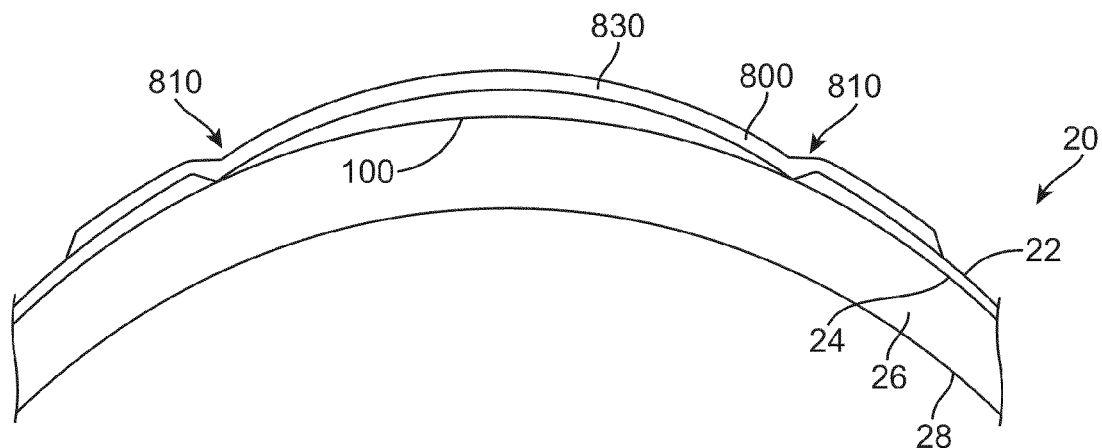
FIG. 8A shows a therapeutic covering positioned over a corneal onlay to inhibit swelling of the cornea.

FIG. 8A shows a therapeutic covering 800 positioned over corneal onlay 100 to inhibit swelling of the cornea. The onlay can be positioned on the cornea in many ways as described above, for example with a pocket, a flap, or epithelial debridement. The onlay is shown positioned on an area of Bowman's membrane where epithelium has been debrided. The covering comprises a water inhibiting layer 830, such that water penetration into the cornea through the covering is inhibited, such that swelling of the cornea can be inhibited when the covering is adhered to the cornea with suction. Therapeutic covering 800 can be sized to cover the onlay and to extend over the intact epithelium when the onlay is positioned on the cornea, so as to seal the cornea. The covering may comprise a hydrophobic portion on the lower surface such that the covering sticks to the cornea with adhesion and water suction from endothelial pumping as described above. The onlay may comprise an annular structure 810 sized to fit the onlay and the epithelium, and may press downward on the onlay near the periphery so as to inhibit growth of epithelium under the onlay.

Figure 8B:
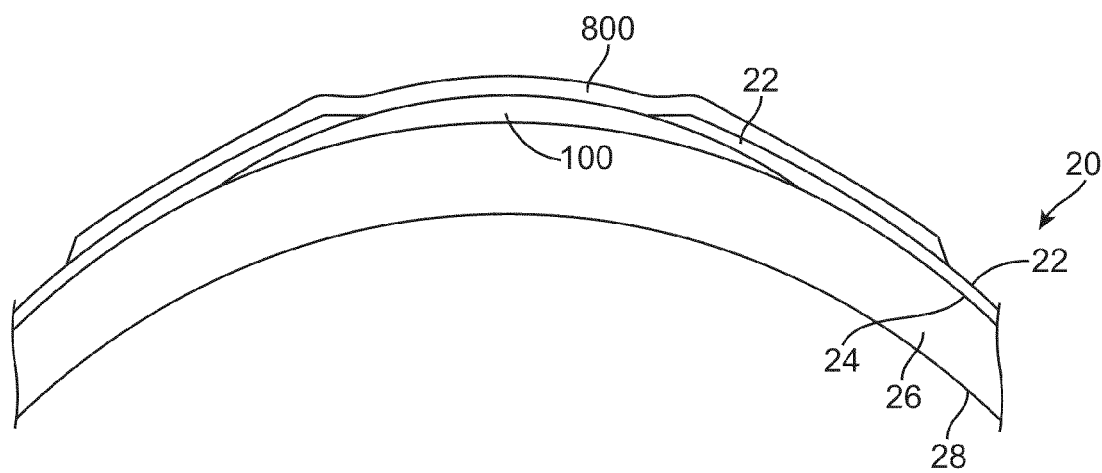
FIG. 8B shows the therapeutic covering as in FIG. 8A positioned over the onlay with epithelium regenerating over the onlay.

FIG. 8B shows the therapeutic covering as in FIG. 8A positioned over the onlay with epithelium regenerating over the onlay. The epithelium 22 has regenerated centripetally inward so as to at least partially cover the onlay 100.

Figure 8C:
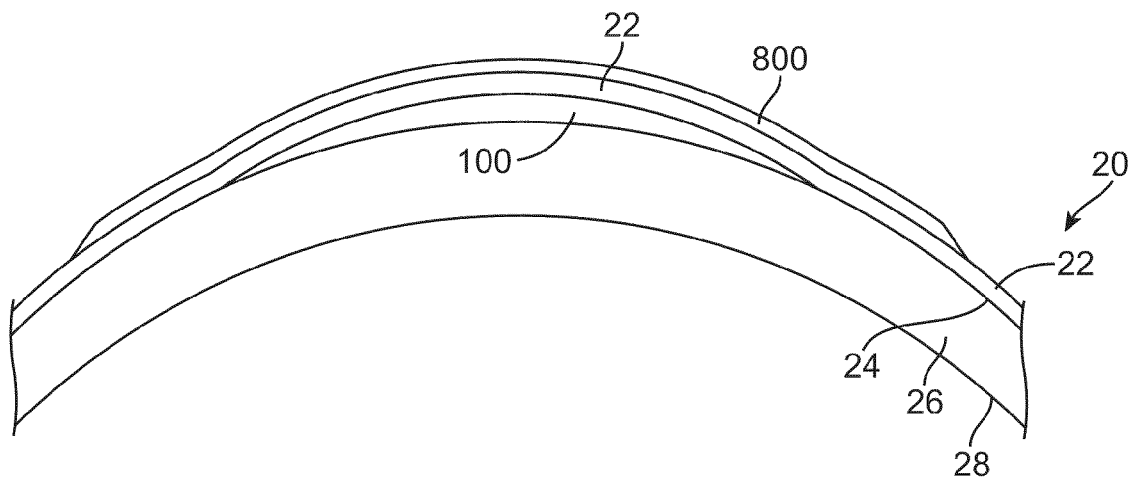
FIG. 8C shows the therapeutic covering as in FIG. 8A with epithelium regenerated under the covering and over the onlay, such that the covering is configured for removal of the therapeutic covering.

FIG. 8C shows the therapeutic covering 800 as in FIG. 8A with epithelium 22 regenerated under the covering and over the onlay 100, such that the covering is configured for removal. Water can be provided at the edge of the covering to hydrate the cornea and remove the covering.

Figure 8D:
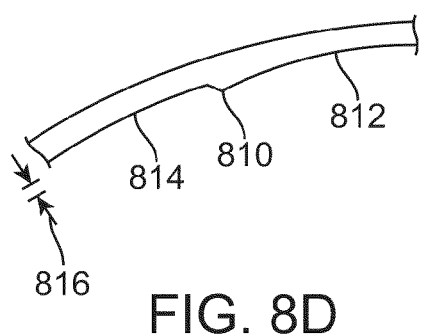
FIG. 8D shows an annular structure of a covering, which annular structure is sized to an outer perimeter of the onlay so as to fit the onlay and the epithelium to inhibit epithelial growth under the onlay.

FIG. 8D shows an annular structure of a covering, which annular structure is sized to an outer perimeter of the onlay so as to fit the onlay and the epithelium to inhibit epithelial growth under the onlay. The covering may comprise an inner portion 812 and an outer portion 814 with the annular structure disposed there between. The annular structure may comprise a diameter that corresponds to the diameter of the onlay. The annular structure may comprise a distance 816, such that the annular structure extends downward from the lower surface of the covering to fit the onlay and the epithelium. For example, the epithelium may comprise a thickness of about 50 um. The outer perimeter of the onlay may comprise a thickness less than the epithelium, for example about 10 um. The annular structure may extend downward, for example about 40 um, so as to correspond to the thickness of the onlay at perimeter and the thickness of the epithelium. The annular structure may comprise an inner radius of curvature along the inner portion to fit the onlay, and an outer radius of curvature along the epithelium to fit the cornea.

Figure 9A:
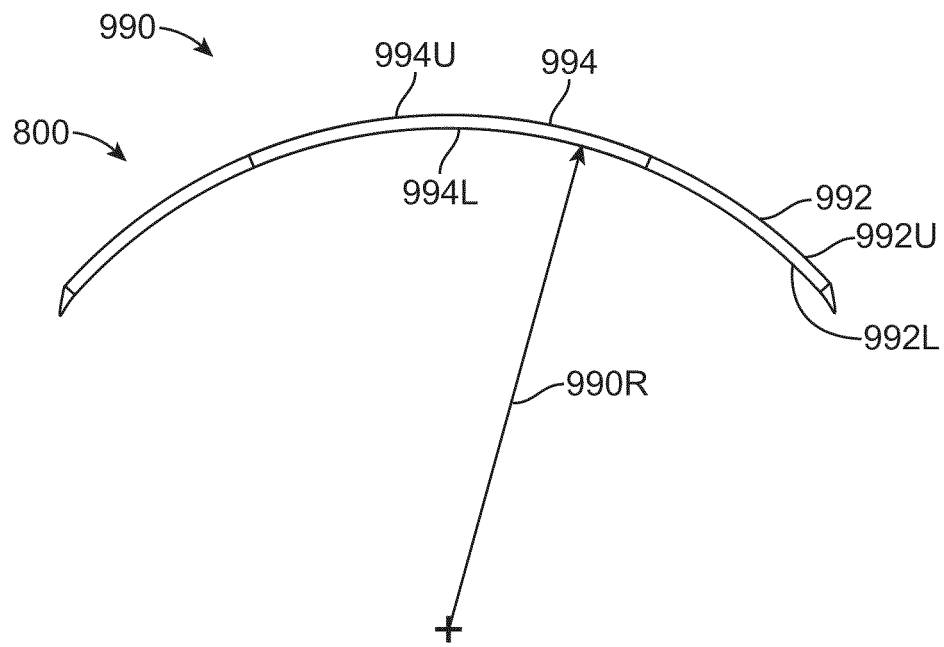
FIG. 9A shows a therapeutic covering configured for placement over an onlay, which covering comprises an outer portion configured to conform to the cornea so as to seal the covering over the cornea and an non-conforming inner portion configured to retain an optical shape and smooth the cornea for vision, according to embodiments.
Figures 1, 9A:
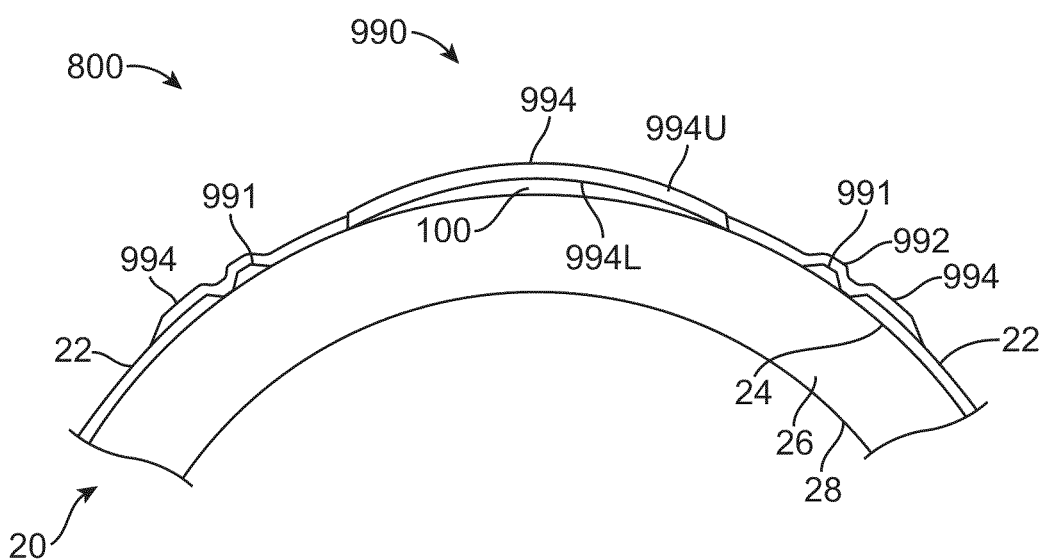

FIG. 9A shows a therapeutic covering 990 comprising an outer portion 992 configured to conform to the cornea so as to seal the covering over the cornea and an non-conforming inner portion 994 configured to retain an optical shape and smooth the cornea for vision. The inner portion 994 comprises an upper surface 994U and a lower surface 994L. The outer portion 992 comprises an upper surface 992U and a lower surface 992L. The covering may comprise an upper hydrophilic layer along each of the upper surfaces, a middle hydrophobic layer along each of the inner and outer portions, and a lower hydrophilic layer along each of the inner and outer portions. The upper tear contacting layer can be hydrophilic to smooth the tear liquid to a film, and the lower surface that contacts the cornea may comprise a hydrophobic surface, a hydrophilic surface, or a combination thereof. The hydrophobic surface may comprise a surface that sticks to the cornea and the hydrophilic surface may comprise a surface that can slip, for example in the presence of water for removal. In some embodiments drying of the hydrophilic surface and/or cornea may provide adherence of the dried hydrophilic surface to the dried cornea. The hydrophobic and hydrophobic layers can be similar to those described above. While many hydrophilic coatings can be used, the lubricous coating may comprise commercially available N-vinyl pyrrolidone (NVP), polyamine based coatings, methacrylate based coatings, and lubricous coatings commercially available from Surmodics Inc., Tri-Star Plastics Inc. and AST Products Inc. The hydrophilic coating may comprise phosphorylcholine technology, for example a coating commercially available from Vertellus.

The covering may comprises a thickness sufficient to inhibit water through the covering and an oxygen permeability so as to inhibit swelling of the cornea. For example the thickness of the covering can be within a range from about 20 to about 200 microns. The covering may comprise an oxygen permeability, also referred to as Dk, of at least about 350, for example 400 or even 500 or more. The covering may comprise a hydrophobic NuSil inner layer, for example, configured to transport oxygen and inhibit passage of water, and upper and lower hydrophilic layers, respectively, as described above. The silicone layer may comprise, for example, dimethyl diphenyl methyl vinyl silicone. The hardness of the covering, the thicknesses and oxygen can be configured by one of ordinary skill in the art to provide the sealing, water barrier, oxygen and optical functions to reduce edema based on the teachings described herein.

The thin lens covering may comprise four characteristics that provide: a barrier against tear liquid entering the debrided zone, high oxygen permeability, and a good optical zone in the center of the lens, and an environment that encourages healthy epithelial re-growth. For example, silicone may have a very high oxygen permeability. The thin lens covering layer comprising hydrophobic silicone may be covered with a hydrophilic upper layer to encourage healthy epithelial re-growth. The silicone layer may be coated on the lower side with a hydrophilic lubricant.

The inner portion 994 can be configured in many ways to provide the optical correction surface, water barrier, and high oxygen transport. The inner portion may comprise a size from about 5 mm to about 9 mm to correct vision, for example a diameter within a range from about 6 to 8 mm to correct vision. The central portion can be configured to retain the optical surface, even when the cornea underneath is somewhat irregular in many ways. For example, the inner portion may comprise a thickness from about 50 to about 200 microns to correct vision. The inner portion may comprise a hardness parameter within a range from about Shore A 30 durometer to about 94 M on the Rockwell scale, such that the inner portion retains the optical surface.

The outer portion 992 can be configured in many ways to seal the covering against the epithelium and provide barrier function when the covering is positioned over the onlay. For example, the outer portion may comprise a thickness from about 20 to about 100 microns, and may comprise a hardness durometer parameter within a range from about 20 to about 60. The outer portion may comprise a size across from about 5 mm to about 12 mm, for example a diameter within a range from about 7 mm to about 10 mm.

The covering 990 can be configured in many ways so as to seal the cornea. The outer portion and inner portion comprise a lower surface radius of curvature 990R. The radius of curvature 990R can be the same for both the inner portion and the outer portion and fit to the patient. For example, the radius of each the inner portion and the outer portion may comprise about 7.5 mm. Alternatively, the inner portion may comprise a radius of curvature fit to the corneal profile, and the outer portion may comprise a slightly shorter radius of curvature fit snugly to the peripheral debrided cornea.

FIG. 9A-1 shows a therapeutic covering as in FIG. 9A positioned over an onlay, with the outer portion conforming to one or more irregularities 991 on the underlying Bowman's membrane and/or stromal tissue, so as to seal the covering over the onlay and adhere the onlay to the cornea when the epithelium grows over the onlay.

Figure 9B:
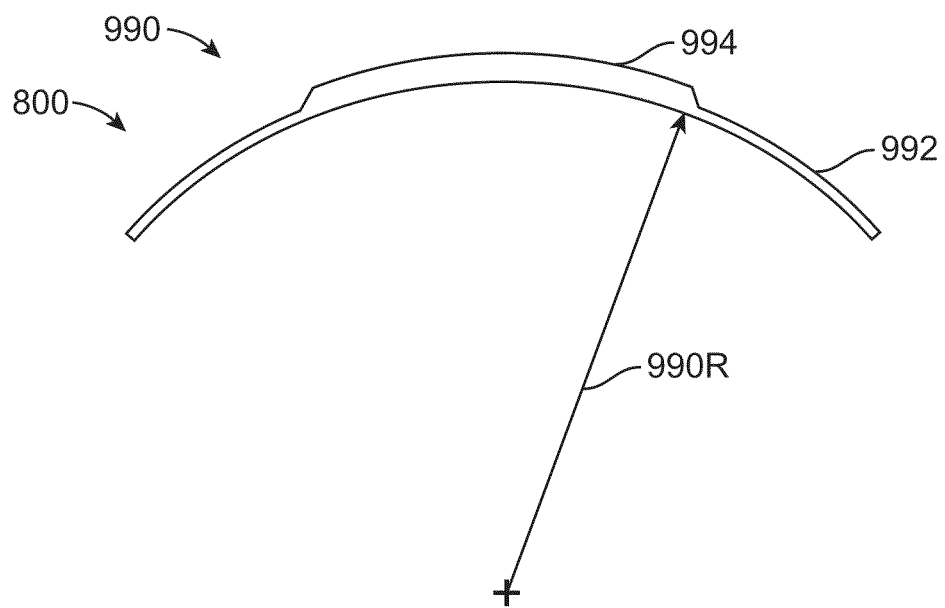
FIG. 9B shows a therapeutic covering as in FIG. 9A comprising a covering molded with a homogeneous material, in which the outer portion comprises a thickness configured to conform with the cornea and in which the inner portion comprises thickness configured to retain the optical shape.

FIG. 9B shows a therapeutic covering as in FIG. 9A comprising a covering molded with a homogeneous material, in which the outer portion comprises a thickness configured to conform with the cornea and in which the inner portion comprises thickness configured to retain the optical shape. The outer portion 992 may comprise a thickness of no more than about 100 microns. For example the outer portion may comprise a thickness of about 50 microns at the boundary with the inner portion, and linearly taper from 50 microns at the boundary with the inner portion to about 5 microns at the periphery of the outer portion. The inner portion may comprise a thickness of no more than about 200 microns. For example, the inner portion may comprise a thickness of about 100 microns. Many materials can be used as described above. For example, the single piece covering may comprise silicone having a water content within a range from about 0.1% to about 10%, for example no more than about 1%, and a hardness Shore A durometer parameter within a range from about 20 to about Shore A 70, for example about 30.

Figure 9C:
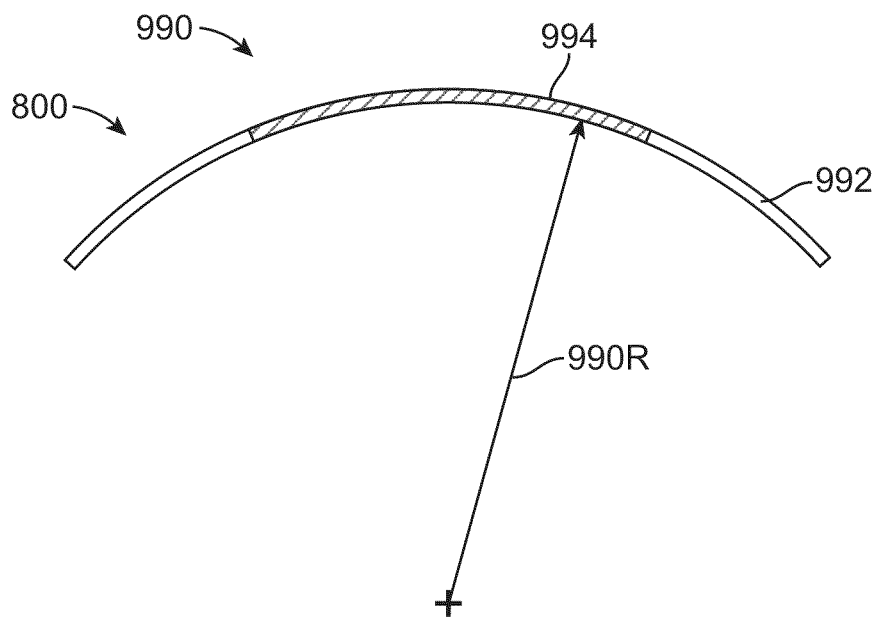
FIG. 9C shows a therapeutic covering as in FIG. 9A comprising a covering molded with a first outer material and a second inner material, in which the outer portion comprises a first hardness configured to conform with the cornea and in which the inner portion comprises second hardness configured to retain the optical shape.

FIG. 9C shows a therapeutic covering as in FIG. 9A comprising a covering molded with a first outer material and a second inner material, in which the outer portion 992 comprises a first hardness configured to conform with the cornea and in which the inner portion 994 comprises second hardness configured to retain the optical shape. The outer material may comprise many materials as described above. For example, the outer material may comprise silicone having a hardness Shore A durometer parameter from about 20 to about 40, and the inner material may comprise silicone having a hardness Shore A durometer parameter from about 40 to about 70.

Figure 9D:
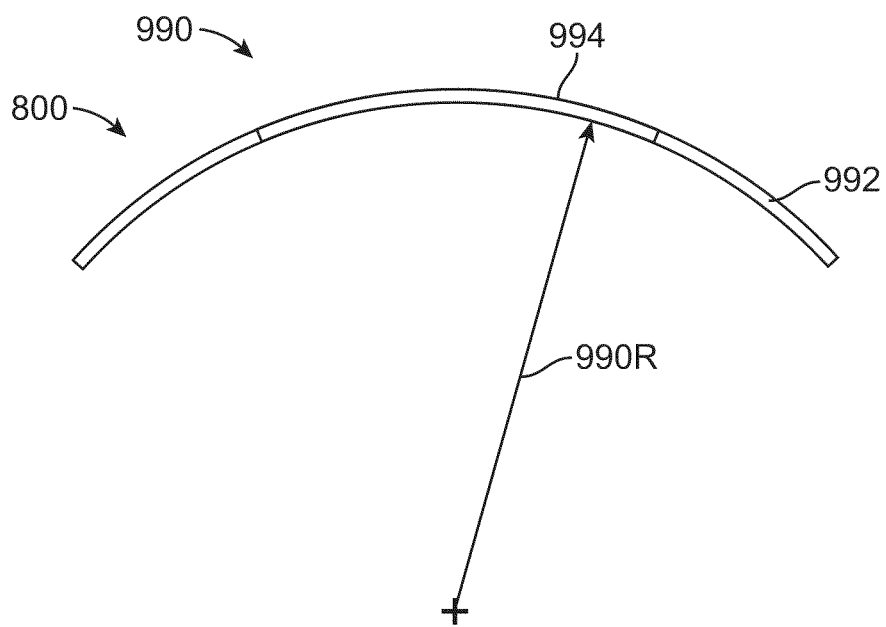
FIG. 9D shows a therapeutic covering as in FIG. 9A comprising a first outer portion composed of a first material affixed to a second inner portion composed of a second material, in which the outer portion comprises a first hardness configured to conform with the cornea and in which the inner portion comprises second hardness configured to retain the optical shape.

FIG. 9D shows a therapeutic covering as in FIG. 9A comprising a first outer portion composed of a first material affixed to a second inner portion composed of a second material, in which the outer portion comprises a first hardness configured to conform with the cornea and in which the inner portion comprises second hardness configured to retain the optical shape. The central inner portion may comprise a rigid central portion, of a higher durometer, of 6 to 9 mm in diameter to improve visual acuity in patients. This optically clear central portion may be up to about 8 mm in diameter, for example. The central inner portion may provide optical power when placed on the eye, for example with a shaped upper surface to correct vision and a lower surface shaped to the cornea. The center portion may comprise many materials, for example an RGP material. The peripheral outer portion may comprise a less rigid material, of a lower durometer, than the central portion so as to conform to the cornea along the debrided surface and around the debrided edge and irregularities within the debrided surface. Since optical clarity may not play a substantial role in the peripheral portion, the peripheral portion may comprise a transparent or opaque material. For example the peripheral portion may comprise an opaque material so as to define an aperture of the inner portion, for example to improve vision.

Figure 9E:
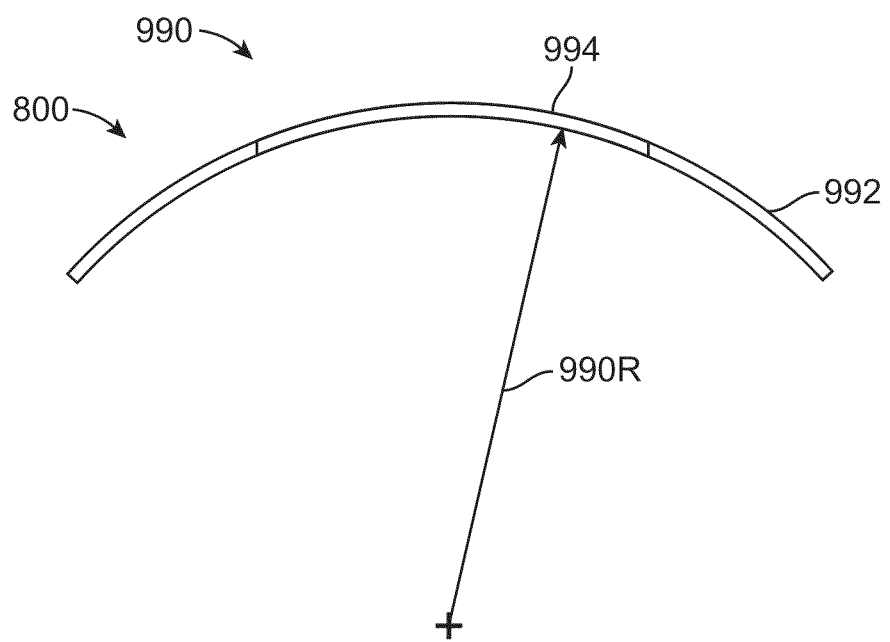
FIG. 9E shows a covering comprising an annular configuration with the inner portion comprising an optic zone with a lower surface composed of a hydrophobic material configured for placement over the epithelial defect and the outer portion 2992 comprising a lower surface having a hydrophilic material configured to contact the epithelium.

FIG. 9E shows a covering comprising an annular configuration with the inner portion 994 comprising an optic zone with a lower surface composed of a hydrophobic material configured for placement over the epithelial defect and the outer portion 992 comprising a lower surface having a hydrophilic material configured to contact the epithelium. The diameter of the hydrophilic layer may have greater than the diameter of the hydrophobic layer so as to allow the hydrophilic layer to contact the epithelium when the inner hydrophobic layer is sucked down over the debrided area of the cornea.

EXPERIMENTAL

Onlays may be constructed in accordance with the teachings described herein and parameters such as the properties of the onlay and dimensions determined empirically such that the onlay adheres to the cornea. For example, the onlay may comprise a degradable water inhibiting layer comprising PLA and PGA copolymer disposed on the anterior side of the onlay. Studies conducted so as to configure the degradable layer such that the copolymer degrades within about 4 days, such that the onlay passes nutrients from the stroma through the onlay to the epithelium.

Studies may also be conducted with the therapeutic covering, as described above, such that the covering can be used with many of the onlays as described above. Therapeutic coverings may be constructed in accordance with the teachings described herein and parameters such as the properties of the covering and dimensions determined empirically such that the covering sucks down onto the cornea so as to adhere the onlay to the cornea. For example, the dimensions of an outer conforming portion and a inner optical portion of the covering may be determined. The hardness of the one or more materials may also be determined. For example, a hardness of silicone material such as a durometer hardness parameter may be tested. Upon laboratory testing, experimental animal studies can be conducted and clinical trials on people conducted to determine known outcome parameters such as visual acuity, cornea edema and pain.

Figure 10A:
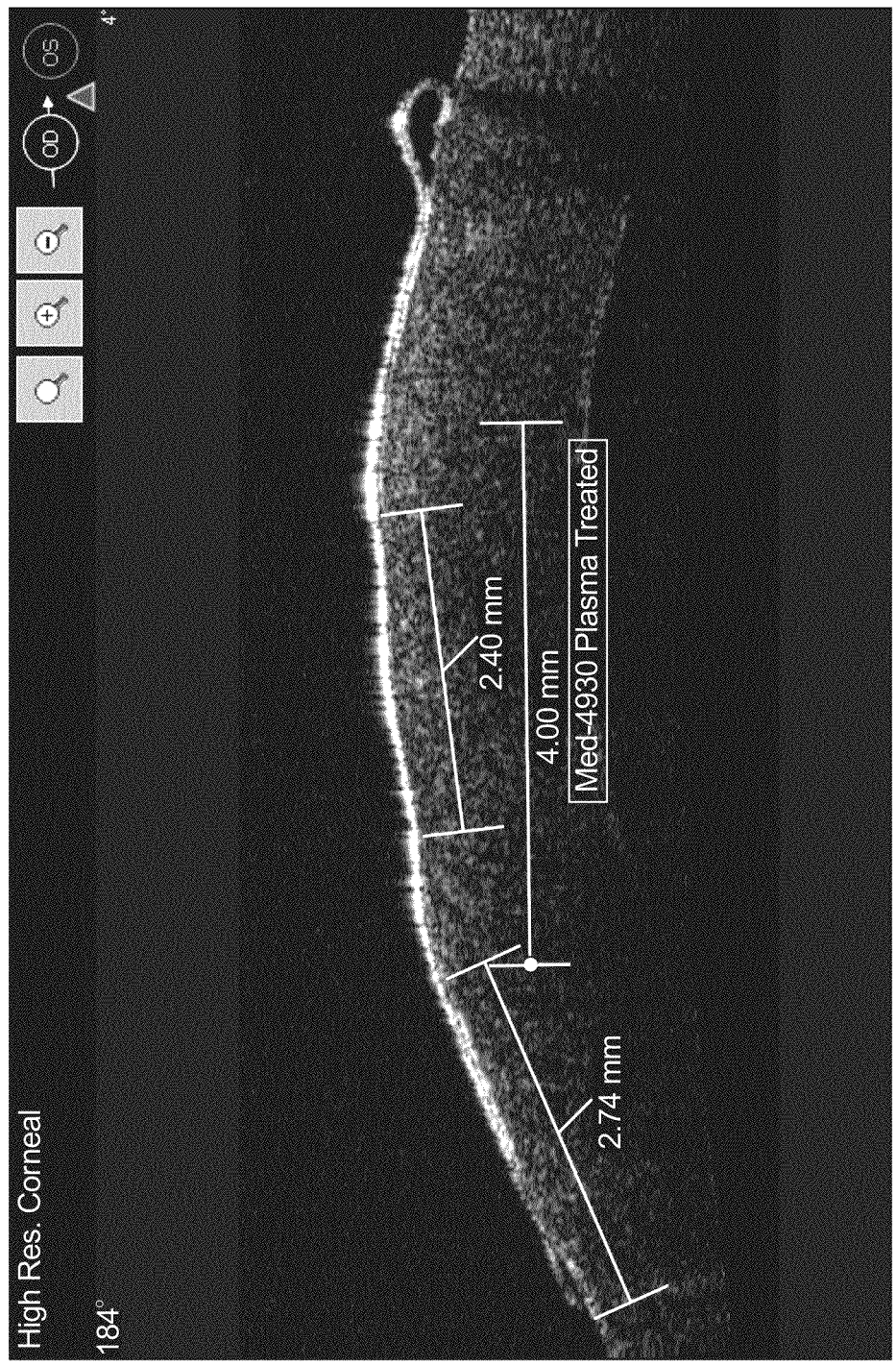
FIG. 10A shows an OCT image of an onlay comprising a therapeutic covering conforming substantially to one or more irregularities of a debrided corneal surface, in accordance with embodiments.

FIG. 10A shows an optical coherence tomography image of a covering conforming substantially to irregularities of a debrided corneal surface. The shown surface comprises a de-epithelialized porcine eye. The covering is shown conforming to irregularities of the cornea, including the boundary of the epithelial defect. The covering comprised a thickness of about 50 um and a Shore A durometer of about 30. These data suggest suitable parameters for the edge portion, and that the inner portion may comprise a Shore A durometer of more than 30 when the inner portion is no more than about 50 um thick.

The empirical studies may comprise laboratory studies, for example of conformance of a covering to a target shape of the onlay and corneal surface. For example, the onlay can be placed over a 7.5 mm radius of curvature surface with a 2 mm hole in the middle of the test surface to simulate a corneal irregularity. With a inner portion that may be more soft than ideal, the inner portion may droop over the hole. The hardness and/or thickness of the inner portion can be increased such that the inner portion retains the optical shape and does not droop over the hole. For example, experiments have suggested that a 50 um uniform thickness covering with a durometer of 30 may droop slightly such that a thicker and/or harder covering may provide improved clinical results. Patients with onlays may be tested subsequent to laboratory testing to optimize empirically the parameters of the therapeutic covering and onlay so as to achieve the above stated functions such as edema less than 5% and visual acuity of 20/30 or better when the epithelium is regenerating with re-epithelialization over the onlay.

A person of ordinary skill in the art can conduct empirical studies to determine material properties, coatings and dimensions of a therapeutic covering so as to provide improved water barrier function, decreased pain and increased visual acuity for days one to three post-op, or more.

The teachings of a recently conducted clinical study show that a therapeutic covering may be configured to adhere to the cornea with suction. Although this clinical study used PRK patients, the teaching with respect to suction and adherence of the covering can be combined with the onlays as described herein. The clinical study was conducted with a silicone therapeutic covering about 50 um thick placed over an epithelial defect following PRK. The study has shown mean corneal swelling of no more than about 1% at days 1 and 2 post-op when the patients had epithelial defects, while controls showed about 5%.

This PRK study showed that thin silicone coverings with a hydrophilic coatings on both surfaces can seal and epithelial defect of the cornea and adhere the covering to the cornea with suction. In the post PRK study, the covering was sized larger than the epithelial defect, and a contact lens positioned over the flap for about one hour to retain the covering over the epithelial defect such that the covering could be retained with suction from endothelial pumping. The contact lens was removed and the covering remained adhered to the cornea and sealed to the cornea with suction. A person of ordinary skill in the art, based on the teachings described herein, can position an onlay on Bowman's membrane, for example under the epithelium, and position the therapeutic covering over the onlay, such that the epithelium grows over the onlay and in contact with the onlay so as to seal the cornea and minimize swelling when the epithelium regenerates over the onlay. The recent post PRK study also indicated that an approximately 50 um thick silicone covering may slightly increase swelling slightly at day 3 post PRK, such that a therapeutic covering comprising an oxygen permeability Dk parameter of at least about 350 may be helpful to inhibit swelling of the cornea with the onlay positioned on the cornea.

Figure 10B:
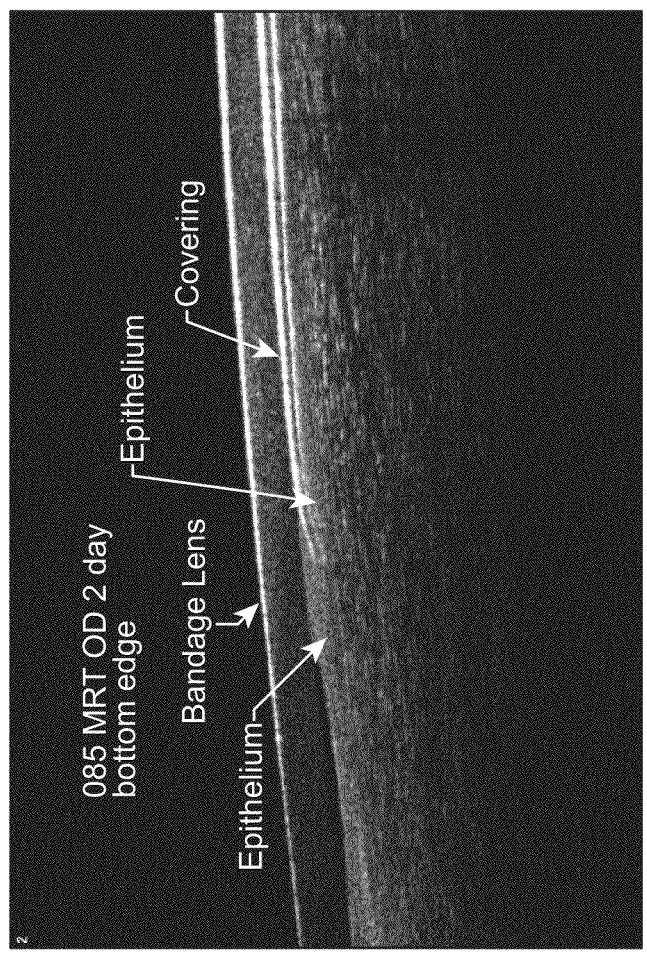
FIG. 10B shows a therapeutic covering from a post-PRK study with conformance of the covering to the epithelium and epithelium growing above and below the periphery of the covering, such that covering can be used to seal a cornea with an onlay, in accordance with embodiments.

FIG. 10B shows a therapeutic covering from a post-PRK study with conformance of the coving to the epithelium and epithelium growing above and below the periphery of the covering, such that a similar covering can be used to seal a cornea with an onlay, in accordance with embodiments. The optical coherence tomography image shows the clinically tested therapeutic covering adhered to an eye so as to remodel the epithelium near the edge of the 9 mm diameter covering. The image shows the covering adhered to the epithelium such that the covering induced an irregularity of the epithelium near the edge of the covering. The epithelium has grown over the covering slightly at the periphery and extends under the covering for a substantial distance, such that the cornea is sealed with the covering and the epithelium. A bandage lens is shown over the covering for the follow up visit. This data shows the covering adhered to the cornea with endothelial suction. A person of ordinary skill in the art will recognize that the periphery of the covering may be thinned so as to inhibit or minimize the irregularity of the epithelium at the periphery, based on the teachings described herein. As the endothelial suction was sufficient to induct the peripheral irregularity of the epithelium, the rigidity of the inner portion may be configured to smooth the epithelium, based on the teachings described herein.

Figure 10C:
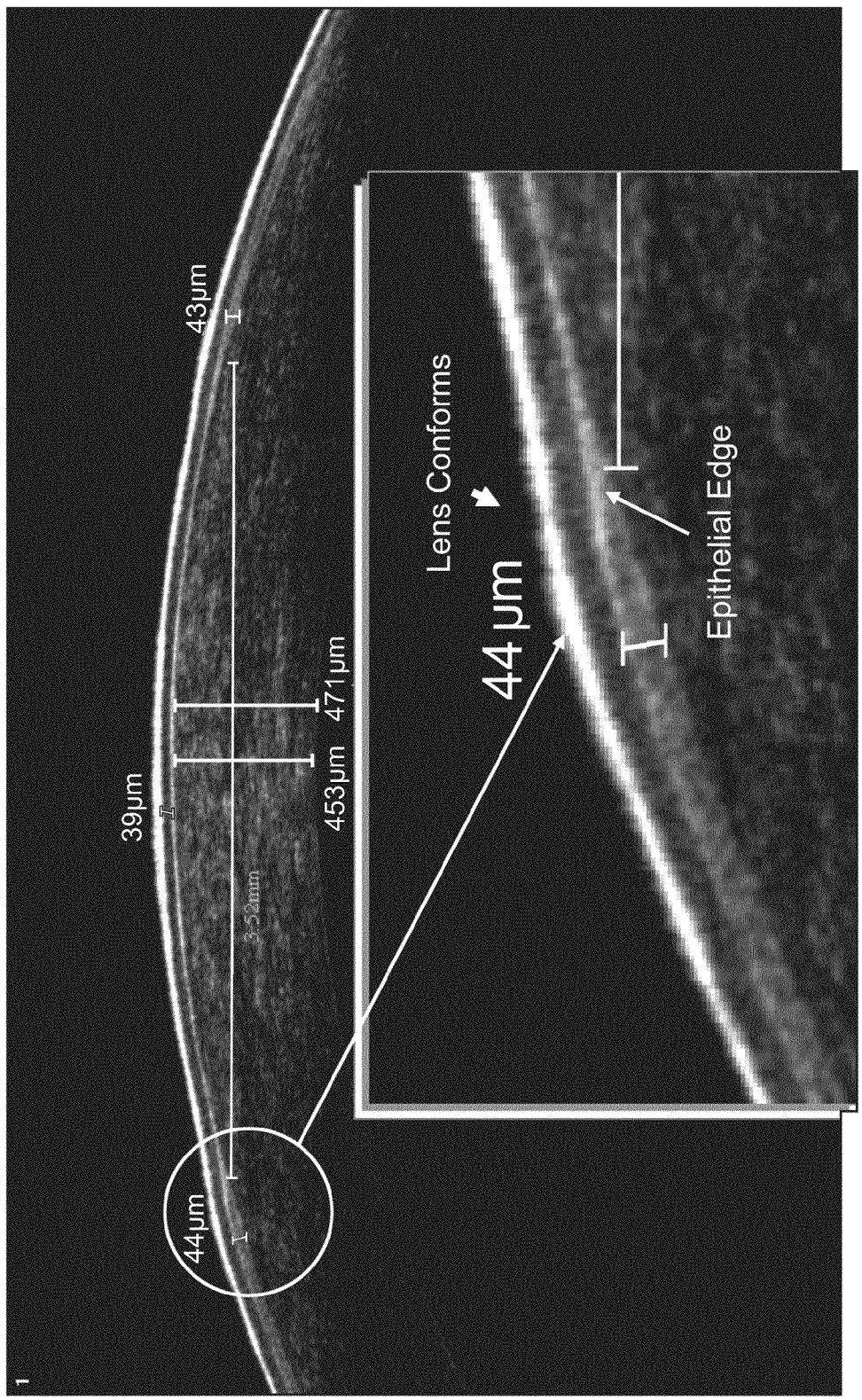
FIG. 10C shows a therapeutic covering from a post-PRK study with conformance of the covering to the epithelium and sealing of the cornea at 24 hours post-op, such that covering can be used with an onlay, in accordance with embodiments.

FIG. 10C shows a therapeutic covering from the post-PRK study with conformance of the coving to the epithelium and sealing of the cornea, and a similar covering can be used with an onlay, in accordance with embodiments. The optical coherence tomography image shows a therapeutic covering conforming to an epithelial layer of a PRK patient at 24 hours post-op. The covering conforms to the epithelial defect, so as to seal the cornea. The covering comprises a silicon material having a thickness of about 50 um and a Shore A durometer of about 30. The epithelium is shown growing under the covering and continued to grow such that the eye re-epithelialized under the covering.

An example of a therapeutic covering in accordance with the above may comprise a single piece of molded silicon having a water content of no more than about 2%, an outer portion with an outer size of about 7 to 12 mm across, for example 10 mm diameter, an inner portion with a size of about to 6 to 9 mm across, for example 8 mm diameter. For example, the onlay may comprise an 8 mm diameter, and the inner portion of the covering may comprise about 8 mm across so as to correspond to the onlay, and the outer portion of the covering may extend to about 10 mm across so as to contact the epithelium and seal the cornea with the onlay positioned under the covering. The silicone may comprise hardness corresponding to a Shore A durometer from within a range about 30 to about 70, for example a uniform hardness corresponding to a durometer of about 40. The thickness of the outer portion at the periphery of the covering may comprise about 5 to 40 microns across, for example 10 microns. The thickness can gradually increase toward an inner boundary of the outer portion of the covering having a thickness within a range from about 40 to 80 microns. The inner portion of the covering may comprise an uniform thickness within a range from about 80 to 120 microns across, for example about 100 microns. The inner portion may comprise optical surfaces with the refractive vision correcting shapes formed thereon, and the lower surface of the covering may correspond to the anterior surface of the onlay. The covering comprising a molded single piece can be coated on the upper surface with a hydrophilic layer, for example a lubricous coating, and coated on the lower surface with a hydrophilic layer, for example a lubricous coating. The outer portion of the covering can conform to and seal against the surface of the epithelium and irregularities thereof. The covering can be adhered to the onlay and the onlay can be adhered to Bowman's membrane with water suction from endothelial pumping, as described above. The central portion of the covering may comprise the optical surface for vision which and may not conform to irregularities of the cornea such as of the epithelium regenerating over the onlay. The oxygen permeability and corresponding Dk of the covering can exceed 350, for example 400 or even 500 or more, so as to at least one of inhibit or minimize pain and swelling when the epithelium regenerates, for example regenerates over the onlay. The swelling of cornea on and after one day post-op can be 5% or less, for example 2% or less. Work in relation to embodiments suggests that the onlay may be placed in a pocket of epithelium through an incision, such that the swelling of the cornea may comprise less than 2% at the first day post-op, and that the covering may be removed at the first day post-op when the epithelial incision has healed.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims and the full scope of the equivalents thereof.

What is claimed is:

1. A method of correcting vision comprising:
    (a) obtaining an onlay configured to correct vision of an eye of a human and a separate therapeutic covering;
    (b) placing the onlay on the cornea of an eye of a patient so as to correct vision of the eye; and subsequently
    (c) placing the covering on the cornea so that it covers and extends around the onlay, thereby promoting regeneration of epithelium between the covering and the onlay;
    wherein the therapeutic covering is a solid covering device that comprises a water inhibiting layer, thereby configuring the covering to adhere to the cornea by endothelial cell suction.

2. The method of claim 1 wherein the onlay is positioned in an epithelial pocket with epithelium disposed between the onlay and the covering.

3. The method of claim 1 wherein the epithelium is debrided to expose the Bowman's membrane and the onlay positioned on the Bowman's membrane.

4. The method of claim 1,
    further comprising:
        (d) removing the covering once epithelium has regenerated between the covering and the onlay so as to at least partly cover the onlay.

5. The method of claim 4 wherein the covering when the covering is removed after about 4 days.

6. The method of claim 4, wherein removing the covering comprises administering water to the eye so as to loosen the covering from the epithelium of the eye.

7. The method of claim 1 wherein the covering is permeable to oxygen.

8. The method of claim 1 further comprising: measuring the cornea; and selecting the covering from among a plurality of coverings in accordance with data obtained from the measuring such that the seal is formed when the covering is placed on the cornea.

9. The method of claim 1, wherein the covering comprises a hydrophobic material facing the cornea.

10. The method of claim 1, wherein the covering comprises a hydrophilic outer surface.

11. The method of claim 1, wherein the covering is shaped to conform to irregularities of the epithelium, thereby adhering the covering and to adhere to the first portion and the onlay to the cornea.

12. The method of claim 1, wherein the covering comprises a thickness within a range from about 25 to about 100 microns and an oxygen Dk parameter of at least about 80.

13. The method of claim 1, wherein the covering comprises an outer portion configured to conform to the cornea so as to seal the covering over the cornea, and an non-conforming inner portion configured to retain an optical shape and smooth the cornea for vision.

14. The method of claim 1, wherein the covering conforms with one or more irregularities on the Bowman's membrane and/or stromal tissue of the eye.

15. The method of claim 1, wherein the covering comprises a homogeneous material, wherein the outer portion comprises a thickness configured to conform with the cornea, and the inner portion comprises thickness configured to retain an optical shape.

16. The method of claim 1, wherein the covering comprises an inner portion and an outer portion, wherein the outer portion has a thickness of no more than about 100 microns tapering at the boundary with the inner portion to about 5 microns at the periphery of the outer portion.

17. The method of claim 1, wherein the covering has a hydrophobic layer or surface comprising silicone.

18. The method of claim 1, wherein the covering has a hydrophobic layer or surface comprising elastomer, silicone elastomer or polyurethane.

19. The method of claim 17, wherein the silicone has a water content within a range from about 0.1% to about 10%.

20. The method of claim 1, wherein the covering is molded with an outer material and an inner material, wherein the outer material has a hardness selected to conform with the cornea, and the inner portion has a hardness selected to retain an optical shape.

21. The method of claim 20, wherein the outer material has a Shore A durometer parameter between about 20 to about 40.

22. The method of claim 20, wherein the inner material has a hardness Shore A durometer parameter between about 40 to about 70.

23. The method of claim 1, wherein the covering comprises a rigid central portion of about 6 to 9 mm in diameter that confers an optical power when placed on the eye.

24. The method of claim 1, wherein the covering has an annular structure sized to an outer perimeter of the onlay so as to fit the onlay and the epithelium to inhibit epithelial growth under the onlay.

25. The method of claim 24, wherein the annular structure extends downward from the lower surface of the covering to fit the onlay and the epithelium.

26. The method of claim 1, wherein the onlay comprises a degradable material so that the onlay degrades within about one week of placement on the cornea.

27. The method of claim 26, wherein the degradable material comprises a material selected from the group consisting of poly-lactic acid (PLA), poly-glycolic acid (PGA) and PLA/PGA copolymer.

28. The method of claim 1, wherein the onlay comprises an anterior water inhibiting layer, and a posterior water permeable layer with a posterior surface shaped to fit an anteriorly exposed surface of the cornea.

29. The method of claim 1, wherein the covering is configured to detach from the onlay once the epithelium of the eye has regenerated between the onlay and the covering.

30. The method of claim 1, wherein the covering has a thickness of no more than about 200 microns and a width of at least about 5 mm to conform to the cornea and the onlay.

31. The method of claim 1, wherein the covering has a thickness within a range from about 25 to about 100 microns.

32. The method of claim 1, wherein the covering has an oxygen Dk parameter of at least about 80 Barrer.

33. A method of placing an onlay in an eye of a patient in need thereof, comprising:
   (a) obtaining an onlay that is selected to improve vision of the eye;
   (b) obtaining a separate therapeutic covering that comprises a water inhibiting layer that is sized and shaped to cover and surround the onlay when the onlay is placed in the eye;
   (c) placing the onlay directly onto an anterior surface of the cornea; then
   (d) placing the therapeutic covering over the onlay such that the covering covers the onlay and the water inhibiting layer seals the covering to the cornea by suction, thereby promoting regeneration of epithelium between the covering and the onlay; and subsequently
   (e) removing the covering from the eye once epithelium has sufficiently regenerated over the onlay such that the onlay adheres to the surface without the covering.

34. The method of claim 33, wherein step (c) comprises placing the onlay under a flap surgically created in the cornea of the eye.

35. The method of claim 33, wherein step (c) comprises placing the onlay into a pocket made in the epithelium.

36. The method of claim 33, wherein step (c) comprises placing the onlay onto an area of the Bowman's membrane of the eye that has been debrided of epithelium.

37. The method of claim 33, wherein the therapeutic covering comprises an annular structure sized to fit the onlay and the epithelium and configured to press downwards on the onlay near the periphery.

38. The method of claim 33, wherein the therapeutic covering comprises an inner portion and an outer portion with an annular structure disposed therebetween that corresponds to the diameter of the onlay.

39. The method of claim 33, wherein the therapeutic covering has a thickness that is less than the epithelium of the eye.

40. The method of claim 33, wherein the therapeutic covering comprises an outer portion configured to conform to the cornea so as to seal the covering over the corneal, and a non-conforming inner portion configured to retain an optical shape and to smooth the cornea for vision.

41. The method of claim 33, wherein the therapeutic covering comprises an outer hydrophilic surface and an inner hydrophobic surface.

42. The method of claim 33, whereby the therapeutic covering is removed after about 4 days.

* * * * *

UNITED STATES PATENT AND TRADEMARK OFFICE
CERTIFICATE OF CORRECTION

PATENT NO. : 9,125,735 B2
APPLICATION NO. : 12/897131
DATED : September 8, 2015
INVENTOR(S) : Juan, Jr. et al.

It is certified that error appears in the above-identified patent and that said Letters Patent is hereby corrected as shown below:

In the Claims
In Column 40, Claim 5, remove "when the covering" so the claim reads: "The method of claim 4 wherein the covering is removed after about 4 days."

Signed and Sealed this
Twenty-eighth Day of June, 2016

Michelle K. Lee
*Director of the United States Patent and Trademark Office*